United States Patent
Gavai et al.

(10) Patent No.: US 12,391,675 B2
(45) Date of Patent: Aug. 19, 2025

(54) NLRP3 MODULATORS

(71) Applicant: INNATE TUMOR IMMUNITY, INC., Princeton, NJ (US)

(72) Inventors: Ashvinikumar V. Gavai, Princeton Junction, NJ (US); Derek J. Norris, Pennington, NJ (US); Daniel O'Malley, New Hope, PA (US); Steven P. Seitz, Swarthmore, PA (US); Jay A. Markwalder, Lahaska, PA (US); David K. Williams, Delran, NJ (US); Hua Gong, King of Prussia, PA (US); Scott Hunter Watterson, Pennington, NJ (US); Christine M. Tarby, Lawrenceville, NJ (US)

(73) Assignee: Innate Tumor Immunity, Inc., Princeton, NJ (US)

( * ) Notice: Subject to any disclaimer, the term of this patent is extended or adjusted under 35 U.S.C. 154(b) by 782 days.

(21) Appl. No.: 17/422,512

(22) PCT Filed: Jan. 13, 2020

(86) PCT No.: PCT/US2020/013264
§ 371 (c)(1),
(2) Date: Jul. 13, 2021

(87) PCT Pub. No.: WO2020/150115
PCT Pub. Date: Jul. 23, 2020

(65) Prior Publication Data
US 2022/0089572 A1   Mar. 24, 2022

Related U.S. Application Data

(60) Provisional application No. 62/791,979, filed on Jan. 14, 2019.

(51) Int. Cl.
| | | |
|---|---|---|
| *C07D 403/04* | (2006.01) |
| *A61P 35/00* | (2006.01) |
| *C07D 401/04* | (2006.01) |
| *C07D 401/14* | (2006.01) |
| *C07D 405/14* | (2006.01) |
| *C07D 409/14* | (2006.01) |
| *C07D 487/10* | (2006.01) |
| *C07D 491/08* | (2006.01) |
| *C07D 493/08* | (2006.01) |
| *C07D 493/10* | (2006.01) |
| *C07D 498/08* | (2006.01) |

(52) U.S. Cl.
CPC ............ *C07D 403/04* (2013.01); *A61P 35/00* (2018.01); *C07D 401/04* (2013.01); *C07D 401/14* (2013.01); *C07D 405/14* (2013.01); *C07D 409/14* (2013.01); *C07D 487/10* (2013.01); *C07D 491/08* (2013.01); *C07D 493/08* (2013.01); *C07D 493/10* (2013.01); *C07D 498/08* (2013.01)

(58) Field of Classification Search
None
See application file for complete search history.

(56) References Cited

U.S. PATENT DOCUMENTS

| | | | |
|---|---|---|---|
| 2022/0087991 A1* | 3/2022 | Watterson | A61K 31/444 |
| 2022/0089566 A1* | 3/2022 | Watterson | C07D 401/04 |
| 2022/0257587 A1* | 8/2022 | O'Malley | C07D 405/14 |

* cited by examiner

*Primary Examiner* — Jeffrey S Lundgren
*Assistant Examiner* — Anthony Joseph Seitz
(74) *Attorney, Agent, or Firm* — Jing G. Sun

(57) ABSTRACT

The present invention provides compounds of Formula (I): (I) wherein all of the variables are as defined herein. These compounds are modulators of NLRP3, which may be used as medicaments for the treatment of proliferative disorders, such as cancer in a subject (e.g., a human).

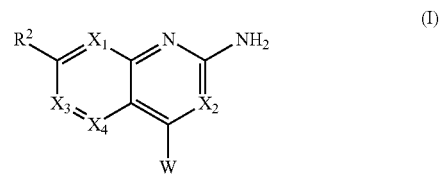

13 Claims, No Drawings

NLRP3 MODULATORS

CROSS-REFERENCE TO RELATED APPLICATIONS

This application is a 371 of International Application No. PCT/US2020/013264 filed on Jan. 13, 2020, which claims the priority benefit of U.S. Provisional Application No. 62/791,979, filed Jan. 14, 2019; the content of which is herein incorporated by reference in their entirety.

TECHNICAL FIELD

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity that contributes to the pathology and/or symptoms and/or progression and/or treatment refractory state of the condition, disease or disorder (e.g., cancers with low T-cell infiltration) in a subject (e.g., a human). This disclosure also features compositions as well as other methods of using and making the same.

BACKGROUND

Nucleotide-binding oligomerization domain-like receptors ("NLRs") include a family of intracellular receptors that detect pathogen-associated molecular patterns ("PAMPs") and endogenous molecules (see, e.g., Ting, J. P. Y. et al., "The NLR gene family: a standard nomenclature," *Immunity*, 28(3):285-287, (2008)).

NLRPs represent a subfamily of NLRs that include a Pyrin domain and are constituted by proteins such as NLRP1, NLRP3, NLRP4, NLRP6, NLRP7, and NLRP12. NLRPs are believed to be involved with the formation of multiprotein complexes termed inflammasomes (see, e.g., Chaput, C. et al., "NOD-like receptors in lung diseases," *Frontiers in Immunology*, 4: article 393, (2013)). These complexes typically include one or two NLR proteins, the adapter molecule apoptosis associated speck-like containing a CARD domain (ASC) and pro-caspase-1 F (see, e.g., Bauernfeind, F and Hornung, V. "Of inflammasomes and pathogens—sensing of microbes by the inflammasome," *EMBO Molecular Medicine*, 5(6):814-826, (2013)).

One such inflammasome is formed by the NLRP3 scaffold, the ASC adaptor and pro-caspase-1 (see, e.g., Hirota, J. A., et al., "The airway epithelium nucleotide-binding domain and leucine-rich repeat protein 3 inflammasome is activated by urban particulate matter," *Journal of Allergy and Clinical Immunology*, 129(4):1116.e6-1125.e6, (2012)), and its expression is believed to be induced by inflammatory cytokines and TLR agonists in myeloid cells and human bronchial epithelial cells (Id.). The NLRP3 inflammasome is believed to mediate the caspase-1-dependent conversion of pro-IL-1β and pro-IL-18 to IL-1β and IL-18. Further, IL-1β and IL-18 have potential in the treatment of various types of cancer (see, e.g., Chen, L-C. et al., *EMBO Mol Med.*, 4(12):1276-1293 (2012) and Tse, B. W-C. et al., *PLoS One*, 6(9): e24241 (2011)). IL-18 has been shown to override resistance to checkpoint inhibitors in colon cancer animal tumor models (see e.g., Ma, Z. et al., *Clin. Cancer Res.* January 11. (2016) DOI: 10.1158/1078-0432.CCR-15-1655).

SUMMARY

The invention is directed to compounds of Formula (I):

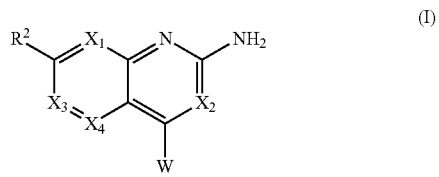

wherein all of the variables are as defined herein below.

Also within the scope of the invention are pharmaceutically acceptable salts, stereoisomers, tautomers, and solvates of the compounds of Formula (I).

The invention is also directed to pharmaceutical compositions comprising one or more compounds of the invention. The invention is also directed to methods of treating cancer using one or more compounds of the invention.

The invention also provides processes and intermediates for making the compounds of Formula (I) or pharmaceutically acceptable salts, stereoisomers, tautomers, and solvates thereof.

The compounds of the invention may be used in therapy.

The compounds of the invention may be used for the manufacture of a medicament for the treatment of cancer.

The compounds of the invention can be used alone, in combination with other compounds of the present invention, or in combination with one or more other agent(s).

Other features and advantages of the invention will be apparent from the following detailed description and claims.

DETAILED DESCRIPTION

Compounds of Invention

In a first aspect, the present invention provides, inter alia, a compound of Formula (I):

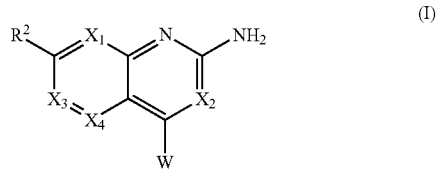

or a stereoisomer, a tautomer, or a pharmaceutically acceptable salt thereof, wherein:

W is independently selected from: $R^6$, —Y—$R^6$, -Q-$R^6$, and -Q-Y—$R^6$;

Q is independently selected from: $NR^5$, $CHR^5$, O, and S;

Y is independently selected from: $C_{1-10}$ alkylene, $C_{2-10}$ alkenylene, and $C_{2-10}$ alkynylene, each of which is substituted with 0 to 4 $R^a$ and/or each of which is optionally interrupted by one of the following: (i) O; or (ii) $N(R^b)$;

$X_1$ is independently N or $CR^1$;
$X_2$ is independently N or $CR^2$;
$X_3$ is independently N or $CR^3$;
$X_4$ is independently N or $CR^4$;

provided that no more than two of $X_1$, $X_3$ and $X_4$ are N;

$R^1$ and $R^3$ are, at each occurrence, independently selected from: H, halogen, cyano, $C_{1-4}$ alkyl, $C_{1-4}$ haloalkyl, $C_{1-4}$ alkoxy, and $C_{1-4}$ haloalkoxy;

$R^2$ and $R^4$ are, at each occurrence, independently selected from: H, halogen, cyano, $C_{1-4}$ alkyl, $C_{1-4}$ haloalkyl, $C_{1-4}$ alkoxy, $C_{1-4}$ haloalkoxy, $N(C_{1-4}$ alkyl$)_2$, and —($C_{0-3}$ alkylene)-heteroaryl including 5 ring atoms, wherein from 1 to 4 ring atoms are each independently selected from N, NH, N($C_{1-4}$ alkyl), O, and S, wherein the heteroaryl is substituted with 0 to 3 $R^d$;

$R^5$ is independently H or $C_{1-4}$ alkyl;

$R^6$ is independently a bicyclic or tricyclic cycloalkyl or cycloalkenyl ring including from 5 to 12 ring atoms, wherein the cycloalkyl or cycloalkenyl ring may be a spirocyclic ring or may contain one or two bridged linker(s) selected from —$CR^8R^9$—, —$(CR^8R^9)_2$—, and —$C(=O)$—; wherein the cycloalkyl or cycloalkenyl ring is substituted with 0 to 4 $R^e$;

alternatively, $R^6$ is independently a bicyclic or tricyclic heterocycloalkyl ring including from 5 to 12 ring atoms, wherein from 1 to 4 ring atoms are each independently selected from N, N($R^b$), O, and S, wherein the heterocycloalkyl ring may be a spirocyclic ring or contain a bridged linker selected from —$CR^8R^9$—, —O—, —$(CR^8R^9)_2$—, —$OCR^8R^9$—, and —$CR^8R^9O$—, and —$C(=O)$—; wherein the heterocycloalkyl ring is substituted with 0 to 4 $R^e$;

$R^7$ is independently a heteroaryl including 5 ring atoms, wherein from 1 to 4 ring atoms are each independently selected from N, NH, N($C_{1-4}$ alkyl), O, and S, wherein the heteroaryl is substituted with 0 to 3 $R^d$;

$R^8$ and $R^9$ are, at each occurrence, independently selected H, OH, halogen, $C_{1-4}$ alkyl and $C_{1-4}$ alkoxy;

$R^a$ is independently selected from: F, OH, cyano, $C_{1-4}$ alkoxy, $C_{1-4}$ haloalkyl, $C_{1-4}$ haloalkoxy, and $C_{1-4}$ alkyl substituted with 0 to 1 $R^e$;

$R^b$ is independently selected from: H, $C_{1-4}$ alkyl substituted with 0 to 1 OH, —$C(O)(C_{1-4}$ alkyl), and —$C(O)O(C_{1-4}$ alkyl);

$R^c$ is independently selected from: OH, $CONH_2$ and $C_{1-4}$ alkoxy;

$R^d$ is independently selected from: halogen, OH, cyano, $C_{1-4}$ alkoxy, $C_{1-4}$ alkoxy, $C_{1-4}$ haloalkyl, $C_{1-4}$ haloalkoxy, —$C(O)O(C_{1-4}$ alkyl), $NH_2$, $N(C_{1-4}$ alkyl$)_2$, —$C(O)NH_2$, —$C(O)N(C_{1-4}$ alkyl$)_2$, $C_{2-6}$ alkenyl, $C_{2-6}$ alkynyl, and $C_{1-6}$ alkyl substituted with 0 to 2 $R^a$; and $R^e$ is independently oxo or $R^d$.

In a second aspect, within the scope of the first aspect, wherein:

Q is independently selected from: NH, N($C_{1-4}$ alkyl), $CH_2$, and O;

Y is independently selected from: $C_{1-10}$ alkylene, $C_{2-6}$ alkenylene, and $C_{2-6}$ alkynylene, each of which is substituted with 0 to 4 $R^a$;

$R^2$ is independently selected from: H, halogen, cyano, $C_{1-4}$ alkyl, $C_{1-4}$ haloalkyl, $C_{1-4}$ alkoxy, and $C_{1-4}$ haloalkoxy;

$R^4$ is independently selected from: H, halogen, cyano, $C_{1-4}$ alkyl, $C_{1-4}$ haloalkyl, $C_{1-4}$ alkoxy, $C_{1-4}$ haloalkoxy, $N(C_{1-4}$ alkyl$)_2$, and 5-membered heteroaryl including from 1 to 2 ring atoms are each independently selected from N, NH, O, and S;

$R^6$ is independently a bicyclic or tricyclic cycloalkyl or cycloalkenyl ring including from 5 to 10 ring atoms, wherein said cycloalkyl or cycloalkenyl ring may be a spirocyclic ring or contain one or two bridged linker(s) selected from —$CH_2$— and —$CH_2CH_2$—; wherein the cycloalkyl or cycloalkenyl ring is substituted with 0 to 4 $R^e$;

alternatively, $R^6$ is independently a bicyclic heterocycloalkyl ring including from 5 to 10 ring atoms, wherein from 1 to 2 ring atoms are each independently selected from N, N($R^b$), O, and S, wherein the bicyclic ring may be a spirocyclic ring or contain a bridged linker selected from —$CH_2$—, —O—, —$CH_2CH_2$—, —$OCH_2$—, and —$CH_2O$—; wherein the heterocycloalkyl ring is substituted with 0 to 4 $R^e$;

$R^7$ is independently 5-membered heteroaryl including from 1 to 2 ring atoms are each independently selected from N, NH, O, and S; and $R^8$ and $R^9$ are, at each occurrence, independently H or $C_{1-4}$ alkyl.

In another aspect, within the scope of the first or second aspect, wherein:

$R^7$ is independently 5-membered heteroaryl including from 1 to 2 ring atoms are each independently selected from N, NH and S.

In another aspect, within the scope of the first or second aspect, wherein:

$R^2$, is independently selected from: H, halogen and $C_{1-4}$ alkyl;

$R^4$ is independently selected from: H, halogen, cyano, $C_{1-4}$ alkyl, $C_{1-4}$ haloalkyl, $C_{1-4}$ alkoxy, $C_{1-4}$ haloalkoxy, $N(C_{1-4}$ alkyl$)_2$, and heteroaryl selected from pyrazolyl, thienyl and isothiazolyl; and $R^7$ is independently pyrazolyl, thienyl or isothiazolyl.

In a third aspect, within the scope of the first or second aspect, the invention provides a compound of Formula (II):

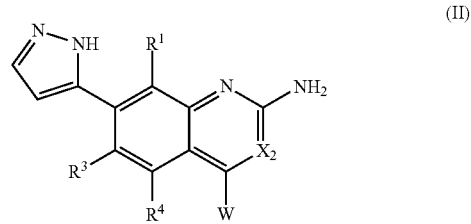

(II)

or a stereoisomer, a tautomer, or a pharmaceutically acceptable salt thereof, wherein:

W is independently $R^6$—NH—$R^6$, or —NH—$CH_2$—$R^6$;

$X_2$ is independently N or $CR^2$;

$R^1$, $R^2$, $R^3$ and $R^4$ are, at each occurrence, independently selected from: H, halogen and $C_{1-4}$ alkyl;

$R^6$ is independently a bicyclic or tricyclic cycloalkyl ring including from 5 to 10 ring atoms, wherein said cycloalkyl ring may be a spirocyclic ring or contain one or two bridged linker(s) selected from —$CH_2$— and —$CH_2CH_2$—; wherein the cycloalkyl ring is substituted with 0 to 2 $R^e$;

alternatively, $R^6$ is independently a bicyclic heterocycloalkyl ring including from 5 to 10 ring atoms, wherein from 1 to 2 ring atoms are each independently selected from N, N($R^b$), and O, wherein the bicyclic ring may be a spirocyclic ring or contain a bridged linker selected from —$CH_2$—, —O—, —$CH_2CH_2$—, —$OCH_2$—, and —$CH_2O$—; wherein the heterocycloalkyl ring is substituted with 0 to 2 $R^e$;

$R^b$ is independently selected from: H, $C_{1-4}$ alkyl, and —$C(O)O(C_{1-4}$ alkyl); and $R^e$ is independently selected from: oxo, halogen, cyano, OH, $CH_2OH$, $C_{1-4}$ alkoxy, $C_{1-4}$ haloalkyl, $N(C_{1-4}$ alkyl$)_2$, —$C(O)NH_2$, —$C(O)O(C_{1-4}$ alkyl), $C_{2-6}$ alkenyl, and $C_{1-4}$ alkyl substituted with 0 to 2 $C_{1-4}$ alkoxy.

In another aspect, within the scope of the third aspect, the invention provides a compound of Formula (II), or a stereoisomer, a tautomer, or a pharmaceutically acceptable salt thereof, wherein: W is independently $R^6$ or —NH—$R^6$.

In another aspect, within the scope of the third aspect, wherein: $R^e$ is independently selected from: oxo, halogen, cyano, OH, $CH_2OH$, $C_{1-4}$ alkoxy, $C_{1-4}$ haloalkyl, $N(C_{1-4}$ alkyl$)_2$, —$C(O)NH_2$, $C_{2-6}$ alkenyl, and $C_{1-4}$ alkyl substituted with 0 to 2 $C_{1-4}$ alkoxy.

In another aspect, within the scope of the third aspect, wherein: $R^e$ is independently selected from: oxo, OH, $CH_2OH$, $C_{1-4}$ alkoxy, —$C(O)NH_2$, $C_{2-6}$ alkenyl, and $C_{1-4}$ alkyl substituted with 0 to 2 $C_{1-4}$ alkoxy.

In a fourth aspect, within the scope of the third aspect, the invention provides a compound of Formula (II), or a stereoisomer, a tautomer, or a pharmaceutically acceptable salt thereof, wherein:

W is independently selected from: —NH—$R^6$, —NH—$CH_2$—$R^6$,

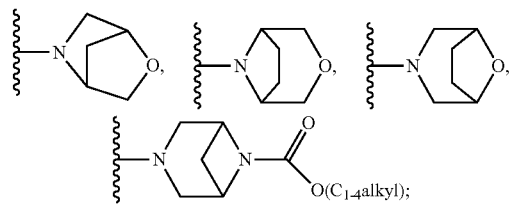

and
$R^6$ is independently selected from:

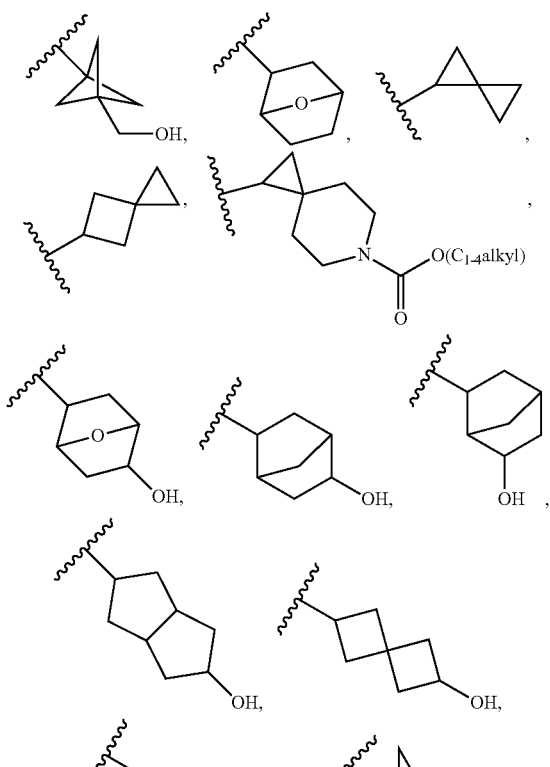

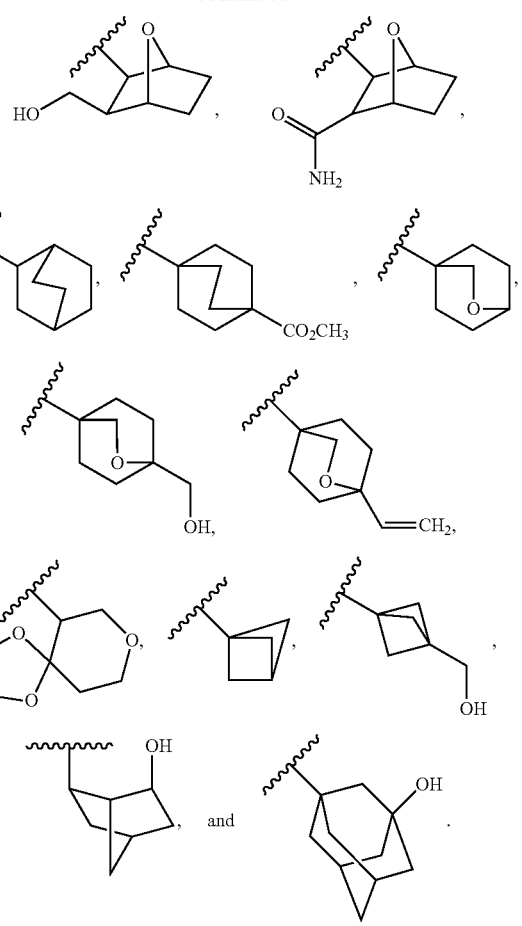

In another aspect, within the scope of the third aspect, the invention provides a compound of Formula (II), or a stereoisomer, a tautomer, or a pharmaceutically acceptable salt thereof, wherein:

W is independently selected from: —NH—$R^6$,

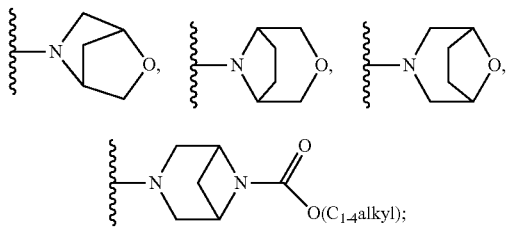

and
$R^6$ is independently selected from:

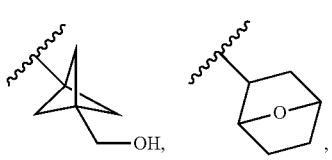

-continued

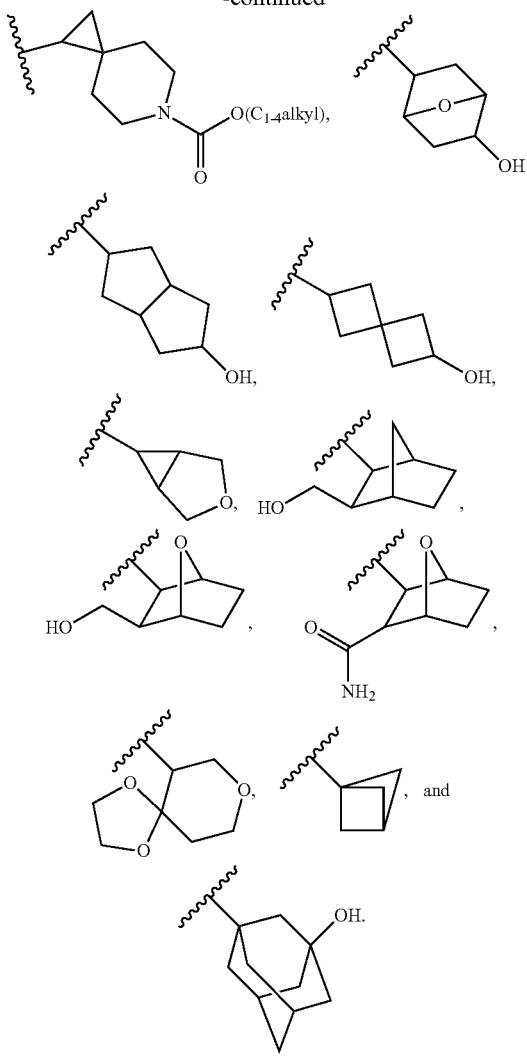

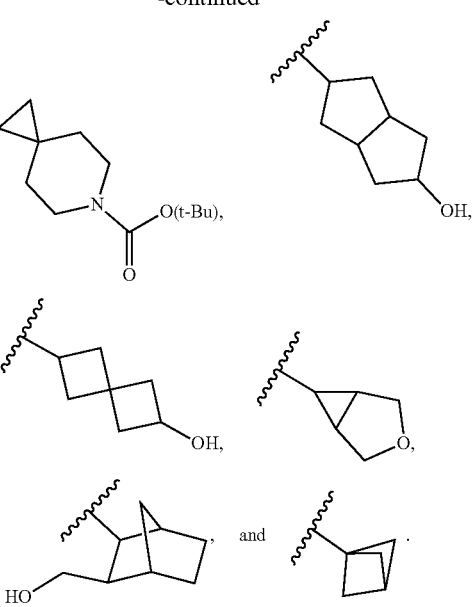

In a sixth aspect, within the scope of any of the first to fourth aspects, the invention provides a compound of Formula (III):

$$\text{(III)}$$

or a stereoisomer, a tautomer, or a pharmaceutically acceptable salt thereof, wherein:

X$_2$ is independently N or CR$^2$;

R$^1$, R$^2$, R$^3$ and R$^4$ are, at each occurrence, independently selected from: H, halogen and C$_{1-4}$ alkyl;

R$^6$ is independently a bicyclic or tricyclic cycloalkyl ring including from 5 to 10 ring atoms, wherein said cycloalkyl ring may be a spirocyclic ring or contain one or two bridged linker(s) selected from —CH$_2$— and —CH$_2$CH$_2$—; wherein the cycloalkyl ring is substituted with 0 to 2 R$^e$;

alternatively, R$^6$ is independently a bicyclic heterocycloalkyl ring including from 5 to 10 ring atoms, wherein from 1 to 2 ring atoms are each independently selected from N and O, wherein the bicyclic ring may be a spirocyclic ring or contain a bridged linker selected from —CH$_2$—, —O—, and —CH$_2$CH$_2$—; wherein the heterocycloalkyl ring is substituted with 0 to 2 R$^e$; and R$^e$ is independently selected from: oxo, OH, CH$_2$OH, C$_{1-4}$ alkoxy, and C$_{1-4}$ alkyl substituted with 0 to 2 C$_{1-4}$ alkoxy.

In a fifth aspect, within the scope of the third or fourth aspect, the invention provides a compound of Formula (II), or a stereoisomer, a tautomer, or a pharmaceutically acceptable salt thereof, wherein:

W is independently selected from: —NH—R$^6$,

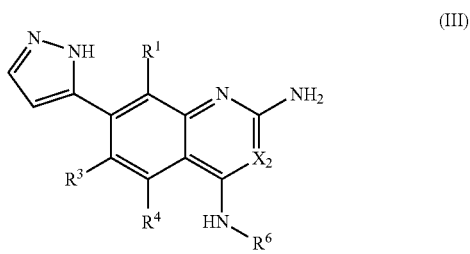

and

R$^6$ is independently selected from:

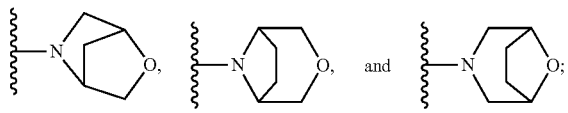

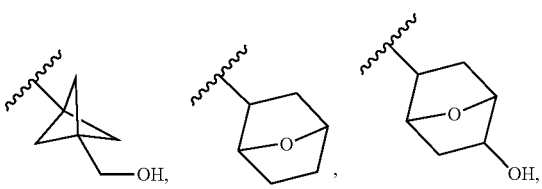

In a seventh aspect, within the scope of the sixth aspect, wherein:

X₂ is independently N or CH;

R¹, R³ and R⁴ are H; and

R⁶ is independently selected from:

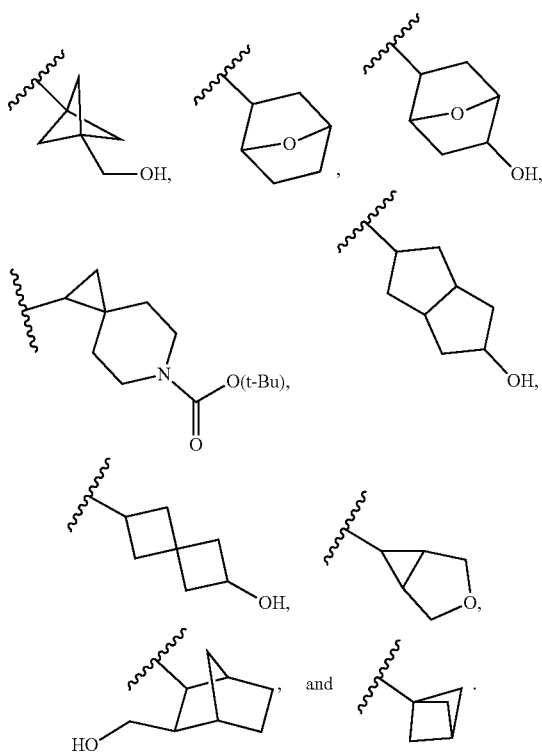

In another aspect, within the scope of the sixth aspect, wherein:

R⁶ is independently

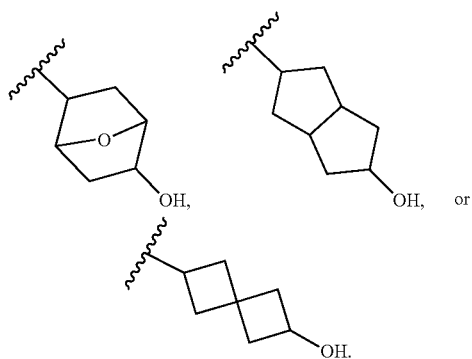

In another aspect, the invention provides a compound selected from the exemplified Examples 1 to 52 or a stereoisomer, a tautomer, or a pharmaceutically acceptable salt thereof.

In another aspect, the present invention provides a compound selected from any subset list of compounds or a single compound from the exemplified examples within the scope of any of the above aspects.

In some embodiments, R² is independently pyrazolyl, thienyl or isothiazolyl. In other embodiments, R² is pyrazolyl. In other embodiments, R² is thienyl. In other embodiments, R² is isothiazolyl.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

OTHER ASPECTS AND EMBODIMENTS OF THE INVENTION

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). In preferred embodiments, methods for modulating NLRP3 activity are agonizing and partially agonizing. In certain embodiments, methods for modulating NLRP3 activity are agonizing. In certain embodiments, methods for modulating NLRP3 activity are partially agonizing. Methods include in vitro methods, e.g., contacting a sample that includes one or more cells comprising NLRP3 (e.g., THP-1 cells) with the chemical entity. Methods can also include in vivo methods; e.g., administering the chemical entity to a subject (e.g., a human) having a disease in which an increase in NLRP3 signaling may correct a deficiency in innate immune activity that contributes to the pathology and/or symptoms and/or progression of the disease (e.g., cancer; e.g., a refractory cancer).

In some embodiments, compounds of the invention are useful for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human).

A cancer is said to be refractory when it does not respond to (or is resistant to) cancer treatment. Refractory cancer is also known as resistant cancer.

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same). In some embodiments, the cancer may be a refractory cancer.

In a further aspect, methods of treatment of a disease in which an increase in NLRP3 signaling may correct a deficiency in innate immune activity that contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which an increase in NLRP3 signaling may correct a deficiency in innate immune activity that contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which an increase in NLRP3 signaling may correct a deficiency in innate immune activity that contributes to the pathology and/or symptoms and/or progression of the disease, thereby treating the disease.

Embodiments can include one or more of the following features.

The chemical entity can be administered in combination with one or more additional cancer therapies (e.g., surgery, radiotherapy, chemotherapy, toxin therapy, immunotherapy, cryotherapy or gene therapy, or a combination thereof, e.g., cancer therapies that include administering one or more (e.g., two, three, four, five, six, or more) additional anti-cancer agents. Non-limiting examples of additional anti-cancer agents (chemotherapeutic agents) are selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a *vinca* alkaloid and/or a taxane; e.g., Vincristine, Vinblastine, Vinorelbine and/or Vindesine, Taxol, Paclitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Brentuximab vedotin, Canakinumab, Cetuximab, Certolizumab pegol, Daclizumab, Denosumab, Eculizumab, Efalizumab, Gemtuzumab, Golimumab, Ibritumomab tiuxetan, Infliximab, Ipilimumab, Muromonab-CD3, Natalizumab, Ofatumumab, Omalizumab, Palivizumab, Panitumumab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12.

The subject can have cancer; e.g., the subject has undergone and/or is undergoing and/or will undergo one or more cancer therapies.

Non-limiting examples of cancer include acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In other embodiments, the mammal has been identified as having a cancer or an infectious disease. Representative infectious diseases include, without limitation, Acinobacter infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black *piedra, Blastocystic hominis* infection, blastomycosis, Bolivian hemorrhagic fever, botulism, Brazilian hemorrhagic fever, brucellosis, bubonic plaque, Burkholderi infection, Buruli ulcer, Calicivirus infection, camptobacteriosis, candidiasis, cat-scratch disease, cellulitis, Chagas disease, chancroid, chickenpox, chikungunya, *chlamydia*, Chlamydophilapneumoniae infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, Desmodesmus infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium* myonecrosis, free-living amebic infection, *Fusobacterium* infection, gas gangrene, geotrichosis, Gerstmann-Straussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, Heliobacter *pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human *ewingii* ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, *mycoplasma* pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, *salmonellosis*, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, tinea barabe, tinea capitis, tinea corporis, tinea cruris, tinea manum, tinea nigra, tinea pedis, tinea unguium, tinea *versicolor*, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white *piedra*, *Yersinia* psuedotuberculosis infection, yersiniosis, yellow fever, and zygomycosis.

The chemical entity can be administered intratumorally.

The chemical entity can be administered systemically (including but not limited to orally, subcutaneously, intramuscular, intravenously).

The methods can further include identifying the subject.

Other embodiments include those described in the Detailed Description and/or in the claims.

Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —OCH$_3$ is attached through the oxygen atom.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

An "agonist" of NLRP3 includes compounds that, at the protein level, directly bind or modify NLRP3 such that an activity of NLRP3 is increased, e.g., by activation, stabilization, altered distribution, or otherwise.

Certain compounds described herein that agonize NLRP3 to a lesser extent than a NLRP3 full agonist can function in assays as antagonists as well as agonists. These compounds antagonize activation of NLRP3 by a NLRP3 full agonist because they prevent the full effect of NLRP3 interaction. However, the compounds also, on their own, activate some NLRP3 activity, typically less than a corresponding amount of the NLRP3 full agonist. Such compounds may be referred to as "partial agonists of NLRP3".

In some embodiments, the compounds described herein are agonists (e.g. full agonists) of NLRP3. In other embodiments, the compounds described herein are partial agonists of NLRP3.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof, e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 22nd Edition, Pharmaceutical Press, London, U K (2012); *Handbook of Pharmaceutical Excipients*, 6th ed.; Rowe et al., Eds.; The Pharmaceutical Press and the American Pharmaceutical Association: (2009); *Handbook of Pharmaceutical Additives*, 3rd ed.; Ash and Ash Eds.; Gower Publishing Company: (2007); *Pharmaceutical Preformulation and Formulation*, 2nd ed.; Gibson Ed.; CRC Press LLC: Boca Raton, FL, (2009).

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" or "halogen" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "alkylene" refers to a branched or unbranched divalent alkyl (e.g., —$CH_2$—).

The term "haloalkyl" refers to an alkyl, in which one or more hydrogen atoms is/are replaced with an independently selected halo.

The term "alkoxy" refers to an —O-alkyl radical (e.g., —$OCH_3$).

The term "haloalkoxy" refers to an —O-haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy.

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aromatic" refers generally to a ring that includes a cyclic array of resonance-stabilized 4n+2 pi electrons, wherein n is an integer (e.g., 1 or 2). Aromatic moieties include aryl and heteroaryl groups. The term "non-aromatic" describes any moiety that does not fall within the definition of "aromatic".

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 5 to 12 carbons, preferably bicyclic or tricyclic and 5 to 10 carbons, wherein the cycloalkyl group may be a spirocyclic ring or contain one or more bridged linker(s), and may be optionally substituted. The term "cycloalkylene" as used herein refers to divalent cycloalkyl.

The term "heterocycloalkyl" as used herein includes saturated cyclic hydrocarbon groups having 5 to 12 ring atoms, preferably bicyclic 5 to 10 ring atoms, including from 1 to 4 ring atoms are each independently selected from N (or substituted N), O, and S, wherein the heterocycloalkyl may be a spirocyclic ring or contain a bridged linker, and may be optionally substituted. The term "heterocycloalkylene" as used herein refers to divalent heterocycloalkyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the accompanying drawings and the description below. Other features and advantages of the invention will be apparent from the description and drawings, and from the claims.

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) in a subject (e.g., a human). This disclosure also features compositions as well as other methods of using and making the same.

Pharmaceutical Compositions and Administration

In some embodiments, a chemical entity (e.g., a compound that modulates (e.g., agonizes or partially agonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, a pharmaceutical composition comprising a compound of the present invention or a salt thereof, and one or more pharmaceutically acceptable excipients. In certain embodiments, a pharmaceutical composition comprising a compound of the present invention or a pharmaceutically acceptable salt thereof, and one or more pharmaceutically acceptable excipients. In certain embodiments, a pharmaceutical composition comprising a therapeutically effective amount of a compound of the present invention or a pharmaceutically acceptable salt thereof, and one or more pharmaceutically acceptable excipients.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral). In certain embodiments, a preferred route of administration is systemic.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" *Neoplasia.* 10:788-795 (2006).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEGs, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 1 mg/kg; from about 0.1 mg/kg to about 0.5 mg/kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

Indications

In any of the methods described herein, the subject can have a cancer. In some examples of any of the methods described herein, the mammal has been identified as having a cancer, or has been diagnosed as having a cancer.

Non-limiting examples of cancer include: acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In certain embodiments, non-limiting examples of cancer include: breast cancer, colon cancer, rectal cancer, colorectal cancer, pancreatic cancer, and prostate cancer.

Methods for diagnosing a subject as having a cancer or identifying a mammal as having a cancer are well known in the art. For example, a medical professional (e.g., a physician, a physician's assistant, or a technician) can diagnose cancer in a mammal by observing one or more symptoms of cancer in a mammal. Non-limiting examples of symptoms of cancer include: fatigue, lump or area of thickening felt under the skin, weight change, jaundice, darkening or redness of the skin, sores that won't heal, changes to existing moles, changes in bowel or bladder habits, persistent cough or trouble breathing, difficulty swallowing, hoarseness, persistent indigestion or discomfort after eating, persistent, unexplained muscle or joint pain, persistent, unexplained fevers or night sweats, and unexplained bleeding or bruising. Methods of diagnosing a subject as having a cancer or identifying a subject as having a cancer can further include performing one or more diagnostic tests (e.g., performing one or more diagnostic tests on a biopsy or a blood sample).

In some examples of any of the methods described herein, a subject can be a subject having a cancer, a subject diagnosed as having a cancer, or a subject identified as having a cancer that has been unresponsive to a previously administered treatment for cancer. Diagnostic tests for diagnosing a subject as having a cancer or identifying a mammal as having a cancer are known in the art.

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

In some embodiments, the present invention provides a method of treating cancer, wherein the cancer can be any cancer that does not elicit an optimal innate immune system response.

Innate immune system refers to a part of the immune system consisting of cells that react to threats for the organism like infections or cancer in an antigen-non-specific way and stimulate the adaptive, antigen-specific immune system. In general, complete removal of the threat and long-lasting protection (=immunity) requires activity of the adaptive, antigen-specific immune system that in turn depends on stimulation by the innate immune system.

In some embodiments, the present invention provides a method of treating case, the cancer is selected based on resistance to T-cell checkpoint inhibition, either independent of cancer type and based on failure to respond to previous T-cell checkpoint inhibitor therapy or based on cancer type that is generally resistant to T-cell checkpoint inhibitor therapy such as hormone receptor positive breast cancer, microsatellite stable colon or rectal cancer, pancreatic cancer and prostate cancer.

In certain other embodiments, the present invention provides a method of treating cancer comprising an NLPR3 agonist of the present invention to treat non-inflamed tumors with low CD8+ T-cell infiltration to enhance tumor immunogenicity and promote inflammatory responses. For example, the combination may be used to treat a solid tumor based on results of a biopsy that demonstrated low CD8+ T-cell infiltration or low expression of genes produced by CD8+ T-cells.

Resistance to T-cell checkpoint inhibition refers to cancer progression on therapy or lack of response within 6 months of therapy according to consensus response criteria for the respective cancer, such as RECIST1.1 for most solid tumors.

T-cell infiltration refers to percent of T-cells of all nucleated cells by immunohistochemistry of tumor biopsy specimens.

CD8+ T-cell infiltration refers to percent of CD8+ cells of all nucleated cells by immunohistochemistry of tumor biopsy specimens.

In addition to immunohistochemistry for quantifying CD8+ T-cells in biopsy specimens, expression of genes produced by CD8+ T-cells like interferon-γ can be measured by quantifying mRNA using for example next generation sequencing and inform about CD8+ T-cell infiltration. Thresholds for low and high CD8+ T-cell infiltration by immunohistochemistry of mRNA quantifying techniques are being developed by various groups and take the spectrum of CD8+ T-cell infiltration across cancers as well as for specific cancers into account.

In any of the methods described herein, the subject can have an infectious disease. In some examples of any of the methods described herein, the subject has been identified as having an infectious disease, or has been diagnosed as having an infectious disease. For example, an infectious disease can be caused by a bacterium, virus, fungus, parasite, or a mycobacterium.

Non-limiting examples of infectious disease include: Acinobacter infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black *piedra, Blastocystic hominis* infection, blastomycosis, Bolivian hemorrhagic fever, botulism, Brazilian hemorrhagic fever, brucellosis, bubonic plaque, Burkholderi infection, Buruli ulcer, Calicivirus infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, Desmodesmus infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolpsiasis, fasciolosis, fatal familial insomnia, filariasis, food poisoning by *Clostridium* myonecrosis, free-living amebic infection, *Fusobacterium* infection, gas gangrene, geotrichosis, Gerstmann-Straussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human *ewingii* ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, tinea barabe, tinea capitis, tinea corporis, tinea cruris, tinea manum, tinea nigra, tinea pedis, tinea unguium, tinea versicolor, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white *piedra, Yersinia* psuedotuberculosis infection, yersiniosis, yellow fever, and zygomycosis.

Methods for diagnosing a subject as having an infectious disease, or identifying a subject as having an infectious disease are well known in the art. For example, a medical professional (e.g., a physician, a physician's assistant, or a technician) can diagnose infectious disease in a subject by observing one or more symptoms of infectious disease in a subject. Non-limiting examples of symptoms of infectious disease include: fever, diarrhea, fatigue, and muscle aches. Methods of diagnosing a mammal as having an infectious disease or identifying a subject as having an infectious disease can further include performing one or more diagnostic tests (e.g., performing one or more diagnostic tests on a biopsy or a blood sample). Diagnostic tests for diagnosing a subject as having an infectious disease or identifying a subject as having an infectious disease are known in the art.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional cancer therapy comprises (chemotherapeutic agent) an immunomodulatory moiety, e.g., an immune checkpoint inhibitor. In certain of these embodiments, the immune checkpoint inhibitor targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9—TIM3, Phosphatidylserine—TIM3, lymphocyte activation gene 3 protein (LAG3), MHC class II—LAG3, 4-1BB-4-1BB ligand, OX40-OX40 ligand, GITR, GITR ligand—GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine—TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12. See, e.g., Postow, M. *J. Clin. Oncol.* 33, 1 (2015).

In certain embodiments, the immune checkpoint inhibitor targets an immune checkpoint receptor selected from CTLA-4, PD-1, PD-L1, PD-1-PD-L1, and PD-1-PD-L2.

In certain embodiments, the immune checkpoint inhibitor is selected from: nivolumab (also known as "OPDIVO"; formerly designated 5C4, BMS-936558, MDX-1106, or ONO-4538), pembrolizumab (also known as "KEYTRUDA", lambrolizumab, and MK-3475. See WO 2008/156712), PDR001 (Novartis; see WO 2015/112900), MEDI-0680 (AstraZeneca; AMP-514; see WO 2012/145493), cemiplimab (REGN-2810) (Regeneron; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (SHR-1210; Jiangsu Hengrui Medicine; see WO 2015/085847; Si-Yang Liu et al., *J Hematol. Oncol.* 10:136 (2017)), TSR-042 (ANBO11; Tesaro Biopharmaceutical; see WO2014/179664), GLS-010 (WBP3055; Wuxi/Harbin Gloria Pharmaceuticals; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGD013 (Macrogenics); IB1308 (Innovent; see WO 2017/024465, WO 2017/025016, WO 2017/132825, WO2017/133540); BMS-936559 (formerly 12A4 or MDX-1105; see, e.g., U.S. Pat. No. 7,943,743 and WO 2013/173223), MPDL3280A (also known as RG7446, atezolizumab, and TECENTRIQ; U.S. Pat. No. 8,217,149; see, also, Herbst et al. (2013) J Clin Oncol 31(suppl):3000), durvalumab (IMFINZI; MEDI-4736; AstraZeneca; see WO 2011/066389), avelumab (Pfizer; MSB-0010718C; BAVENCIO; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g, WO 2017/034916), CK-301 (Checkpoint Therapeutics; see Gorelik et al., AACR:Abstract 4606 (April 2016)); urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab (YERVOY; U.S. Pat. No. 6,984, 720), MK-1308 (Merck), AGEN-1884 (Agenus Inc.; WO 2016/196237), and tremelimumab (formerly ticilimumab, CP-675,206; AstraZeneca; see, e.g., WO 2000/037504 and Ribas, *Update Cancer Ther.* 2(3): 133-39 (2007)).

In certain embodiments, the immune checkpoint inhibitor is selected from: nivolumab, pembrolizumab, JS001, BGB-A317, INCSHR1210, TSR-042, GLS-010, STI-1110, MGD013, IBI308, BMS-936559, atezolizumab, durvalumab, avelumab, STI-1014, CX-072, KN035, LY3300054, CK-301, urelumab, PF-05082566, MEDI6469, TRX518, varlilumab, BMS-986016, ipilimumab, AGEN-1884, and tremelimumab.

In certain of these embodiments, the immune checkpoint inhibitor is selected from: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, bevacizumab, and MNRP1685A.

In certain embodiments, the immune checkpoint inhibitor is selected from: nivolumab, ipilimumab, pembrolizumab, atezolizumab, durvalumab and avelumab.

In certain embodiments, the immune checkpoint inhibitor is selected from: nivolumab and ipilimumab.

In certain embodiments, the additional anti-cancer agent (chemotherapeutic agent) is a STING agonist. For example, the STING agonist can include cyclic di-nucleotides, such as cAMP, cGMP, and cGAMP as well as modified cyclic di-nucleotides that include one or more of the following modification features (2'-O/3'-O linkage, phosphorothioate linkage, adenine and/or guanine analogue, 2'-OH modification (e.g., —OCH$_3$ or replacement, e.g., —F or N$_3$). See, e.g., WO 2014/189805.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semi-synthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an antimetabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a vinca alkaloid, a podophyllotoxin and/or a taxane. Vinca alkaloids, in general, bind to specific sites on tubulin, inhibiting the assembly of tubulin into microtubules, generally during the M phase of the cell cycle. In an embodiment, a vinca alkaloid is derived, without limitation, from the Madagascar periwinkle, *Catharanthus roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited, to Taxol, Paclitaxel and/or Docetaxel. In a further embodiment a plant alkaloid or terpernoid is a synthetic, semisynthetic or derivative. In a further embodiment, a podophyllotoxin is, without limitation, an etoposide and/or teniposide. In an embodiment, a taxane is, without limitation, docetaxel and/or ortataxel. In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613.

In yet another embodiment, the methods can further include administering one or both of: (i) one or more anti-fungal agents (e.g., selected from the group of bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and balsam of peru) and (ii) one or more antibiotics (e.g., selected from the group of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, amoxicillin, calvulanate, ampicillin, subbactam, piperacillin, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanilimide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and teixobactin).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the NLRP3 protein can serve as a biomarker for certain types of cancer.

In some embodiments, the chemical entities, methods, and compositions described herein can be administered to certain treatment-resistant patient populations (e.g., patients resistant to checkpoint inhibitors).

In some embodiments, the compounds of the present invention may be used in therapy. In certain embodiments, the present invention provides a combined preparation of a compound of the present invention, or a pharmaceutically acceptable salt thereof, and additional therapeutic agent(s) for simultaneous, separate or sequential use in therapy.

In some embodiments, a compound of the present invention, or a pharmaceutically acceptable salt thereof, or a pharmaceutical composition containing the same, may be used as a medicament. In certain embodiments, the compounds of the invention may be used for the manufacture of a medicament for the treatment of cancer. In certain embodiments, the compounds of the invention may be used for the manufacture of a medicament for modulating NLRP3 activity. In certain embodiments, the modulating comprises agonizing NLRP3.

Methods of Preparation

As can be appreciated by the skilled artisan, methods of synthesizing the compounds of the formulae herein will be evident to those of ordinary skill in the art. For example, the compounds described herein can be synthesized, e.g., using one or more of the methods described herein and/or using methods described in, e.g., US 2015/0056224. Synthetic chemistry transformations and protecting group methodologies (protection and deprotection) useful in synthesizing the compounds described herein are known in the art and include, for example, those such as described in Larock, R. C., *Comprehensive Organic Transformations*, $2^{nd}$ Edition, Wiley-VCH, New York, NY (1999); Wuts, P. G. M., *Greene's Protective Groups in Organic Synthesis*, 5th Edition, Wiley (2014); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1H$ NMR, heteronuclear NMR, mass spectrometry, liquid chromatography, and infrared spectroscopy. The foregoing list is a subset of characterization methods available to a skilled artisan and is not intended to be limiting.

The following abbreviations have the indicated meanings:
ACN=acetonitrile
AcOH=acetic acid
BOP=(Benzotriazol-1-yloxy)tris(dimethylamino)phosphonium hexafluorophosphate
$CDCl_3$=chloroform-d
$CD_3OD$=methanol-$d_4$
$CH_2Cl_2$=dichloromethane
$CH_3ReO_3$=methyltrioxorhenium
$Cs_2CO_3$=cesium carbonate
CuI=copper (I) iodide
d=doublet
DBU=1,8-diazabicycloundec-7-ene
DCM=dichloromethane
DIEA=N,N-diisopropylethylamine
DMF=N,N-dimethylformamide
DMSO=dimethylsulfoxide
ES=electrospray ionization
$Et_2O$=diethyl ether
EtOAc=ethyl acetate
EtOH=ethanol
equiv=equivalents
g=gram(s)
h=hour(s)

HCl=hydrogen chloride (usually as a solution)
H$_2$O=water
H$_2$O$_2$=hydrogen peroxide
HATU=1-[Bis(dimethylamino)methylene]-1H-1,2,3-triazolo[4,5-b]pyridinium 3-oxide hexafluorophosphate
HPLC=high-performance liquid chromatography
Hunig's base=N,N-Diisopropylethylamine
I$_2$=iodine
K$_2$CO$_3$=potassium carbonate
K$_2$HPO$_4$=potassium phosphate, dibasic
KI=potassium iodide
kg=kilogram(s)
LC/MS=liquid chromatography mass spectrometer
LiBH$_4$=lithium borohydride
m=multiplet
m/z=mass to charge ratio
M=molar
m-CPBA=meta-chloroperoxybenzoic acid
mg=milligram(s)
MeOH=methanol
MHz=megahertz
mL=milliliter(s)
mmol=millimole(s)
min=minute(s)
NaHCO$_3$=sodium bicarbonate
Na$_2$CO$_3$=sodium carbonate
NaOH=sodium hydroxide
Na$_2$SO$_4$=sodium sulfate
NEt$_3$ and TEA=triethylamine
NH$_4$OH or NH$_3$H$_2$O=ammonium hydroxide
NH$_4$HCO$_3$=ammonium bicarbonate
nm=nanometer
PdCl$_2$(PPh$_3$)$_2$=bis(triphenylphosphine)palladium (II) dichloride
Pd(dppf)Cl$_2$=[1,1'-Bis(diphenylphosphino)ferrocene]dichloropalladium(II)
Pd(dppf)Cl$_2$DCM=[1,1'-Bis(diphenylphosphino)ferrocene]dichloropalladium(II) dichloromethane complex
Pd(OH)$_2$=palladium hydroxide
PMB=para-methoxybenzyl
POCl$_3$=phosphorous oxychloride
ppm=parts per million
Pt=platinum
Pt/C=platinum on carbon
s=singlet
t=triplet
T3P=n-propylphosphonic anhydride
TFA=trifluoroacetic acid
TLC=thin layer chromatography
TsCl=para-toluenesulfonyl chloride
° C.=degrees Celsius
μmol=micromole(s)

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention.

The compounds of this invention may be prepared using the reactions and techniques described in this section and the accompanying Schemes.

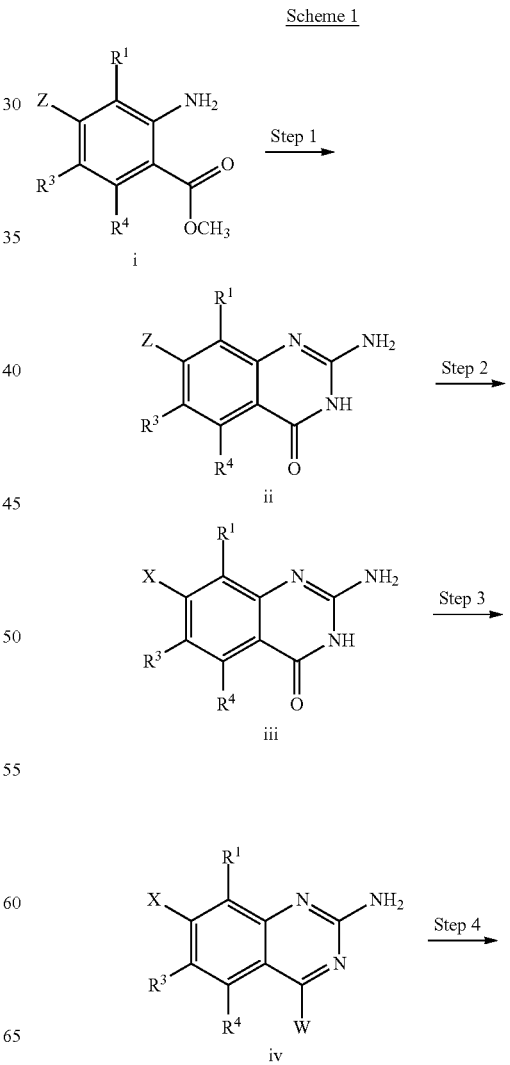

Scheme 1

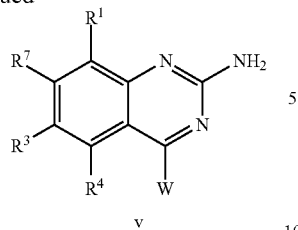

v

Step 1: The first step of begins with a suitably functionalized aminobenzoate (i). If desired, the group Z may be the group R⁷ found in the final product. Alternatively, the group Z may be a group that can be transformed into the group R⁷ found in the final product, such as bromo. This aminobenzoate may be available commercially or synthesized by methods known to one skilled in the art. In step 1, aminobenzoate (i) is reacted with a reagent or combination of reagents to transform it into aminoquinazolinone (ii), such as cyanamide and hydrochloric acid, in a suitable solvent, such as dioxane.

Step 2: In this optional step, the group Z present in (ii) may be transformed into a different group X. This group X may be the group R⁷ present in the final product, if desired. Alternatively, group X may be a group that can be transformed into group R⁷ at a later stage. One skilled in the art will recognize that the conditions selected for step 2 will depend on the identities of the groups X and Z. For example, if group Z is bromo, and the group X is a heteroaryl ring, this transformation may be effected by reaction with a suitable boronic acid or boronic ester in the presence of a catalyst such as PdCl$_2$(dppf), and base such as cesium carbonate in a solvent mixture such as dioxane and water.

Step 3: In step 3, the quinazolone (iii) is reacted with an appropriate set of reagents to install the group W found in the final molecule. For example, if the desired group W is an amine, this transformation may be effected by reacting (iii) with the desired amine, a reagent such as BOP, and a base such as DBU. Depending on the identity of the desired group W, additional reactions may be performed at this point. For example, if the installed group contains an alkene and the desired group W contains a diol, this transformation may be accomplished by reaction with a reagent such as osmium tetroxide and an oxidant such as NMO.

Step 4: In this optional step, if the group X in (iv) is not the desired group R⁷ in the final molecule (v), it may be transformed into R² under suitable conditions. For example, if the desired group R⁷ is 3-pyrazoyl and the group X is a pyrazole protected by a tetrahydropyran group, the protecting group may be removed by a suitable combination of acid and solvent, such as HCl and methanol, or TFA and DCM.

Further aspects of this invention may be prepared as summarized in Scheme 2.

Scheme 2

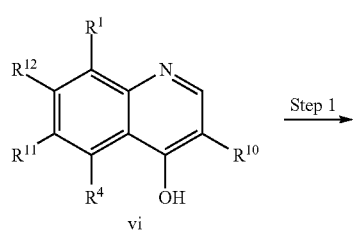

vi

Step 1

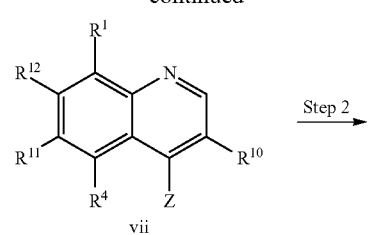

vii

Step 2

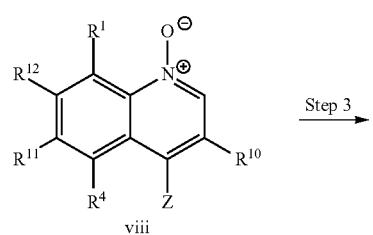

viii

Step 3

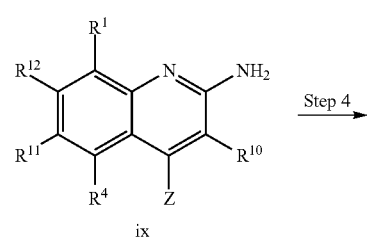

ix

Step 4

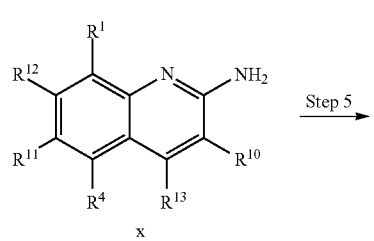

x

Step 5

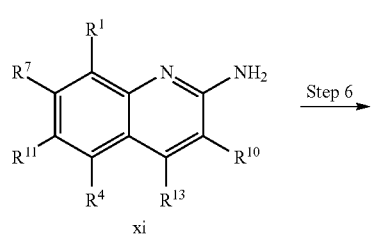

xi

Step 6

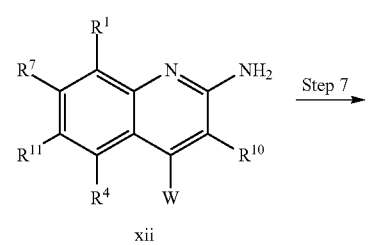

xii

Step 7

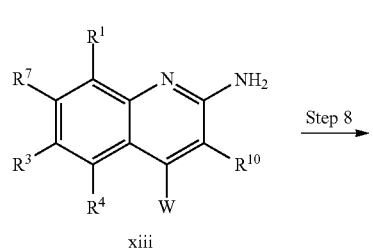

xiii

Step 8

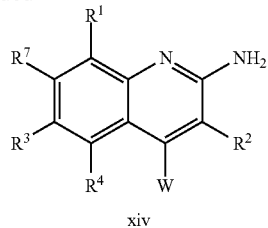

Step 1: The first step of Scheme 2 begins with a suitably functionalized quinolinol (vi). If desired, the groups $R^{10}$, $R^{11}$ and $R^{12}$ may be the groups $R^2$, $R^3$ and $R^7$, found in the final product. Alternatively, one or more of these groups may be groups that can be modified at a later stage of the synthesis, such as bromo. This quinolinol may be purchased commercially, or may be synthesized by methods known to one skilled in the art. In step 1, the alcohol group of compound (vi) may be transformed into a halogen group or sulfonate ester, such as chloro, bromo, or triflate. If the desired group Z is chloro, this transformation may be effected by treating compound (vi) with a reagent such as phosphoryl chloride in a solvent such as toluene. Alternatively, if the desired group Z is bromo, this transformation may be effected by treating compound (vi) with a reagent such as phosphorous tribromide in a solvent such as DMF. Alternatively, if the desired group Z is triflate, this transformation may be effected by treating compound (vi) with a reagent such as trifluoromethanesulfonyl chloride, a reagent such as 4-dimethylaminopyridine, and a base such as Hunig's base in a solvent such as dichloromethane.

Step 2: In step 2 of Scheme 2, compound (vii) is transformed into N-oxide (viii) by treatment with an appropriate oxidant, such as meta-chloroperoxybenzoic acid, in a solvent such as DCM.

Step 3: In step 3 of Scheme 1, compound (viii) is transformed into amine (ix) by treatment with an appropriate activating reagent, such as tosyl chloride, and a source of ammonia, such as ammonium chloride and triethylamine, in an appropriate solvent, such as DCM.

Step 4: In step 4 of Scheme 2, the Z group of compound (ix) is transformed into group $R^{13}$ of compound (x). The group $R^{13}$ may be the group W desired in the final compound; alternatively, it may be a group that can be transformed into group W at a later stage of the synthesis. One skilled in the art will recognize that the means to effect this transformation will depend on the nature of the groups $R^{13}$ and Z. For example, if Z is chloro and the desired group $R^{13}$ is an amine, this transformation may be effected by heating compound (ix) to a suitable temperature, such as 120° C. with an appropriate amine and a base such as Hunig's base in a solvent such as DMSO. Alternatively, if Z is chloro and the desired group $R^{13}$ is an ether, this transformation may be effected by heating compound (ix) to a suitable temperature, such as 100° C. with an appropriate alcohol and a base such as potassium tert-butoxide in a solvent such as NMP. Alternatively, if Z is bromo and the desired group $R^9$ is an alkyne, this transformation may be effected by heating compound (ix) to a suitable temperature, such as 70° C., with an appropriate alkyne, copper (I) iodide, an appropriate base, such as Hunig's base, and a suitable palladium source, such as tetrakis(triphenylphosphine)palladium(0), in a suitable solvent, such as THF. Alternatively, if Z is a triflate and the desired group $R^{13}$ is a optionally substituted alkyl group, this step may be accomplished by treating compound (ix) with an appropriate alkyl boronic acid or ester, a catalyst such as $PdCl_2(dppf)$-DCM complex, and a base such as cesium carbonate in a solvent such as dioxane.

Steps 5 through 8 of Scheme 2 consist of a series of optional functional group manipulations to convert the substituents $R^{10}$, $R^{11}$, $R^{12}$, and $R^{13}$ in intermediate (x) to the substituents $R^2$, $R^3$, $R^7$ and W desired in the final compound (xiv). One skilled in the art will recognize that some or all of these steps may not be necessary depending on the groups found in compounds (x) and (xiv). One skilled in the art will also recognize that, for some substrates, these steps may be performed in alternative order.

Step 5: Step 5 of Scheme 1 is an optional step or series of steps to transform the group $R^{12}$ in intermediate (x) to the group $R^7$ found in molecule (xi). For example, if $R^{12}$ is bromo and the desired group $R^7$ is an aromatic or heteroaromatic group, this transformation may be effected by reacting intermediate (x) with an optionally protected aromatic or heteroaromatic boronic acid or boronic ester, a catalyst such as $PdCl_2(dppf)$-DCM complex, and a base such as tripotassium phosphate in a solvent mixture such as dioxane and water. If the group installed contains a protecting group, a further optional step may be conducted to remove that protecting group under appropriate conditions if desired. For example, if the group installed was a pyrazole with a tetrohydropyran protecting group, the tetrahydropyran may be removed by reaction with an acid such as trifluoroacetic acid in a solvent such as dichloromethane. Alternatively, if $R^{12}$ is bromo and the desired group $R^7$ is an aromatic or heteroaromatic group, this transformation may be effected by reacting intermediate (x) first with a compound such as $PdCl_2(dppf)$-DCM complex bis(pinacolato)diboron, a reagent such as potassium acetate, and a catalyst such as $PdCl_2(dppf)$-DCM complex in a solvent such as dioxane, then reacting the resulting boronic ester with an appropriate aryl or heteroaryl halide, a base such as sodium carbonate, and a catalyst such as tetrakis(triphenylphosphine)palladium (O) in an appropriate solvent mixture such as dioxane and water. Alternatively, if $R^{12}$ is bromo and the desired group $R^7$ is a heterocycle linked through a nitrogen atom, this step may be effected by reaction of intermediate (x) with the appropriate heterocycle in the presence of a copper source such as copper (I) iodide, a base such as sodium carbonate, and a ligand such as N,N'-dimethylethane-1,2-diamine in an appropriate solvent such as DMSO.

Step 6: Step 6 of Scheme 2 is an optional step or series of steps to transform the group $R^{13}$ in intermediate (xi) to the group W found in molecule (xii). For example, if the group $R^{13}$ contains a Boc-protected amine and the desired group W contains an amide, this transformation may be accomplished by first removing the Boc group with a suitable combination of acid and solvent, such as hydrochloric acid and dioxane, then forming the desired amide by reaction with the appropriate carboxylic acid, a coupling agent such as T3P, and a base such as triethylamine in a solvent such as DMF. Alternatively, if the group $R^{13}$ contains an unsaturated group such as an alkyne, and the desired group W is fully saturated, this transformation may be effected by reaction with hydrogen and a suitable catalyst such as palladium on carbon.

Step 7: Step 7 of Scheme 2 is an optional step or series of steps to transform the group $R^{11}$ in intermediate (xii) to the group $R^3$ found in molecule (xiii).

Step 8: Step 8 of Scheme 2 is an optional step or series of steps to transform the group $R^{10}$ in intermediate (xiii) to the group W' found in molecule (xiv). For example, if the group $R^{10}$ contains an alcohol protected with a benzyl ether, and the desired group W' is the corresponding alcohol, this transformation may be effected by reaction with a suitable acid, such as hydrochloric acid. If group $R^{10}$ contains an alcohol, and the desired group $R^2$ contains an amine at the same location, this transformation may be effected by first reacting intermediate (xiii) with a reagents such as thionyl chloride in a solvent such as dichloromethane, then by reacting the resulting chloride with an amine such as ethylamine, sodium iodide, and a base such as potassium carbonate in a solvent such as acetonitrile.

One skilled in the art will recognize that a number of these steps may be performed in alternative order, depending on the groups desired in the final molecule (xiv). For example, for some molecules, the transformation of the group $R^{12}$ to $R^7$ described in Step 5 may be conducted prior to the transformation of the group Z to the group $R^{13}$ described in Step 4.

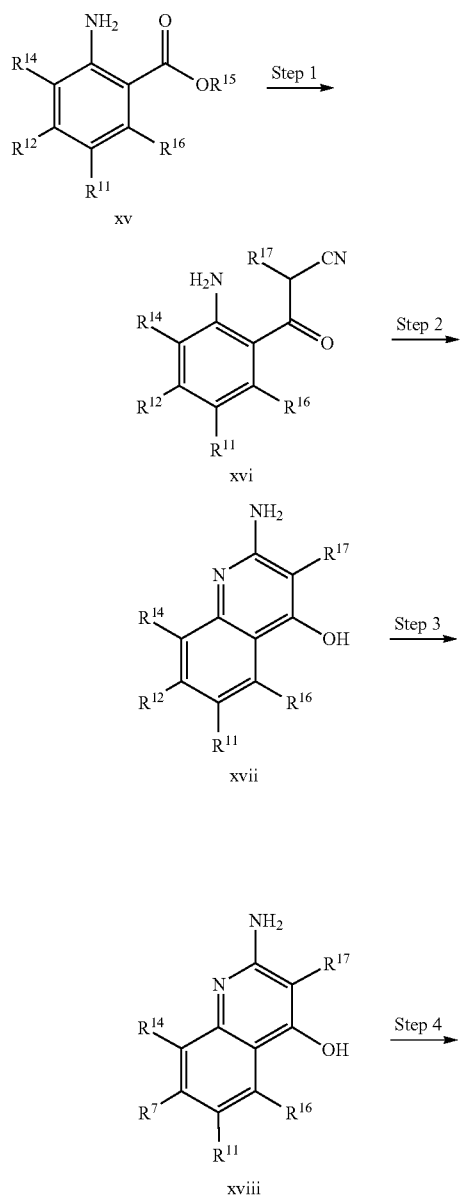

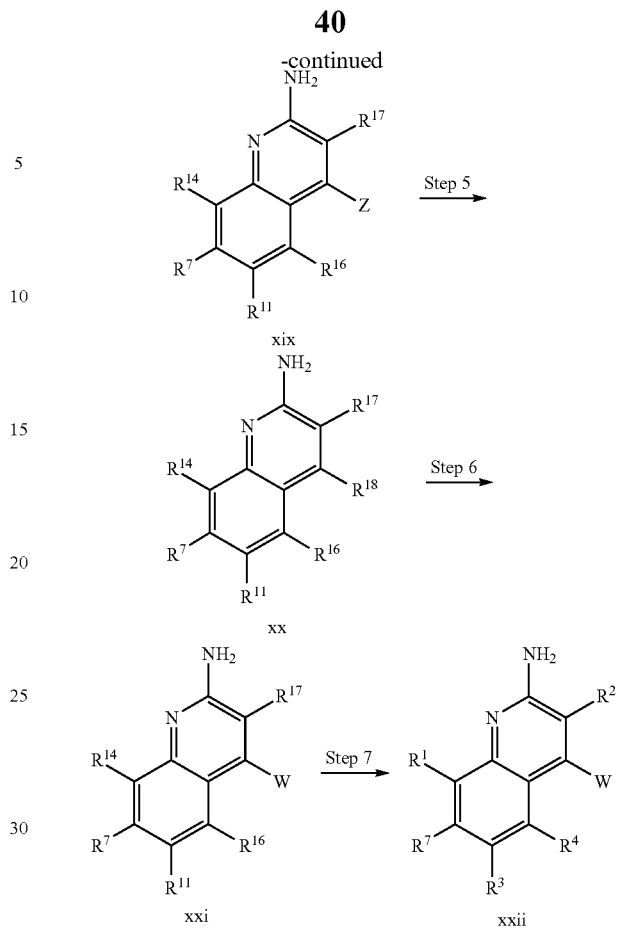

Step 1: The first step of Scheme 3 begins with a suitably functionalized 2-aminobenzoate (xv). If desired, the groups $R^{11}$, $R^{12}$, $R^{14}$ and $R^{16}$ may be the groups $R^3$, $R^7$, $R^1$ and $R^4$ found in the final product. Alternatively, one or more of these groups may be groups that can be modified at a later stage of the synthesis, such as bromo. The 2-aminobenzoates may be purchased commercially or may be synthesized by methods known to one skilled in the art. In step 1, the ester group of compound (xv) may be transformed into oxobutanitrile (xvi) with conditions such as displacement with a lithiate, such as the lithiate of acetonitrile generated the addition of a base such as n-BuLi in a solvent such as THF.

Step 2: In step 2 of Scheme 3, compound (xvi) may be transformed into quinolinol (xvii) via a based-catalyzed cyclization with exposure of (xvi) to a base such as sodium ethoxide in a solvent such as ethanol at a temperature as high as 100° C.

Steps 3 through 7 of Scheme 3 consist of a series of functional group manipulations, some optional, to convert the substituents $R^{11}$, $R^{12}$, $R^{14}$, $R^{16}$, $R^{17}$, and OH in intermediate (xvii) to the substituents $R^3$, $R^7$, $R^1$, $R^4$, $R^2$, and W desired in the final compound (xxii). One skilled in the art will recognize that some or all of these steps may not be necessary depending on the groups found in compounds (xvii) and (xxii). One skilled in the art will also recognize that, for some substrates, these steps may be performed in alternative order.

Step 3: Step 3 of Scheme 3 is an optional step or series of steps to transform the group $R^{12}$ in intermediate (xvii) to the group $R^7$ found in molecule (xviii). For example, if $R^{12}$ is bromo and the desired group $R^7$ is an aromatic or heteroaromatic group, this transformation may be effected by reacting intermediate (xvii) with an optionally protected aromatic or heteroaromatic boronic acid or boronic ester, a catalyst such as PdCl$_2$(dppf)-DCM complex, and a base such as tripotassium phosphate in a solvent mixture such as dioxane and water. If the group installed contains a protecting group, a further optional step may be conducted to remove that protecting group under appropriate conditions if desired. For example, if the group installed was a pyrazole with a tetrahydropyran protecting group, the tetrahydropyran may be removed by reaction with an acid such as trifluoroacetic acid in a solvent such as dichloromethane. Alternatively, if $R^{12}$ is bromo and the desired group $R^7$ is an aromatic or heteroaromatic group, this transformation may be effected by reacting intermediate (xvii) first with a compound such as bis(pinacolato)diboron, a reagent such as potassium acetate, and a catalyst such as PdCl$_2$(dppf)-DCM complex in a solvent such as dioxane, then reacting the resulting boronic ester with an appropriate aryl or heteroaryl halide, a base such as sodium carbonate, and a catalyst such as tetrakis (triphenylphosphine)palladium(0) in an appropriate solvent mixture such as dioxane and water. Alternatively, if $R^{12}$ is bromo and the desired group $R^7$ is a heterocycle linked through a nitrogen atom, this step may be effected by reaction of intermediate (xvii) with the appropriate heterocycle in the presence of a copper source such as copper (I) iodide, a base such as sodium carbonate, and a ligand such as N,N'-dimethylethane-1,2-diamine in an appropriate solvent such as DMSO.

Step 4: In a step 4 of Scheme 3, the alcohol group of compound (xviii) may be transformed into a halogen group or sulfonate ester, such as chloro, bromo, or triflate. If the desired group Z is chloro, this transformation may be effected by treating compound (xviii) with a reagent such as phosphoryl chloride in a solvent such as toluene. Alternatively, if the desired group Z is bromo, this transformation may be effected by treating compound (xviii) with a reagent such as phosphorous tribromide in a solvent such as DMF. Alternatively, if the desired group Z is triflate, this transformation may be effected by treating compound (xviii) with a reagent such as trifluoromethanesulfonyl chloride, a reagent such as 4-dimethylaminopyridine, and a base such as Hunig's base in a solvent such as dichloromethane.

Step 5: In step 5 of Scheme 3, the Z group of compound (xix) is transformed into group $R^{18}$ of compound (xx). The group $R^{18}$ may be the group W desired in the final compound; alternatively, it may be a group that can be transformed into group W at a later stage of the synthesis. One skilled in the art will recognize that the means to effect this transformation will depend on the nature of the groups $R^{18}$ and Z. For example, if Z is chloro and the desired group $R^{18}$ is an amine, this transformation may be effected by heating compound (xix) to a suitable temperature, such as 120° C., with an appropriate amine and a base such as Hunig's base in solvents such as DMSO or NMP. Alternatively, if Z is chloro and the desired group $R^{18}$ is an ether, this transformation may be effected by heating compound (xix) to a suitable temperature, such as 100° C., with an appropriate alcohol and a base such as potassium tert-butoxide in a solvent such as NMP. Alternatively, if Z is bromo and the desired group $R^{18}$ is an alkyne, this transformation may be effected by heating compound (xix) to a suitable temperature, such as 70° C., with an appropriate alkyne, copper (I) iodide, an appropriate base, such as Hunig's base, and a suitable palladium source, such as tetrakis(triphenylphosphine)palladium(0), in a suitable solvent such as THF. Alternatively, if Z is a triflate and the desired group $R^{18}$ is a optionally substituted alkyl group, this step may be accomplished by treating compound (xix) with an appropriate alkyl boronic acid or ester, a catalyst such as PdCl$_2$(dppf)-DCM complex, and a base such as cesium carbonate in a solvent such as dioxane.

Step 6: Step 6 of Scheme 3 is an optional step or series of steps to transform the group $R^{18}$ in intermediate (xx) to the group W found in molecule (xxi). For example, if the group $R^{18}$ contains a Boc-protected amine and the desired group W contains an amide, this transformation may be accomplished by first removing the Boc group with a suitable combination of acid and solvent, such as hydrochloric acid and dioxane, then forming the desired amide by reaction with the appropriate carboxylic acid, a coupling agent such as T3P, and a base such as triethylamine in a solvent such as DMF. Alternatively, if the group $R^{18}$ contains an unsaturated group such as an alkyne, and the desired group W is fully saturated, this transformation may be effected by reaction with hydrogen and a suitable catalyst such as palladium on carbon.

Step 7: Step 7 of Scheme 3 is an optional step or series of steps to transform the groups $R^{11}$, $R^{14}$, $R^{16}$, and $R^{17}$ in intermediate (xxi) to the groups $R^3$, $R^1$, $R^4$, and $R^2$ found in molecule (xxii).

One skilled in the art will recognize that a number of these steps may be performed in alternative order, depending on the groups desired in the final molecule (xxii). For example, for some molecules, the transformation of the group $R^{12}$ to $R^7$ described in Step 3 may be conducted after the transformation of the group Z to the group $R^{18}$ described in Step 5.

Additional aspects of this invention may be prepared as shown in Scheme 4.

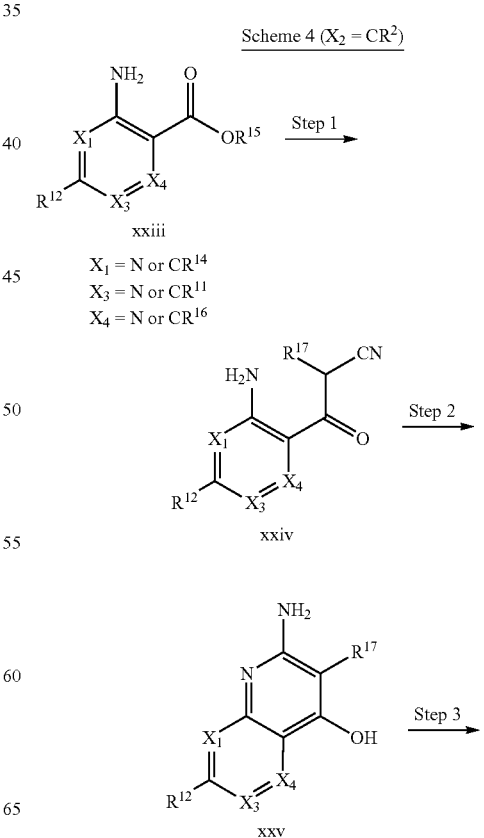

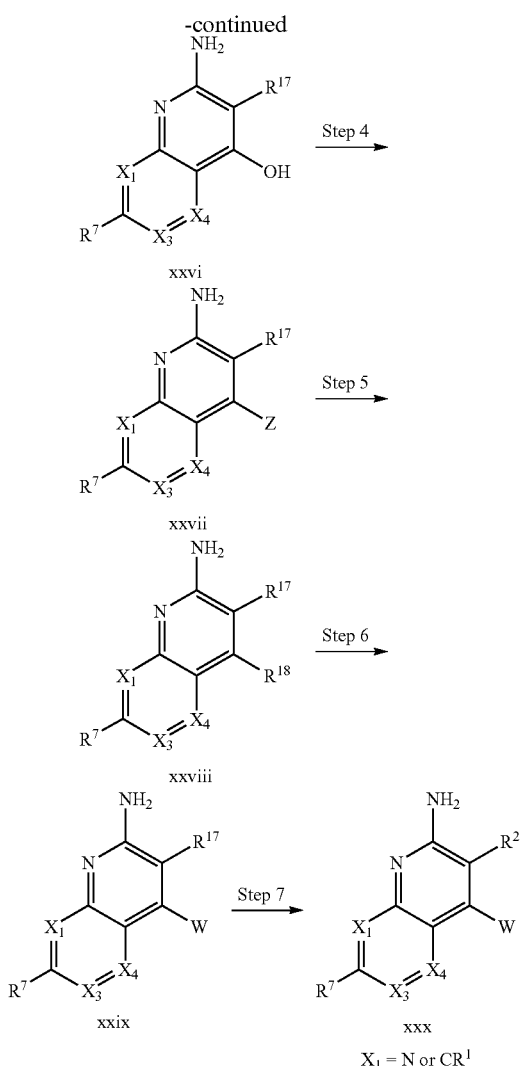

$X_1 = N$ or $CR^1$
$X_3 = N$ or $CR^3$
$X_4 = N$ or $CR^4$

Step 1: The first step of Scheme 4 begins with a suitably functionalized 2-aminonicotinate, 4-aminonicotinate, 3-aminopicolinate, or an appropriate heteroaryl ring containing multiple nitrogens (xxiii). If desired, the groups $X_1$, $X_3$, $X_4$, and $R^{12}$ may be the groups $X_1$, $X_3$, $X_4$, and $R^7$ found in the final product. Alternatively, one or more of these groups may be groups that can be modified at a later stage of the synthesis, such as bromo. Starting material (xxiii) may be purchased commercially or may be synthesized by methods known to one skilled in the art. In step 1, the ester group of compound (xxiii) may be transformed into oxobutanitrile (xxiv) with conditions such as displacement with a lithiate, such as the lithiate of acetonitrile generated the addition of as base such as n-BuLi in a solvent such as THF.

Step 2: In step 2 of Scheme 4, compound (xxiv) may be transformed into quinolinol (xxv) via a based-catalyzed cyclization with exposure of (xxiv) to a base such as sodium ethoxide in a solvent such as ethanol at a temperature as high as 100° C.

Steps 3 through 7 of Scheme 4 consist of a series of functional group manipulations, some optional, to convert the substituents $X_1$ (if $CR^{14}$), $X_3$ (if $CR^{11}$), $X_4$ (if $CR^{16}$), $R^{12}$, $R^{17}$, and OH in intermediate (xxv) to the substituents $X_1$ (if $CR^1$), $X_3$ (if $CR^3$), $X_4$ (if $CR^4$), $R^7$, $R^2$, and W desired in the final compound (xxx). One skilled in the art will recognize that some or all of these steps may not be necessary depending on the groups found in compounds (xxv) and (xxx). One skilled in the art will also recognize that, for some substrates, these steps may be performed in alternative order.

Step 3: Step 3 of Scheme 4 is an optional step or series of steps to transform the group $R^{12}$ in intermediate (xxv) to the group $R^7$ found in molecule (xxvi). For example, if $R^{12}$ is bromo and the desired group $R^7$ is an aromatic or heteroaromatic group, this transformation may be effected by reacting compound (xxv) with an optionally protected aromatic or heteroaromatic boronic acid or boronic ester, a catalyst such as $PdCl_2$(dppf)-DCM complex, and a base such as tripotassium phosphate in a solvent mixture such as dioxane and water. If the group installed contains a protecting group, a further optional step may be conducted to remove that protecting group under appropriate conditions if desired. For example, if the group installed was a pyrazole with a tetrahydropyran protecting group, the tetrahydropyran may be removed by reaction with an acid such as trifluoroacetic acid in a solvent such as dichloromethane. Alternatively, if $R^{12}$ is bromo and the desired group $R^7$ is an aromatic or heteroaromatic group, this transformation may be effected by reacting intermediate (xxv) first with a compound such as bis(pinacolato)diboron, a reagent such as potassium acetate, and a catalyst such as $PdCl_2$(dppf)-DCM complex in a solvent such as dioxane, then reacting the resulting boronic ester with an appropriate aryl or heteroaryl halide, a base such as sodium carbonate, and a catalyst such as tetrakis(triphenylphosphine)palladium(0) in an appropriate solvent mixture such as dioxane and water. Alternatively, if $R^{12}$ is bromo and the desired group $R^7$ is a heterocycle linked through a nitrogen atom, this step may be effected by reaction of intermediate (xxv) with the appropriate heterocycle in the presence of a copper source such as copper (I) iodide, a base such as sodium carbonate, and a ligand such as N,N'-dimethylethane-1,2-diamine in an appropriate solvent such as DMSO.

Step 4: In a step 4 of Scheme 4, the alcohol group of compound (xxvi) may be transformed into a halogen group or sulfonate ester, such as chloro, bromo, or triflate. If the desired group Z is chloro, this transformation may be effected by treating compound (xxvi) with a reagent such as phosphoryl chloride in a solvent such as toluene. Alternatively, if the desired group Z is bromo, this transformation may be effected by treating compound (xxvi) with a reagent such as phosphorous tribromide in a solvent such as DMF. Alternatively, if the desired group Z is triflate, this transformation may be effected by treating compound (xxvi) with a reagent such as trifluoromethanesulfonyl chloride, a reagent such as 4-dimethylaminopyridine, and a base such as Hunig's base in a solvent such as dichloromethane.

Step 5: In step 5 of Scheme 4, the Z group of compound (xxvii) is transformed into group $R^{18}$ of compound (xxvii). The group $R^{18}$ may be the group W desired in the final compound; alternatively, it may be a group that can be transformed into group W at a later stage of the synthesis. One skilled in the art will recognize that the means to effect this transformation will depend on the nature of the groups $R^{18}$ and Z. For example, if Z is chloro and the desired group $R^{18}$ is an amine, this transformation may be effected by heating compound (xxvii) to a suitable temperature, such as 120° C., with an appropriate amine and a base such as Hunig's base in solvents such as DMSO or NMP. Alternatively, if Z is chloro and the desired group $R^{18}$ is an ether, this transformation may be effected by heating compound (xxvii) to a suitable temperature, such as 100° C., with an appropriate alcohol and a base such as potassium tert-butoxide in a solvent such as NMP. Alternatively, if Z is bromo and the desired group $R^{18}$ is an alkyne, this transformation may be effected by heating compound (xxvii) to a suitable temperature, such as 70° C., with an appropriate alkyne, copper (I) iodide, an appropriate base, such as Hunig's base, and a suitable palladium source, such as tetrakis(triphenylphosphine)palladium(0), in a suitable solvent such as THF. Alternatively, if Z is a triflate and the desired group $R^{18}$ is a optionally substituted alkyl group, this step may be accomplished by treating compound (xxvii) with an appropriate alkyl boronic acid or ester, a catalyst such as $PdCl_2$(dppf)-DCM complex, and a base such as cesium carbonate in a solvent such as dioxane.

Step 6: Step 6 of Scheme 4 is an optional step or series of steps to transform the group $R^{18}$ in intermediate (xxviii) to the group W found in molecule (xxix). For example, if the group $R^{18}$ contains a Boc-protected amine and the desired group W contains an amide, this transformation may be accomplished by first removing the Boc group with a suitable combination of acid and solvent, such as hydrochloric acid and dioxane, then forming the desired amide by reaction with the appropriate carboxylic acid, a coupling agent such as T3P, and a base such as triethylamine in a solvent such as DMF. Alternatively, if the group $R^{18}$ contains an unsaturated group such as an alkyne, and the desired group W is fully saturated, this transformation may be effected by reaction with hydrogen and a suitable catalyst such as palladium on carbon.

Step 7: Step 7 of Scheme 4 is an optional step or series of steps to transform the groups $X_1$ (if $C^{14}$), $X_3$ (if $C^{11}$), $X_4$ (if $C^{16}$), and $R^{17}$ in intermediate (xxix) to the groups $X_1$ (if $CR^1$), $X_3$ (if $CR^3$), $X_4$ (if $CR^4$), and $R^2$ found in molecule (xxx).

One skilled in the art will recognize that a number of these steps may be performed in alternative order, depending on the groups desired in the final molecule (xxx). For example, for some molecules, the transformation of the group $R^{12}$ to $R^7$ described in Step 3 may be conducted after the transformation of the group Z to the group $R^{18}$ described in Step 5 or prior to transformation outlined in Step 1.

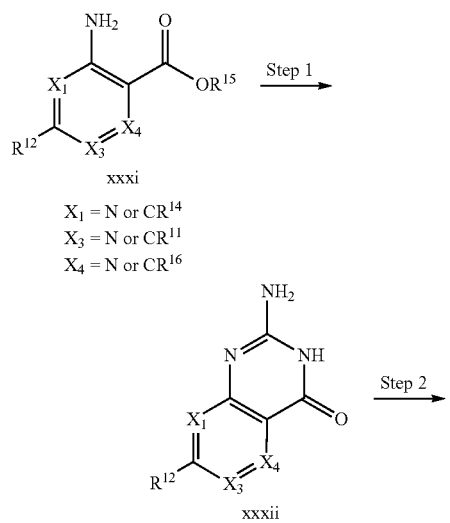

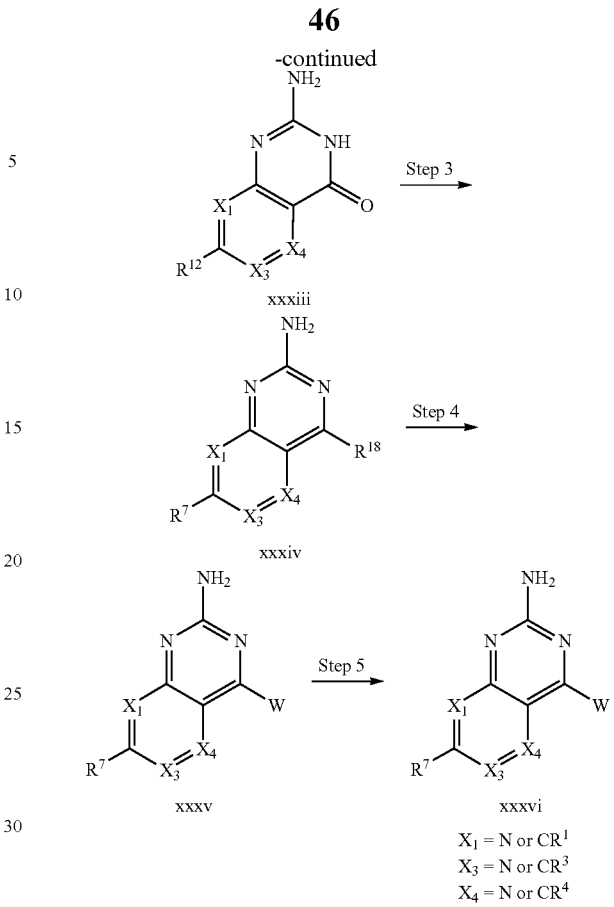

Step 1: The first step of Scheme 5 begins with a suitably functionalized 2-(halogen)nicotinate, 4-(halogen)nicotinate, 3-(halogen)picolinate, or an appropriate heteroaryl ring containing multiple nitrogens (xxxi).

If desired, the groups $X_1$, $X_3$, $X_4$, and $R^{12}$ may be the groups $X_1$, $X_3$, $X_4$, and $R^7$ found in the final product. Alternatively, one or more of these groups may be groups that can be modified at a later stage of the synthesis, such as bromo. Starting material (xxxi) may be purchased commercially or may be synthesized by methods known to one skilled in the art. In step 1, compound (xxxi) may be transformed into pyrimidinone (xxxii) when treated with guanidine hydrochloride in the presence of a suitable base such as NaH in a solvent such as DMA or NaOtBu in a solvent such as 2-propanol at a temperature in the range of 90-160° C.

Steps 2 through 5 of Scheme 5 consist of a series of functional group manipulations, some optional, to convert the substituents $X_1$ (if $CR^{14}$), $X_3$ (if $CR^{11}$), $X_4$ (if $CR^{16}$), $R^{12}$, and OH in intermediate (xxxii) to the substituents $X_1$ (if $CR^1$), $X_3$ (if $CR^3$), $X_4$ (if $CR^4$), $R^7$, and W desired in the final compound (xxxvi). One skilled in the art will recognize that some or all of these steps may not be necessary depending on the groups found in compounds (xxxiii) and (xxxvi). One skilled in the art will also recognize that, for some substrates, these steps may be performed in alternative order.

Step 2: Step 2 of Scheme 5 is an optional step or series of steps to transform the group $R^{12}$ in compound (xxxii) to the group $R^7$ found in molecule (xxxiii). For example, if $R^{12}$ is bromo and the desired group $R^7$ is an aromatic or heteroaromatic group, this transformation may be effected by reacting intermediate (xxxii) with an optionally protected aromatic or heteroaromatic boronic acid or boronic ester, a catalyst such as PdCl$_2$(dppf)-DCM complex, and a base such as tripotassium phosphate in a solvent mixture such as dioxane and water. If the group installed contains a protecting group, a further optional step may be conducted to remove that protecting group under appropriate conditions if desired. For example, if the group installed was a pyrazole with a tetrahydropyran protecting group, the tetrahydropyran may be removed by reaction with an acid such as trifluoroacetic acid in a solvent such as dichloromethane. Alternatively, if R$^{12}$ is bromo and the desired group R$^7$ is an aromatic or heteroaromatic group, this transformation may be effected by reacting intermediate (xxxii) first with a compound such as bis(pinacolato)diboron, a reagent such as potassium acetate, and a catalyst such as PdCl$_2$(dppf)-DCM complex in a solvent such as dioxane, then reacting the resulting boronic ester with an appropriate aryl or heteroaryl halide, a base such as sodium carbonate, and a catalyst such as tetrakis (triphenylphosphine)palladium(0) in an appropriate solvent mixture such as dioxane and water. Alternatively, if R$^{12}$ is bromo and the desired group R$^7$ is a heterocycle linked through a nitrogen atom, this step may be effected by reaction of intermediate (xxxii) with the appropriate heterocycle in the presence of a copper source such as copper (I) iodide, a base such as sodium carbonate, and a ligand such as N,N'-dimethylethane-1,2-diamine in an appropriate solvent such as DMSO.

Step 3: In step 3 of Scheme 5, the pyridone of compound (xxxiii) is transformed into group R$^{18}$ of compound (xxxiv). The group R$^{18}$ may be the group W desired in the final compound; alternatively, it may be a group that can be transformed into group W at a later stage of the synthesis. One skilled in the art will recognize that the means to effect this transformation will depend on the nature of the group R$^{18}$. For example, if the desired group R$^{18}$ is an amine, this transformation may be effected by reacting compound (xxxiii) with an appropriate amine, a coupling reagent such as BOP, and a base such as DBU in a solvent such as DMF.

Step 4: Step 4 of Scheme 5 is an optional step or series of steps to transform the group R$^{18}$ in intermediate (xxxiv) to the group W found in molecule (xxxv). For example, if the group R$^{18}$ contains a Boc-protected amine and the desired group W contains an amide, this transformation may be accomplished by first removing the Boc group with a suitable combination of acid and solvent, such as hydrochloric acid and dioxane, then forming the desired amide by reaction with the appropriate carboxylic acid, a coupling agent such as T3P, and a base such as triethylamine in a solvent such as DMF. Alternatively, if the group R$^{18}$ contains an unsaturated group such as an alkyne, and the desired group W is fully saturated, this transformation may be effected by reaction with hydrogen and a suitable catalyst such as palladium on carbon.

Step 5: Step 5 of Scheme 5 is an optional step or series of steps to transform the groups X$_1$ (if C$^{14}$), X$_3$ (if C$^{11}$), and X$_4$ (if C$^{16}$) in intermediate (xxxv) to the groups X$_1$ (if C$^1$), X$_3$ (if C$^3$), and X$_4$ (if C$^4$) found in molecule (xxxvi).

One skilled in the art will recognize that a number of these steps may be performed in alternative order, depending on the groups desired in the final molecule (xxxvi). For example, for some molecules, the transformation of the group R$^{12}$ to R$^7$ described in Step 2 may be conducted after the transformation of the pyridone to the group R$^{18}$ described in Step 3.

A number of instances of this invention have a W group that contains an amine. Many of the requisite amines are commercially available; however, one trained in the art will appreciate that there are many established methods for the preparation of compounds of this type (see for example R. Larock, Comprehensive Organic Transformations, VCH Publishers (1989)). Exemplary preparations of amines are provided in the specific examples.

Evaluation of Biological Activity

Measurement of IL-1β Production in PMA-Differentiated THP-1 Cells

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml) and streptomycin (100 µg/ml), and maintained in log phase prior to experimental setup. Prior to the experiment THP-1 were treated with PMA (Phorbol 12-myristate 13-acetate) (10 µg/ml) for 24 hours. The day of the experiment the media was removed and attaching cells were treated with trypsin for 2 minutes, cells were then collected, washed with PBS (phosphate buffer saline), spin down, resuspended in 2% heat inactivated FBS with RPMI at a concentration of 1×10$^6$ cells/ml, and 100 µl was plated in a 96 well plate. Compounds were dissolved in dimethyl sulfoxide (DMSO) and added to the culture medium to achieve desired concentration (e.g. 100, 30, 10, 3, 1, 0.3 or 0.1 µM). Cells were incubated with compounds for 4 hours. Cell free supernatant was collected and the production of IL-1β was evaluated by ELISA. A vehicle only control was run concurrently with each experiment. Final DMSO concentration was 1%. Compounds exhibit a dose-related increase of IL-1β production in PMA-differentiated THP-1 cells.

Measurement of IL-1β Production in PMA-Differentiated THP-1 Cells (Alternative Procedure)

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml), streptomycin (100 µg/ml), HEPES (10 mM) and sodium pyruvate (1 mM) and maintained in log phase prior to experimental setup. Prior to the experiment, THP-1 cells were treated with PMA (Phorbol 12-myristate 13-acetate) (20 µg/ml) overnight. The day of the experiment, the media was removed and attached cells were treated with trypsin for 2 minutes, cells were then collected, washed with PBS (phosphate buffer saline), pelleted by centrifugation and resuspended in 2% heat inactivated FBS with RPMI at a concentration of 50,000 cells/well in a 384 well plate. Cell free supernatant was collected and the production of IL-1β was evaluated by ELISA. Compounds were dissolved in dimethyl sulfoxide (DMSO) and added to the culture medium to achieve desired concentration (e.g. 100, 30, 10, 3, 1, 0.3 or 0.1 µM). Cells were incubated with compounds for 2 hours. A vehicle only control was run concurrently with each experiment. Final DMSO concentration was 1%. Compounds exhibit a dose-related increase of IL-1β production in PMA-differentiated THP-1 cells.

Measurement of IL-1β Production—hTRF Protocol (Second Alternative Procedure)

Serial dilutions of compounds in DMSO were added to low volume 384 well plates at 100 nl/well using an ECHO 550 acoustic dispenser (Labcyte) to achieve final starting concentration of 10 µM in assay.

THP-1 cells in RPMI (Gibco, 11875) media with 10% FBS at a density of 1×10$^6$ cell/ml in a T175 flask were treated with a final concentration of phorbol 12-myristate 13-acetate (PMA) (Sigma, P1585) of 50 ng/ml overnight at 37° C. at 5% $CO_2$ for differentiation. Cells were harvested the next day after rinsing well wth dPBS using 0.5% trypsin. A cell solution was prepared of $1\times10^6$ cells/ml for 50,000 cells in 50 µl/well in RPMI media with 2% FBS. Cells were plated using a multichannel pipette onto the compound dilutions in Greiner, 384 well, black clear bottom tissue culture treated plates (781090). The plates were incubated in 37° C. incubator at 5% $CO_2$ for 2 hours.

After the 2 hour incubation, the cell plates were spun in the centrifuge for 5 minutes at 1200 rpm. Using the Felix (CyBio), 8 µl of the supernatant was transferred to 384 well, low volume, white proxy plates. (Perkin Elmer, 6008230). A human IL1beta hTRF kit was used to analyze the supernatant (CISBIO, 62HIL1BPEG). The kit instructions were followed for preparing the IL1Beta standard curve and then the antibodies from the kit were diluted 1:40 rather than 1:20 as kit instructed. Once combined, the antibodies were added across the plates, 5 µl/well. The plates were sealed and incubated at 4° C. overnight. The plates were then read on the Perkin Elmer EnVision at 665/615 nm using the hTRF laser. Compounds exhibited a dose-related increase of IL-1β production.

Measurement of IL-1β Production—Human Whole Blood Assay

Serial dilutions of compounds in DMSO were added to low volume 384 well plates at 100 nl/well using an ECHO 550 acoustic dispenser (Labcyte) to achieve final starting concentration of 10 uM in assay.

Human venous whole blood obtained from healthy donors was pre-treated with LPS (Invivogen, Cat #tlrl-eblps) at 1 ng/ml for four hours at 37° C. in a humidified 95% air/5% $CO_2$ incubator. Primed blood was added to the compound plate and incubated for additional 4 hours at 37° C. IL-1beta in the supernatants was measured using AlphLISA kit (Cat #AL220) according to manufacturer's instructions. Compounds exhibited a dose-related increase of IL-1β production. EC50 was determined using primed but untreated blood as baseline.

Measurement of IL-1β Production—Mouse hTRF Protocol

Immortalized mouse macrophages derived from $C_{57}BL/6$ mice were obtained from Ericke Latz, University of Bonn/University of Massachusetts Worchester, MA The cells were harvested using 0.05% Trypsin and washed with PBS. Cell were plated at 30,000 cells per well in 25 ul in DMEM (Gibco, 11965) supplemented with 2% FBS and incubated for 10 minutes at 37° C. at 5% $CO_2$. LPS-EB (Invivogen, tlr-eblps) was added to a final concentration of 200 ng/ml at 5ul/well and cells were incubated for 2 hours at 37° C. at 5% $CO_2$.

Serial dilutions of compounds in DMSO were added to cells in low volume 384 well plates at 60 nl/well using an ECHO 550 acoustic dispenser (Labcyte) to achieve final starting concentration of 50 uM in assay and incubated with compounds for additional 2 hours at 37° C. at 5% $CO_2$.

After the 2 hour incubation, the cell plates were spun in the centrifuge for 5 minutes at 1200 rpm. Using the Felix (CyBio), 8 ul of the supernatant was transferred to 384 well, low volume, white proxy plates. (Perkin Elmer, 6008230). A human IL1beta hTRF kit was used to analyze the supernatant (CISBIO, 62MIL1BPEH). The kit instructions were followed for preparing the IL1Beta standard curve (the antibodies from the kit were diluted 1:40 rather than 1:20 as kit instructed). Once combined, the antibodies were added across the plates at 5 ul/well. The plates were sealed and incubated at 4° C. overnight. The plates were read on the Perkin Elmer EnVision at 665/615 nm using the hTRF laser. Data was then converted to pg/ml of IllBeta. Compounds exhibited a dose-related increase of IL-1β production.

In Vitro Human TLR7 and TLR8 Binding Reporter Assays

Logarithmically-growing human HEK-Blue cells co-expressing a TLR7 or TLR8 gene and a NF-kB/AP1-inducible SEAP (secreted embryonic alkaline phosphatase; Invivogen, San Diego, CA) reporter gene are added to individual wells of a 384-well plate (15,000 cells per 20 µL per well) and maintained for 24 h at 37° C., 5% $CO_2$. Test compounds or DMSO are distributed to separate wells the next day using acoustic liquid handling technology (100 nL per well) and cells are subsequently incubated for 18 h at 37° C., 5% $CO_2$. Cellular SEAP production is measured using an Envision plate reader instrument thirty minutes after adding freshly-made Quanti-Blue reagent (prepared by following manufacturer instructions; Invivogen, San Diego, CA) to the HEK-Blue TLR Nf-kB-SEAP cell reactions. All $EC_{50}$ values (half-maximal effective concentration) are determined using proprietary data analysis software. Normalized $EC_{50}$ value=absolute value determined by setting 100% Ymax using a reference standard RLU (relative light unit) values from cells treated with 50 µM of the reference standard.

EXAMPLES

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

HPLC/Ms and Preparatory/Analytical HPLC Methods Employed in Characterization or Purification of Examples Analytical HPLC/MS was performed using the following methods:

Method A: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method B: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Method C: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

Method D: Column: Waters Acquity UPLC BEH C18, 2.1×50 mm, 1.7-µm particles; Mobile Phase A: water with 0.05% TFA; Mobile Phase B: acetonitrile with 0.05% TFA; Temperature: 50° C.; Gradient: 2-98% B over 1.0 minute, then a 0.50-minute hold at 98% B; Flow: 0.80 mL/min; Detection: UV at 254 nm.

Method E: ESI Pos/neg: Column: Waters Acquity UPLC BEH C18, 2.1×50 mm, 1.7-µm particles; Mobile Phase A:

95:5 water:acetonitrile with 10 mM NH₄OAc; Mobile Phase B: 95:5 acetonitrile:water with 10 mM NH₄OAc; Temperature: 50° C.; Gradient: 5-95% B over 1.0 minute, then a 0.50-minute hold at 95% B; Flow: 0.80 mL/min; Detection: UV at 220 nm.

Nuclear Magnetic Resonance (NMR) Spectroscopy

Chemical shifts are reported in parts per million (ppm) downfield from internal tetramethylsilane (TMS) or from the position of TMS inferred by the deuterated NMR solvent. Apparent multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities. In some cases, NMR spectra are obtained using water peak suppression, which may result in overlapping peaks not being visible or having altered shape and/or integration.

Example 1. rac-N4-((1R,2S,4S)-7-oxabicyclo[2.2.1] heptan-2-yl)-7-(1H-pyrazol-5-yl)quinazoline-2,4-diamine, TFA 1A. 2-amino-7-bromoquinazolin-4(3H)-one To a mixture of methyl 2-amino-4-bromobenzoate (485 mg, 2.1 mmol) and cyanamide (106 mg, 2.5 mmol) in dioxane (5 mL) was added 4M HCl in dioxane (0.69 mL, 2.7 mmol). The reaction mixture was heated at 70° C. for 2 hours then the temperature was increased to 100° C. for 1 hour. The reaction mixture was cooled to room temperature and diluted with ether. The white precipitate was collected by filtration and rinsed with ether followed by small ethanol rinse and water rinses. The solid was dried under vacuum to give 2-amino-7-bromoquinazolin-4(3H)-one (429 mg, 85% yield). ¹HNMR (400 MHz, DMSO) δ 8.33-8.04 (m, 2H), 7.88 (d, J=8.4 Hz, 1H), 7.64 (d, J=1.6 Hz, 1H), 7.51 (dd, J=8.4, 1.7 Hz, 1H).

1B. 2-amino-7-(1-(tetrahydro-2Hpyran-2-yl)-1Hpyrazol-5-yl)quinazolin-4(3H)-one

To a mixture of 2-amino-7-bromoquinazolin-4(3H)-one (2.86 g, 11.9 mmol), 1-(tetrahydro-2H-pyran-2-yl)-5-(4,4,5,5-tetramethyl-1,3,2-dioxaborolan-2-yl)-1Hpyrazole (3.97 g, 14.3 mmol) and cesium carbonate (11.6 g, 35.7 mmol) in dioxane (120 mL) and water (30 mL) was added PdCl₂(dppf)-CH₂Cl₂ adduct (0.97 g, 1.2 mmol) under N₂. The reaction mixture was heated with reflux condenser on 110° C. heating block. When complete the reaction was cooled to room temperature and concentrated. To the residue was added 1M NaOH (120 mL) and stirred for 20 minutes. The mixture was filtered through celite with 1M NaOH rinses. The basic aqueous mother liquor was slowly acidified with 1M citric acid to pH 4 and the resulting light tan precipitate was collected by filtration with water rinses. The solid was dried under vacuum to give 2-amino-7-(1-(tetrahydro-2Hpyran-2-yl)-1Hpyrazol-5-yl)quinazolin-4(3H)-one (2.28 g, 61.5% yield). ¹HNMR (400 MHz, DMSO) δ 11.35-10.75 (m, 1H), 7.96 (br d, J=8.1 Hz, 1H), 7.59 (s, 1H), 7.35 (s, 1H), 7.23 (br d, J=8.0 Hz, 1H), 6.66-6.36 (m, 3H), 5.26 (br d, J=9.3 Hz, 1H), 4.01 (br d, J=10.9 Hz, 1H), 3.57 (br t, J=8.8 Hz, 1H), 2.45-2.32 (m, 1H), 1.93 (br s, 1H), 1.78 (br d, J=12.5 Hz, 1H), 1.65-1.48 (m, 3H).

1C. rac-exo-tert-butyl 7-oxabicyclo[2.2.1]hept-5-en-2-ylcarbamate and endo-rac-tert-butyl 7-oxabicyclo[2.2.1]hept-5-en-2-ylcarbamate A suspension of 7-oxabicyclo[2.2.1]hept-5-en-2-amine, HCl (2.7461 g, 18.60 mmol)(mixture of endo and exo isomers, prepared as in *Bioorg. Med. Chem. Lett.* 9(7) 933-936(1999)) in 1:1 mixture of methanol-methylene chloride (50 mL) was treated with Boc-anhydride (5.73 mL, 24.70 mmol) and potassium carbonate (3.3 g, 23.88 mmol). After stirring overnight, the reaction was filtered and the filtrate evaporated. The crude product was purified on an 80 g Isco silica gel ISCO column, eluting with 0-40% ethyl acetate in hexanes. Evaporation of the first eluting fraction gave rac-exo-tert-butyl 7-oxabicyclo[2.2.1]hept-5-en-2-ylcarbamate (0.65 g) ¹H NMR (400 MHz, Chloroform-d) δ ppm 6.38 (1H, dd, J=5.94, 1.54 Hz), 6.29-6.35 (1H, m), 4.99 (1H, d, J=4.40 Hz), 4.89 (1H, d, J=6.16 Hz), 4.74 (1H, s), 3.75 (1H, t, J=6.82 Hz), 1.83 (1H, dd, J=11.88, 7.70 Hz), 1.45 (9H, s), 1.36 (1H, ddd, J=11.99, 4.51, 2.86 Hz). Evaporation of the second eluting fraction gave rac-endo-tert-butyl 7-oxabicyclo[2.2.1]hept-5-en-2-ylcarbamate (0.42 g) ¹H NMR (400 MHz, Chloroform-d) δ ppm 6.44 (1H, d, J=4.84 Hz), 6.23 (1H, dd, J=5.72, 1.32 Hz), 4.91 (1H, br. s.), 4.84 (1H, dd, J=4.73, 1.21 Hz), 4.42 (1H, d, J=4.18 Hz), 4.11 (1H, br. s.), 2.18-2.29 (1H, m), 1.34 (9H, d, J=3.96 Hz), 0.79 (1H, dd, J=11.77, 3.19 Hz).

1D. rac-tert-butyl ((1R,2S,4S)-7-oxabicyclo[2.2.1] heptan-2-yl)carbamate

A 20 mL round-bottomed flask was charged with exo-rac-tert-butyl 7-oxabicyclo[2.2.1]hept-5-en-2-ylcarbamate (50 mg, 0.237 mmol) and Pd/C, Degussa (12.59 mg, 0.012 mmol) in ethyl acetate (1 mL) and THF (0.5 mL) to give a black suspension. A hydrogen atmosphere was then introduced via balloon. Upon completion, the reaction was filtered through 0.45 μm membrane and rinsed with THF and ethyl acetate rinses. Removal of the solvent gave a colorless solid which was used without purification.

1E. rac-(1R,2S,4S)-7-oxabicyclo[2.2.1]heptan-2-amine, HCl

A 20 mL vial was charged with rac-tert-butyl ((1R,2S, 4S)-7-oxabicyclo[2.2.1]heptan-2-yl)carbamate (50 mg, 0.234 mmol) in methylene chloride (400 μl) to give a colorless solution. A solution of HCl (4 M in dioxane, 100 μl, 3.29 mmol) was added and stirring continued overnight. The reaction was concentrated and dried under vacuum to give the crude product which was used without purification.

Example 1

A vial was charged with 2-amino-7-(1-(tetrahydro-2H-pyran-2-yl)-1H-pyrazol-5-yl)quinazolin-4(3H)-one (48 mg, 0.154 mmol) and BOP (89 mg, 0.200 mmol) in DMF (0.6 mL) to give a tan suspension. DBU (0.070 mL, 0.463 mmol) was added to eventually give an orange solution. After a few minutes rac-(1R,2S,4S)-7-oxabicyclo[2.2.1]heptan-2-amine, HCl (34.6 mg, 0.231 mmol) was added and stirring continued overnight. The reaction was diluted with 10% lithium chloride solution and some saturated sodium bicarbonate solution to give a light tan precipitate. The solid was extracted into ethyl acetate. The organic phase was dried over magnesium sulfate, filtered and evaporated to give the crude product. This material was dissolved in ethanol (2 mL) and treated with 4 M HCl in dioxane (0.19 mL, 0.77 mmol). After about three quarters of an hour, the solvent was evaporated and the residue dissolved in methanol for purification. The crude material was purified via preparative LC/MS with the following conditions: Column: XBridge C18, 200 mm×19 mm, 5-µm particles; Mobile Phase A: 5:95 acetonitrile:water with 0.05% trifluoroacetic acid; Mobile Phase B: 95:5 acetonitrile:water with 0.05% trifluoroacetic acid; Gradient: a 3-minute hold at 0% B, 0-40% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to give rac-N4-((1R,2S,4S)-7-oxabicyclo[2.2.1]heptan-2-yl)-7-(1H-pyrazol-5-yl)quinazoline-2,4-diamine (19.3 mg, 0.044 mmol, 28%) as a TFA salt. HPLC RT: 0.98 min. LCMS (M+H)$^+$: 323.3 (Method C). $^1$H-NMR (400 MHz, DMSO) δ 9.00 (br d, J=5.7 Hz, 1H), 8.48 (br d, J=8.5 Hz, 1H), 8.38-7.96 (m, 2H), 7.88 (br s, 2H), 7.85 (br d, J=7.8 Hz, 1H), 6.90 (d, J=2.0 Hz, 1H), 4.68 (br t, J=4.6 Hz, 1H), 4.54 (d, J=5.1 Hz, 1H), 4.36-4.25 (m, 1H), 2.07-1.98 (m, 1H), 1.98-1.89 (m, 1H), 1.71-1.53 (m, 3H), 1.52-1.45 (m, 1H) location of an exchangeable proton is not evident.

Example 2. (2r,3aR,5r,6aS)-5-((2-amino-7-(1H-pyrazol-5-yl)quinazolin-4-yl)amino)octahydropentalen-2-ol To a suspension of 2-amino-7-(1-(tetrahydro-2H-pyran-2-yl)-1H-pyrazol-5-yl)quinazolin-4-ol (25 mg, 0.080 mmol) (Example 1, Step 2) and (2r,3aR,5r,6aS)-5-aminooctahydropentalen-2-ol, HCl (35.7 mg, 0.201 mmol) in DMF (0.5 mL) was added DBU (0.061 mL, 0.401 mmol) and BOP (71.0 mg, 0.161 mmol). The reaction was stirred overnight and then was diluted with water and extracted three times with ethyl acetate. The organic layers were concentrated. The residue was dissolved in methanol (1 mL) and concentrated hydrochloric acid (0.05 mL) was added. After ca. 1.5 hours, the reaction was concentrated, azeotroped with methylene chloride, dissolved in DMF, and filtered through a syringe filter. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 1% B, 1-41% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to give (2r,3aR,5r,6aS)-5-((2-amino-7-(1H-pyrazol-5-yl)quinazolin-4-yl)amino)octahydropentalen-2-ol (19.7 mg, 0.056 mmol, 62%). HPLC RT: 1.14 min. LCMS (M+H)$^+$: 351.3 (Method C). $^1$H NMR (500 MHz, DMSO-d$_6$) δ 9.00 (br d, J=5.7 Hz, 1H), 8.48 (br d, J=8.5 Hz, 1H), 8.38-7.96 (m, 2H), 7.88 (br s, 2H), 7.85 (br d, J=7.8 Hz, 1H), 6.90 (d, J=2.0 Hz, 1H), 4.68 (br t, J=4.6 Hz, 1H), 4.54 (d, J=5.1 Hz, 1H), 4.36-4.25 (m, 1H), 2.07-1.98 (m, 1H), 1.98-1.89 (m, 1H), 1.71-1.53 (m, 3H), 1.52-1.45 (m, 1H) all exchangeable protons are not observed.

Example 3. 6-((2-amino-7-(1H-pyrazol-5-yl)quinazolin-4-yl)amino)spiro[3.3]heptan-2-ol To a suspension of 2-amino-7-(1-(tetrahydro-2H-pyran-2-yl)-1H-pyrazol-5-yl)quinazolin-4-ol (25 mg, 0.080 mmol) (Example 1, Step 2) and 6-aminospiro[3.3]heptan-2-ol, HCl (36.0 mg, 0.220 mmol) in DMF (0.5 mL) was added DBU (0.061 mL, 0.401 mmol) and BOP (71.0 mg, 0.161 mmol). The reaction was stirred overnight and then was diluted with water and extracted three times with ethyl acetate. The organic layers were concentrated. The residue was dissolved in methanol (1 mL) and concentrated hydrochloric acid (0.05 mL) was added. After ca. 45 minutes, the reaction was concentrated, azeotroped with methylene chloride, dissolved in DMF, and passed through a syringe filter. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 25 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give 6-((2-amino-7-(1H-pyrazol-5-yl)quinazolin-4-yl)amino)spiro[3.3]heptan-2-ol (9.0 mg, 0.027 mmol, 32%). HPLC RT: 0.79 min. LCMS (M+H)$^+$: 337.0 (Method C). $^1$H NMR (500 MHz, DMSO-d$_6$) δ 8.16-8.03 (m, 2H), 7.79-7.67 (m, 1H), 7.63 (br s, 1H), 7.54 (br d, J=6.7 Hz, 1H), 7.25-7.14 (m, 1H), 6.80 (s, 1H), 6.42 (br d, J=2.1 Hz, 1H), 4.67-4.52 (m, 1H), 4.06-3.93 (m, 1H), 2.42-2.34 (m, 2H), 2.33-2.24 (m, 1H), 2.23-2.17 (m, 1H), 2.16-2.07 (m, 2H), 1.89-1.79 (m, 2H).

Example 4 to Example 8 were prepared according to synthetic procedures similar to those described for Example 2 using the appropriate starting materials.

Example 9. rac-4-(2-oxa-5-azabicyclo[2.2.1]heptan-5-yl)-7-(1H-pyrazol-3-yl)quinazolin-2-amine, TFA salt 9A. 4-(2-oxa-5-azabicyclo[2.2.1]heptan-5-yl)-7-bromoquinazolin-2-amine A vial was charged with 2-amino-7-bromoquinazolin-4(3H)-one (99 mg, 0.412 mmol), 2-oxa-5-azabicyclo[2.2.1]heptane, HCl (168 mg, 1.237 mmol), BOP (237 mg, 0.536 mmol), and DBU (311 µl, 2.062 mmol) in DMF (2062 µl). The reaction was stirred overnight. The reaction was diluted with ethyl acetate and washed with water. The organic layer was concentrated in vacuo to give the desired crude product 4-(2-oxa-5-azabicyclo[2.2.1]heptan-5-yl)-7-bromoquinazolin-2-amine (132 mg, 0.411 mmol, 100% yield)) as a brown oil. HPLC RT: 0.55 min. LCMS (M+H)+: 321 (Method D).

9B. rac-4-(2-oxa-5-azabicyclo[2.2.1]heptan-5-yl)-7-(1H-pyrazol-3-yl)quinazolin-2-amine Dioxane and water were degassed with nitrogen for 15 minutes. To a 2 dram vail was added 4-(2-oxa-5-azabicyclo[2.2.1]heptan-5-yl)-7-bromoquinazolin-2-amine (132 mg, 0.411 mmol), 3-(4,4,5,5-tetramethyl-1,3,2-dioxaborolan-2-yl)-1H-pyrazole (120 mg, 0.616 mmol), PdCl$_2$(dppf)-CH$_2$Cl$_2$ adduct (33.6 mg, 0.041 mmol), dioxane (4110 µl) and a 2M solution of tripotassium phosphate (616 µl, 1.233 mmol) in water. The reaction mixture was then heated at 95° C. for three hours. The reaction was concentrated in vacuo and dissolved in DMF. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-30% B over 23 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to give rac-4-(2-oxa-5-azabicyclo[2.2.1]heptan-5-yl)-7-(1H-pyrazol-3-yl)quinazolin-2-amine (30.2 mg) as a TFA salt. HPLC RT: 0.96 min. LCMS (M+H)$^+$: 309.3 (Method C). $^1$H NMR (500 MHz, DMSO-d$_6$) δ 8.14 (d, J=8.9 Hz, 1H), 7.87 (br s, 2H), 7.79 (br d, J=7.3 Hz, 1H), 6.88 (d, J=2.1 Hz, 1H), 5.46 (s, 1H), 4.80 (s, 1H), 4.22 (br dd, J=11.6, 4.0 Hz, 1H), 4.02-3.80 (m, 2H), 2.09-2.01 (m, 1H), 2.00-1.94 (m, 1H) Two protons are not visible, likely to due overlap with suppressed water peak.

Example 10. 4-((1R,4R)-2-oxa-5-azabicyclo[2.2.1]heptan-5-yl)-7-(1H-pyrazol-3-yl)quinazolin-2-amine and 4-((1S,4S)-2-oxa-5-azabicyclo[2.2.1]heptan-5-yl)-7-(1H-pyrazol-3-yl)quinazolin-2-amine

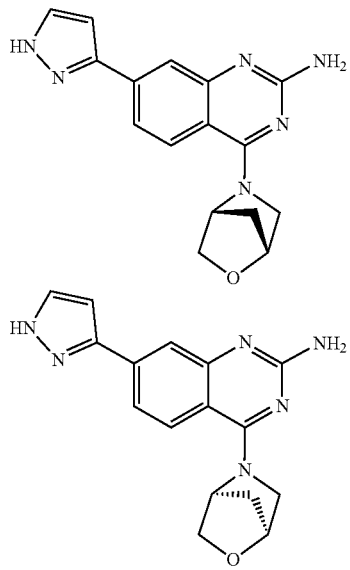

A sample of rac-4-(2-oxa-5-azabicyclo[2.2.1]heptan-5-yl)-7-(1H-pyrazol-3-yl)quinazolin-2-amine, TFA salt (Example 9) (25.7 mg) was resolved by chiral SFC using the following conditions: Column: Chiral AS, 30×250 mm. 5 micron, mobile phase: 70% CO$_2$/30% IPA w/0.1% DEA, flow: 100 mL/min. Evaporation of the solvent from the first eluting peak gave Example 11 (3.5 mg). HPLC RT: 0.97 min. LCMS (M+H)$^+$: 309.2 (Method C). $^1$H NMR (500 MHz, DMSO-d$_6$) δ 7.91 (d, J=8.7 Hz, 1H), 7.76 (br s, 1H), 7.66 (d, J=1.7 Hz, 1H), 7.49 (br d, J=8.6 Hz, 1H), 6.81 (d, J=2.2 Hz, 1H), 6.20 (br s, 2H), 5.20 (s, 1H), 4.70 (s, 1H), 4.11 (br d, J=9.8 Hz, 1H), 3.97-3.89 (m, 1H), 3.87-3.79 (m, 1H), 3.68 (br d, J=9.7 Hz, 1H), 2.02-1.93 (m, 1H), 1.90-1.84 (m, 1H).

Example 11. (1s,3r,5R,7S)-3-((2-Amino-7-(1H-pyrazol-3-yl)quinazolin-4-yl)amino)adamantan-1-ol 11A. (1s,3r,5R,7S)-3-((2-amino-7-bromoquinazolin-4-yl)amino)adamantan-1-ol To a mixture of 2-amino-7-bromoquinazolin-4(1H)-one (30 mg, 0.12 mmol) and BOP (71.9 mg, 0.16 mmol) in anhydrous DMF (0.8 mL), at room temperature in a sealable reaction vial, was added 3-amino-1-adamantanol (62.7 mg, 0.38 mmol) followed by 1,8-diazabicyclo-[5.4.0]undec-7-ene (0.1 mL, 0.66 mmol). The resulting mixture was stirred at ambient temperature for 18 hours before being partitioned between EtOAc and water. The layers were separated and the aqueous layer was extracted twice more with EtOAc. These organic extracts were combined with the original organic layer and were concentrated in vacuo to afford a gold oil which was used in the next step, without further purification, based on quantitative yield. MS (ES): m/z=389/391 [M+H]$^+$. T$_r$=0.65 min.

Example 11

A mixture of (1s,3r,5R,7S)-3-((2-amino-7-bromoquinazolin-4-yl)amino)adamantan-1-ol (0.12 mmol), 3-(4,4,5,5-tetramethyl-1,3,2-dioxaorolane)-pyrazole (53.4 mg, 0.28 mmol) and Cs$_2$CO$_3$ (122 mg, 0.38 mmol) in dioxane (2.25 mL) and water (0.3 mL), at room temperature in a sealable reaction vial, was sparged with argon for approximately ten minutes before PdCl$_2$(dppf)-CH$_2$Cl$_2$ (20.4 mg, 0.025 mmol) was added. The vial was sealed and the reaction was heated at 90° C. for 15.5 hours. After cooling to room temperature, the mixture was diluted with DMSO then passed through a syringe filter before being partitioned between EtOAc and water. The layers were separated and the aqueous layer was extracted with 5% MeOH in CHCl$_3$. The initial organic extract was concentrated in vacuo before the second organic extract was added to it and then concentrated in vacuo to afford a dark brown residue that was diluted with DMF, passed through a syringe filter then purified by preparative HPLC/MS to afford the title compound (10.7 mg; 22% yield). MS(ES): m/z=377 [M+H]$^+$. t$_R$=1.01 min (Method C). $^1$H NMR (500 MHz, DMSO-d$_6$) δ 8.11 (d, J=8.5 Hz, 1H), 7.73 (br s, 1H), 7.59 (d, J=1.5 Hz, 1H), 7.50 (br d, J=7.9 Hz, 1H), 6.94 (s, 1H), 6.79 (d, J=2.1 Hz, 1H), 6.31 (br s, 2H), 3.61 (br s, 1H), 2.22-2.15 (m, 4H), 2.13-2.06 (m, 4H), 1.69-1.63 (m, 2H), 1.62-1.53 (m, 3H), 1.48-1.42 (m, 1H). Integration of OH proton appears to be reduced due to suppression of water peak.

Example 12 and Example 13 were prepared according to synthetic procedures similar to those described for Example 11 from the appropriate starting materials.

Example 14. (2r,3aR,5r,6aS)-5-((2-amino-7-(1H-pyrazol-5-yl)quinolin-4-yl)amino)octahydropentalen-2-ol 14A. 7-bromo-4-chloroquinoline To a suspension of 7-bromoquinolin-4-ol (2.5 g, 11.16 mmol) in toluene (20 mL) was added POCl$_3$ (2.080 mL, 22.32 mmol). The reaction was heated to 100° C. After 1.5 hours, the reaction was cooled, and then ice was added. The reaction was stirred vigorously for ca. 30 min, then water was added. The reaction was extracted twice with DCM. The organic layers were washed with saturated aqueous NaHCO$_3$ and brine, then dried over sodium sulfate and concentrated. LC/MS shows that some product remains in the initial aqueous layer. The aqueous layer was stirred and saturated aqueous NaHCO$_3$ solution was added carefully. The precipitated solid was filtered off, washed with water, and dried. Material from organic layer and the filtered solid were combined and dried under high vacuum to give 7-bromo-4-chloroquinoline (2.46 g, 10.14 mmol, 91% yield). $^1$H NMR (400 MHz, CHLOROFORM-d) δ 8.80 (d, J=4.7 Hz, 1H), 8.33 (d, J=1.9 Hz, 1H), 8.12 (d, J=9.0 Hz, 1H), 7.75 (dd, J=9.0, 2.0 Hz, 1H), 7.52 (d, J=4.8 Hz, 1H).

14B. 7-bromo-4-chloroquinoline 1-oxide

To a solution of 7-bromo-4-chloroquinoline (2.0 g, 8.25 mmol) in DCM (55.0 ml) was added mCPBA (6.10 g, 24.74 mmol). The reaction was stirred overnight, then quenched with saturated sodium thiosulfate solution. The reaction was stirred for 0.5 hours, then saturated aqueous sodium bicarbonate was added. The reaction was extracted twice with methylene chloride. The organic layers were washed with brine, dried with sodium sulfate, and concentrated to give 7-bromo-4-chloroquinoline 1-oxide (2.16 g, 8.36 mmol, quantitative yield). $^1$H NMR (400 MHz, CHLOROFORM-d) δ 8.99 (d, J=1.9 Hz, 1H), 8.43 (d, J=6.6 Hz, 1H), 8.10 (d, J=9.0 Hz, 1H), 7.86 (dd, J=9.0, 2.0 Hz, 1H), 7.40 (d, J=6.6 Hz, 1H).

14C. 7-bromo-4-chloroquinolin-2-amine

In one round-bottomed flask, 7-bromo-4-chloroquinoline 1-oxide (9400 mg, 36.4 mmol) was suspended in DCM (150 mL). Ts-Cl (7626 mg, 40.0 mmol) was added. This mixture was stirred for one hour. In a second round-bottomed flask, ammonium chloride (9725 mg, 182 mmol) (dried in an oven at 110° C. overnight) was suspended in DCM (150 mL). Triethylamine (25.3 mL, 182 mmol) was added and the mixture was stirred for 0.5 hours, then the contents of the first roundbottom flask were added to the second. The reaction was stirred overnight, then filtered and concentrated. The residue was dissolved in 100 ml of hot DCM. The solution was cooled to room temperature and the solid was filtered off. The filter cake was washed with 100 mL of −20° C. DCM. The filter cake was suspended in water (50 mL) and filtered. The solid is the desired product 7-bromo-4-chloroquinolin-2-amine. The methylene chloride filtrate was evaporated, suspended in water (100 mL), and filtered. The filter cake was washed with 100 mL of −20° C. DCM to give additional product. The combined solids were dried under high vacuum to give 7-bromo-4-chloroquinolin-2-amine (6.52 g, 69.6%). $^1$H NMR (400 MHz, DMSO-d$_6$) δ 7.79 (d, J=8.7 Hz, 1H), 7.65 (d, J=1.9 Hz, 1H), 7.39 (dd, J=8.8, 2.0 Hz, 1H), 6.98 (s, 1H), 6.88 (s, 2H).

14D. 4-chloro-7-(1-(tetrahydro-2H-pyran-2-yl)-1H-pyrazol-5-yl)quinolin-2-amine

In each of two 40 mL pressure vials was placed (1-(tetrahydro-2H-pyran-2-yl)-1H-pyrazol-5-yl)boronic acid (0.714 g, 3.64 mmol), 7-bromo-4-chloroquinolin-2-amine (0.750 g, 2.91 mmol), and PdCl$_2$(dppf)-DCM adduct (0.238 g, 0.291 mmol). The vials were placed under vacuum and backfilled with nitrogen three times. Dioxane (14.56 ml) and tripotassium phosphate (2 M aqueous) (4.37 ml, 8.74 mmol) were added to each vial, nitrogen was bubbled through the solution, then the reaction was heated to 100° C. overnight. The vials were cooled, diluted with EtOAc and water, and combined. The reaction was extracted three times with EtOAc, and then the organic layers were washed with brine, dried with sodium sulfate, and concentrated. The residue was purified via ISCO (80 g column; methylene chloride/MeOH; 0 to 10% gradient) to give 4-chloro-7-(1-(tetrahydro-2H-pyran-2-yl)-1H-pyrazol-5-yl)quinolin-2-amine (1.14 g, 59.5% yield). $^1$H NMR (400 MHz, CHLOROFORM-d) δ 8.11 (d, J=8.6 Hz, 1H), 7.82 (d, J=1.4 Hz, 1H), 7.65 (d, J=1.5 Hz, 1H), 7.52 (dd, J=8.5, 1.7 Hz, 1H), 6.90 (s, 1H), 6.45 (d, J=1.8 Hz, 1H), 5.38-5.26 (m, 1H), 4.90 (br s, 1H), 4.22-4.09 (m, 2H), 3.65 (td, J=11.7, 2.3 Hz, 1H), 2.68-2.51 (m, 1H), 2.14-1.51 (m, 5H).

Example 14

To a suspension of (2r,3aR,5r,6aS)-5-aminooctahydropentalen-2-ol, HCl (54.0 mg, 0.304 mmol) and 4-chloro-7-(1-(tetrahydro-2H-pyran-2-yl)-1H-pyrazol-5-yl)quinolin-2-amine (25 mg, 0.076 mmol) in DMSO (0.5 mL) was added diisopropyethylamine (0.106 mL, 0.608 mmol). The reaction was heated to 120° C. After stirring overnight, more (2r,3aR,5r,6aS)-5-aminooctahydropentalen-2-ol, HCl (54.0 mg, 0.304 mmol) and diisopropyethylamine (0.106 mL, 0.608 mmol) were added. After an additional day, the cooled reaction was diluted with water and extracted three times with ethyl acetate. The organic layers were concentrated. The residue was then dissolved in methanol (1 mL) and 0.05 mL concentrated HCl was added. After ca. 2 hours, the reaction was concentrated, azeotroped with methylene chloride, dissolved in DMF, filtered through a syringe filter. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 2% B, 2-42% B over 25 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give (2r,3aR,5r,6aS)-5-((2-amino-7-(1H-pyrazol-5-yl)quinolin-4-yl)amino)octahydropentalen-2-ol (5.8 mg, 0.0166 mmol, 21%). HPLC RT: 1.21 min. LCMS (M+H)$^+$: 350.3 (Method C). $^1$H NMR (500 MHz, DMSO-d$_6$) δ 8.24 (br d, J=8.3 Hz, 1H), 7.90-7.84 (m, 1H), 7.83-7.77 (m, 1H), 7.76-7.68 (m, 1H), 6.82 (d, J=1.9 Hz, 1H), 5.89 (s, 1H), 4.12-4.00 (m, 1H), 3.92 (br t, J=5.9 Hz, 1H), 2.10-2.00 (m, 2H), 1.95-1.85 (m, 2H), 1.82-1.71 (m, 2H), 1.30-1.15 (m, 2H) Two protons from sidechain are not visible, likely due to overlap with DMSO peak.

Example 15. rac-N4-((1R,2S,4S)-7-oxabicyclo[2.2.1]heptan-2-yl)-7-(1H-pyrazol-5-yl)quinoline-2,4-diamine A vial was charged with 4-chloro-7-(1-(tetrahydro-2H-pyran-2-yl)-1H-pyrazol-5-yl)quinolin-2-amine (50 mg, 0.152 mmol) and rac-(1R,2S,4S)-7-oxabicyclo[2.2.1]heptan-2-amine, HCl (34.1 mg, 0.228 mmol)(see Example 1, Step 5) in NMP (0.8 mL) to give a orange solution. Diisopropylethylamine (0.159 mL, 0.912 mmol) was added, and the reaction heated at 120° C. in a heating block. After ca. 6 hours, the reaction was warmed to 130° C. and stirring was continued overnight. The cooled reaction was concentrated and then diluted with methanol (0.8 mL). A solution of HCl (4 M in dioxane, 0.380 mL, 1.521 mmol) was added. About an hour later, the reaction was diluted with methanol (0.8 mL). The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 1% B, 1-41% B over 25 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give rac-N4-((1R,2S,4S)-7-oxabicyclo[2.2.1]heptan-2-yl)-7-(1H-pyrazol-5-yl)quinoline-2,4-diamine (25.9 mg). HPLC RT: 1.01 min. LCMS (M+H)⁺: 322.3 (Method C). ¹H NMR (500 MHz, DMSO-d₆) δ 8.14 (d, J=8.5 Hz, 1H), 7.78 (s, 1H), 7.74 (br s, 1H), 7.56 (br d, J=7.6 Hz, 1H), 6.79 (d, J=2.1 Hz, 1H), 6.70-6.53 (m, 2H), 5.68 (s, 1H), 4.63 (t, J=4.6 Hz, 1H), 4.51 (d, J=4.9 Hz, 1H), 3.64-3.52 (m, 1H), 2.03 (dd, J=12.5, 7.6 Hz, 1H), 1.86 (m, 1H), 1.69-1.53 (m, 3H), 1.53-1.40 (m, 1H).

Example 16. (3-((2-amino-7-(1H-pyrazol-5-yl)quinolin-4-yl)amino)bicyclo[1.1.1]pentan-1-yl)methanol To a solution of 4-chloro-7-(1-(tetrahydro-2H-pyran-2-yl)-1H-pyrazol-5-yl)quinolin-2-amine, HCl (30 mg, 0.082 mmol) and (3-aminobicyclo[1.1.1]pentan-1-yl)methanol, HCl (42.0 mg, 0.281 mmol) in DMSO (0.5 mL) was added diisopropyethylamine (0.143 mL, 0.821 mmol). The reaction was heated to 120° C. overnight. LCMS shows that THP group was removed during reaction. The reaction was partially concentrated, diluted with methanol, and filtered through a syringe filter. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-28% B over 28 minutes, then a 5-minute hold at 100% B; Flow Rate: 20 mL/min; Column Temperature: 25 C. Fraction collection was triggered by MS signals. Fractions containing the desired product were combined and dried via centrifugal evaporation to give (3-((2-amino-7-(1H-pyrazol-5-yl)quinolin-4-yl)amino)bicyclo[1.1.1]pentan-1-yl)methanol (6.2 mg, 0.019 mmol, 22%). HPLC RT: 0.83 min. LCMS (M+H)⁺: 322.2 (Method C). ¹H NMR (500 MHz, DMSO-d₆) δ 8.06 (br d, J=8.9 Hz, 1H), 7.89-7.81 (m, 1H), 7.79 (br s, 1H), 7.76-7.71 (m, 1H), 7.68-7.60 (m, 1H), 6.81 (s, 1H), 6.12 (s, 1H), 3.54 (s, 2H), 2.05 (s, 6H).

Example 17. rac-((1R,2S,3R,4S)-3-((2-amino-7-(1H-pyrazol-5-yl)quinolin-4-yl)amino)bicyclo[2.2.1]heptan-2-yl)methanol, TFA To a suspension of rac-((1R,2S,3R,4S)-3-aminobicyclo[2.2.1]heptan-2-yl)methanol, HCl (108 mg, 0.608 mmol) and 4-chloro-7-(1-(tetrahydro-2H-pyran-2-yl)-1H-pyrazol-5-yl)quinolin-2-amine (50 mg, 0.152 mmol) in DMSO (1 mL) was added diisopropyethylamine (0.212 mL, 1.217 mmol). The reaction was heated to 120° C. overnight. The cooled reaction was concentrated and dissolved in methanol (1 mL). Some concentrated hydrochloric acid (0.05 mL) was then added and stirring continued for 2 hours. The reaction was then evaporated, dissolved in methanol and passed through a syringe filter. The crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 7% B, 7-47% B over 30 minutes, then a 4-minute hold at 100% B; Flow Rate: 20 mL/min; Column Temperature: 25 C. Fraction collection was triggered by UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 5% B, 5-45% B over 22 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give rac-((1R,2S,3R,4S)-3-((2-amino-7-(1H-pyrazol-5-yl)quinolin-4-yl)amino)bicyclo[2.2.1]heptan-2-yl)methanol (19.5 mg, 0.042 mmol, 28%) as a TFA salt. HPLC RT: 1.31 min. LCMS (M+H)⁺: 350.0 (Method C). ¹H NMR (500 MHz, DMSO-d₆) δ 8.15-8.07 (m, 1H), 7.98-7.91 (m, 1H), 7.89-7.85 (m, 1H), 7.85-7.80 (m, 1H), 7.77 (br d, J=6.7 Hz, 1H), 7.71-7.58 (m, 2H), 6.84 (d, J=1.8 Hz, 1H), 5.88 (s, 1H), 3.58 (br t, J=7.3 Hz, 1H), 3.51-3.42 (m, 1H), 2.40-2.28 (m, 2H), 2.03-1.94 (m, 1H), 1.89 (br d, J=10.1 Hz, 1H), 1.65-1.50 (m, 2H), 1.36-1.17 (m, 2H), 1.14 (s, 1H) One proton is not visible, likely due to overlap with suppressed water peak.

Examples 18A and 18B. ((2S,3R)-3-(2-amino-7-(1H-pyrazol-5-yl)quinolin-4-ylamino)bicyclo[2.2.1]heptan-2-yl)methanol and ((2R,3S)-3-(2-amino-7-(1H-pyrazol-5-yl)quinolin-4-ylamino)bicyclo[2.2.1]heptan-2-yl)methanol

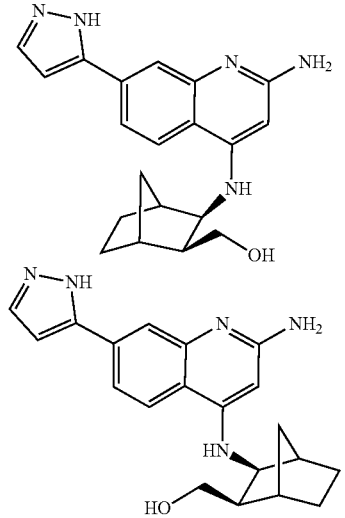

A chiral SFC separation method was developed to resolve Example 17 (17.2 mg). The sample was resolved into two peaks and collected in MeOH w/0.1% DEA using the following conditions: Chiral IC column (21×250 mm, 5 micron), 65% CO₂/35% MeOH w/0.1% DEA mobile phase, 60 mL/min flow rate. Evaporation of the product containing fractions gave the first eluting (18A) (4.6 mg) and the second eluting (18B)(4.4 mg) peaks.

Example 19 to Example 23 were prepared according to synthetic procedures similar to those described for Example 17 from the appropriate starting materials.

Example 24. 4-(3-oxa-8-azabicyclo[3.2.1]octan-8-yl)-7-(1H-pyrazol-3-yl)-1,5-naphthyridin-2-amine 24A. 2-amino-7-bromo-1,5-naphthyridin-4-ol To a stirred solution of acetonitrile (2.261 mL, 43.3 mmol) and THF (50 mL) at −78° C. was added n-butyllithium (1.967 mL, 21.64 mmol) (11.0 M in hexanes). After stirring at −78° C. for 1 h, methyl 3-amino-5-bromopicolinate (1.0 g, 4.33 mmol) in THF (30 ml), was added dropwise. The reaction was stirred at −78° C. for 30 min and then brought to room temperature. After 3 days, the reaction mixture had reached 50% completion and was then stirred at 50° C. for 5 h and 40° C. overnight reaching 85% completion with some uncyclized product, 3-(3-amino-5-bromopyridin-2-yl)-3-oxopropanenitrile, remaining. The reaction was quenched with saturated aqueous $NH_4Cl$ (15 mL), filtered under reduce pressure, and the solid was dried to afford 2-amino-7-bromo-1,5-naphthyridin-4-ol (0.85 g, 82% yield) as a tan solid. LCMS $(M+H)^+$: 240.0.

24B. 7-bromo-4-chloro-1,5-naphthyridin-2-amine

A solution of 2-amino-7-bromo-1,5-naphthyridin-4-ol (0.10 g, 0.417 mmol) in neat $POCl_3$ (1.343 mL, 14.40 mmol) was stirred at 100° C. overnight. The reaction was concentrated to remove all $POCl_3$ and azeotroped twice with MeOH to afford 7-bromo-4-chloro-1,5-naphthyridin-2-amine (0.10 g, 93% yield). LCMS $(M+H)^+$: 258.0.

24C. 4-(3-oxa-8-azabicyclo[3.2.1]octan-8-yl)-7-bromo-1,5-naphthyridin-2-amine

To a solution of 7-bromo-4-chloro-1,5-naphthyridin-2-amine (0.025 g, 0.097 mmol) and 3-oxa-8-azabicyclo[3.2.1]octane hydrochloride (0.072 g, 0.484 mmol) in NMP (0.5 ml) was added DIEA (0.169 ml, 0.967 mmol). The reaction mixture was stirred at 150° C. overnight. The reaction was complete and the subsequent Suzuki reaction was performed with this reaction mixture. LCMS $(M+H)^+$: 335.1.

Example 24

To a solution of 4-(3-oxa-8-azabicyclo[3.2.1]octan-8-yl)-7-bromo-1,5-naphthyridin-2-amine (0.032 g, 0.095 mmol) in dioxane (0.955 ml) was added potassium phosphate (0.143 ml, 0.286 mmol) (2M in water, tribasic) and 5-(4,4,5,5-tetramethyl-1,3,2-dioxaborolan-2-yl)-1H-pyrazole (0.046 g, 0.239 mmol). The mixture was purged with nitrogen/vacuum 3×. [1,1' Bis(diphenylphosphino)ferrocene]dichloropalladium(II) (3.49 mg, 4.77 μmol) was added, and the resulting solution was purged with nitrogen/vacuum and stirred overnight at 100° C. Dioxane was removed in vacuo, and the crude was dissolved in DMF and filtered for purification via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 7% B, 7-47% B over 27 minutes, then a 0-minute hold at 100% B; Flow Rate: 20 mL/min; Column Temperature: 25° C. to afford 4-(3-oxa-8-azabicyclo[3.2.1]octan-8-yl)-7-(1H-pyrazol-3-yl)-1,5-naphthyridin-2-amine (10.6 mg, 34% yield).

Example 25. 7-(1H-pyrazol-3-yl)-N4-((1-vinyl-2-oxabicyclo[2.2.2]octan-4-yl)methyl)quinoline-2,4-diamine, TFA 25A. 4-(azidomethyl)-1-vinyl-2-oxabicyclo[2.2.2]octane A solution of (1-vinyl-2-oxabicyclo[2.2.2]octan-4-yl)methyl 4-methylbenzenesulfonate (prepared as described in WO2013/003383) (1.5 g, 4.65 mmol), sodium azide (0.423 g, 6.51 mmol), and sodium iodide (0.139 g, 0.930 mmol) in DMSO (5.82 ml) was placed under nitrogen and heated at 100° C. After 2.5 h, the reaction was treated with 0.2 g more $NaN_3$ and 0.1 g more NaI, and heating was continued for another 3 h. The reaction was cooled to ambient temperature and poured into ether. The resulting mixture was washed three times with water and once with brine, dried, and concentrated under reduced pressure to afford 4-(azidomethyl)-1-vinyl-2-oxabicyclo[2.2.2]octane as a pale yellow oil. (25A, 891 mg, 99% yield). $^1HNMR$ (400 MHz, $CDCl_3$) δ 5.84 (dd, J=17.6, 10.9 Hz, 1H), 5.17 (dd, J=17.6, 1.4 Hz, 1H), 5.05 (dd, J=10.9, 1.4 Hz, 1H), 3.78 (s, 2H), 3.12 (s, 2H), 1.87-1.98 (m, 2H), 1.67-1.79 (m, 4H), 1.60-1.65 (m, 2H).

25B. (1-vinyl-2-oxabicyclo[2.2.2]octan-4-yl)methanamine, HCl, 0.5 diethyl ether

A solution of 4-(azidomethyl)-1-vinyl-2-oxabicyclo[2.2.2]octane (25A, 135 mg, 0.699 mmol) in THF (4507 μl)-Water (150 μl) was treated with triphenylphosphine (202 mg, 0.768 mmol). The resulting solution was warmed to 50° C. and stirred for 40 min., cooled to ambient temperature, and poured into EtOAc. This mixture was washed twice with 0.1 M aq. HCl, and the combined aqueous washings were concentrated under reduced pressure. Evaporation of the residue from EtOH then ether afforded (1-vinyl-2-oxabicyclo[2.2.2]octan-4-yl)methanamine, HCl, 0.5 diethyl ether as a pasty off-white solid. (25B, 165 mg, 98% yield). $^1$H-NMR (400 MHz, DMSO-d6) δ 5.79 (dd, J=17.5, 11.0 Hz, 1H), 5.10 (dd, J=17.6, 1.8 Hz, 1H), 4.96 (dd, J=10.9, 1.8 Hz, 1H), 4.35-4.61 (m, 3H), 3.67 (s, 2H), 3.45 (q, J=7.0 Hz, 2H), 2.60 (q, J=5.9 Hz, 2H), 1.68-1.74 (m, 4H), 1.58-1.64 (m, 4H), 1.06 (t, J=7.0 Hz, 2H).

25C. 7-bromo-N4-((1-vinyl-2-oxabicyclo[2.2.2]octan-4-yl)methyl)quinoline-2,4-diamine, TFA A stirred solution of (1-vinyl-2-oxabicyclo[2.2.2]octan-4-yl)methanamine, HCl, 0.5 diethyl ether (25B, 126 mg, 0.524 mmol) and 7-bromo-4-chloroquinolin-2-amine (90 mg, 0.349 mmol) in NMP (699 μl) was treated with DIEA (183 μl, 1.048 mmol). This solution was warmed to 95° C. for 5.5 h then cooled to ambient temperature. The reaction was quenched with a few drops of 50% aq. HOAc, and the resulting cloudy solution was diluted with DMF, filtered, and purified by preparative HPLC. Concentration of the appropriate fraction afforded 7-bromo-N4-((1-vinyl-2-oxabicyclo[2.2.2]octan-4-yl)methyl)quinoline-2,4-diamine, TFA (25C, 78 mg, 0.155 mmol, 44% yield) as a white powder. $^1$H-NMR (400 MHz, DMSO-d6) δ 12.38 (br. s, 1H), 8.24 (d, J=8.9 Hz, 1H), 7.97 (t, J=6.2 Hz, 1H), 7.73 (d, J=1.9 Hz, 1H), 7.70 (br. s, 2H), 7.63 (dd, J=8.8, 1.9 Hz, 1H), 5.94 (s, 1H), 5.79 (dd, J=17.5, 10.9 Hz, 1H), 5.09 (dd, J=17.6, 1.9 Hz, 1H), 4.96 (dd, J=10.9, 1.9 Hz, 1H), 3.74 (s, 2H), 3.12 (d, J=6.2 Hz, 2H), 1.62-1.76 (m, 8H).

Example 25

A mixture of 7-bromo-N4-((1-vinyl-2-oxabicyclo[2.2.2]octan-4-yl)methyl)quinoline-2,4-diamine, TFA (25C, 58 mg, 0.115 mmol), 3-(4,4,5,5-tetramethyl-1,3,2-dioxaborolan-2-yl)-1H-pyrazole (56.0 mg, 0.289 mmol), $PdCl_2$(dppf)-$CH_2Cl_2$ adduct (9.43 mg, 0.012 mmol), and cesium carbonate (113 mg, 0.346 mmol) in degassed dioxane (1.2 mL) was placed under nitrogen and heated at 95° C. for 5 h then cooled to ambient temperature. The reaction was filtered and purified by preparative HPLC (Luna C18 column, MeOH-water-TFA gradient). Concentration of the appropriate fractions afforded 7-(1H-pyrazol-3-yl)-N4-((1-vinyl-2-oxabicyclo[2.2.2]octan-4-yl)methyl)quinoline-2,4-diamine, TFA (Example 25, 35 mg, 0.072 mmol, 62% yield) as an off-white powder.

Examples 26A and 26B ($S_a$)-6-(2-amino-7-(1H-pyrazol-5-yl)quinolin-4-ylamino)spiro[3.3]heptan-2-ol and ($R_a$)-6-(2-amino-7-(1H-pyrazol-5-yl)quinolin-4-ylamino)spiro[3.3]heptan-2-ol

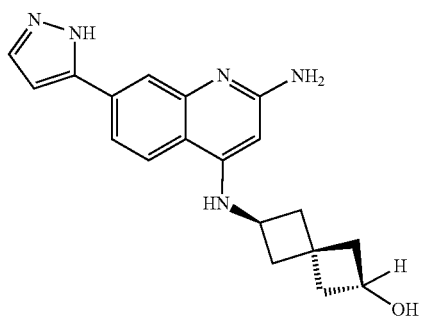

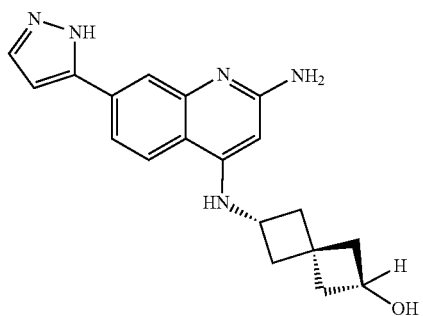

A chiral SFC separation method was developed to resolve Example 21 (32 mg). The sample was resolved into two peaks and collected in MeOH w/0.1% DEA using the following conditions: Chiralcel OJ-H column (30×250 mm, 5 micron), 90% MeOH w/0.1% DEA/10% Water-MeOH w/0.1% DEA mobile phase, 10 mL/min flow rate. Evaporation of the product containing fractions gave a first eluting (26A) (8.6 mg) and a second eluting (26B)(9.1 mg) peak.

Example 27. (rac)-tert-butyl 1-((2-amino-7-(1H-pyrazol-3-yl)quinazolin-4-yl)amino)-6-azaspiro[2.5]octane-6-carboxylate 27A: (rac)-tert-butyl 1-((2-amino-7-bromoquinazolin-4-yl)amino)-6-azaspiro[2.5]octane-6-carboxylate To a mixture of 2-amino-7-bromoquinazolin-4(1H)-one (30 mg, 0.125 mmol) and BOP (71.9 mg, 0.162 mmol) in anhydrous DMF (0.8 mL), at rt in a sealable reaction vial, was added tert-butyl 1-amino-6-azaspiro[2.5]octane-6-carboxylate (56.6 mg, 0.250 mmol) followed by 1,8-diazabicyclo[5.4.0]undec-7-ene (0.1 mL, 0.663 mmol). The resulting mixture was stirred rt overnight. Reaction was then partitioned between ethyl acetate and water. The layers were separated and the aqueous layer was extracted twice more with ethyl acetate. The combined organic layers were concentrated in vacuo to afford (rac)-tert-butyl 1-((2-amino-7-bromoquinazolin-4-yl)amino)-6-azaspiro[2.5]octane-6-carboxylate (203 mg) as a gold oil. This material was used directly in the next step.

Example 27

A mixture of tert-butyl 1-((2-amino-7-bromoquinazolin-4-yl)amino)-6-azaspiro[2.5]octane-6-carboxylate (0.056 g, 0.125 mmol), 3-(4,4,5,5-tetramethyl-1,3,2-dioxaborolane)-pyrazole (0.053 g, 0.275 mmol) and $Cs_2CO_3$ (0.122 g, 0.375 mmol) in dioxane (2.25 mL) and water (0.3 mL), at rt in a sealable reaction vial, was sparged with argon for ca. 5-10 min before $PdCl_2$(dppf)-$CH_2Cl_2$adduct (0.020 g, 0.025 mmol) was added, the vial was sealed and the reaction was heated at 90° C. After stirring overnight, the cooled reaction was partitioned between methylene chloride and water. The layers were separated and the aqueous layer was extracted twice more with methylene chloride then once with 5% methanol in methylene chloride. The organic extracts were combined and then concentrated in vacuo to afford a dark brown residue. One half of this material was purified using the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 14% B, 14-54% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give (rac)-tert-butyl 1-((2-amino-7-(1H-pyrazol-3-yl)quinazolin-4-yl)amino)-6-azaspiro[2.5]octane-6-carboxylate (12.5 mg, 0.028 mmol).

Examples 28A and 28B. tert-butyl (S)-1-((2-amino-7-(1H-pyrazol-3-yl)quinazolin-4-yl)amino)-6-azaspiro[2.5]octane-6-carboxylate and tert-butyl (R)-1-((2-amino-7-(1H-pyrazol-3-yl)quinazolin-4-yl)amino)-6-azaspiro[2.5]octane-6-carboxylate

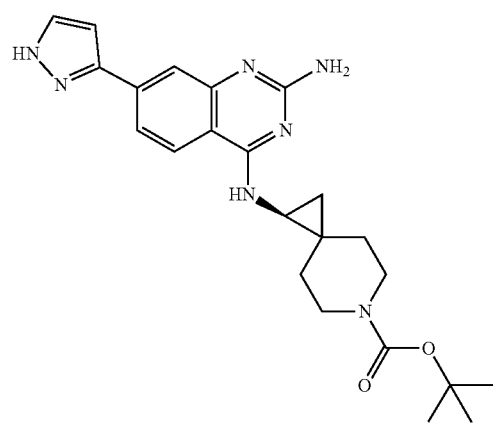

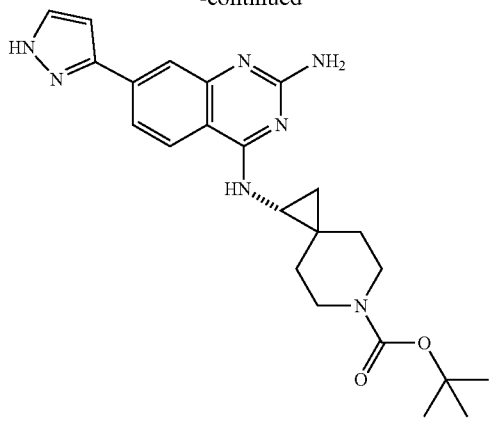

A chiral SFC separation method was developed to resolve Example 27 (13.9 mg). The sample was resolved into two peaks and collected in MeOH w/0.1% DEA using the following conditions: Chiral OD column (30×250 mm, 5 micron), 80% CO$_2$ 20% MeOH w/0.1% DEA mobile phase, 100 mL/min flow rate. Evaporation of the product containing fractions gave first eluting (28A) (2.3 mg) and a second eluting (28B)(2.4 mg) peaks.

Example 29. rac-N4-((1R,2R,4S)-7-oxabicyclo [2.2.1]heptan-2-yl)-7-(1H-pyrazol-5-yl)quinazoline-2,4-diamine 29A. rac-tert-butyl ((1R,2R,4S)-7-oxabicyclo[2.2.1] heptan-2-yl)carbamate A 25 mL round-bottomed flask was charged with rac-tert-butyl ((1R,2R,4R)-7-oxabicyclo[2.2.1]hept-5-en-2-yl)carbamate (116 mg, 0.549 mmol)(preparation described in Example 1C) and Pd/C, Degussa (29.2 mg, 0.027 mmol) in THF (4 mL) to give a black suspension. A hydrogen atmosphere was introduced via a balloon. After ca. 1 hour, the reaction was passed through a 0.45 um filter with THF rinses. The combined rinses were evaporated to give rac-tert-butyl ((1R,2R,4S)-7-oxabicyclo[2.2.1]heptan-2-yl)carbamate (106.7 mg) as a colorless oil. This material was used without purification.

29B. rac-(1R,2R,4S)-7-oxabicyclo[2.2.1]heptan-2-amine, HCl

A 20 mL vial was charged with rac-tert-butyl ((1R,2R,4S)-7-oxabicyclo[2.2.1]heptan-2-yl)carbamate (106 mg, 0.497 mmol) in methylene chloride (1 mL) to give a colorless solution. A solution of HCl in dioxane (4 M, 100 µl, 3.29 mmol) was then added and stirring continued overnight. The solvent was then evaporated and the sample dried under vacuum to give rac-(1R,2R,4S)-7-oxabicyclo [2.2.1]heptan-2-amine, HCl. This material was used without purification.

Example 29

A 4 mL vial was charged with 2-amino-7-(1-(tetrahydro-2H-pyran-2-yl)-1H-pyrazol-5-yl)quinazolin-4(3H)-one (20 mg, 0.064 mmol) and BOP (36.9 mg, 0.084 mmol) in DMF (0.5 mL) to give a suspension. DBU (0.029 mL, 0.193 mmol) was added to generate a homogenous solution. rac-(1R,2R,4S)-7-oxabicyclo[2.2.1]heptan-2-amine, HCl (14.42 mg, 0.096 mmol) was added and the reaction stirred overnight. The reaction was then diluted with water and treated with some saturated NaHCO$_3$ and 10% LiCl solutions. The mixture was extracted twice with EtOAc. The combined organic layers were then evaporated. This material was dissolved in MeOH (1 mL) and treated with a solution of HCl in dioxane (4 M, 0.032 mL, 0.128 mmol). After about 0.5 hour, the reaction was evaporated. The reaction was dissolved in methanol and made basic with DIPEA. The crude material was purified via preparative LC/MS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-minute hold at 0% B, 0-40% B over 20 minutes, then a 0-minute hold at 100% B; Flow Rate: 20 mL/min; Column Temperature: 25° C. Fraction collection was triggered by MS and UV signals. Fractions containing the desired product were combined and dried via centrifugal evaporation to give rac-N4-((1R,2R,4S)-7-oxabicyclo[2.2.1]heptan-2-yl)-7-(1H-pyrazol-5-yl) quinazoline-2,4-diamine (18.5 mg).

Example 30. rac-N4-((1R,2R,4S)-7-oxabicyclo [2.2.1]heptan-2-yl)-7-(1H-pyrazol-5-yl)quinoline-2, 4-diamine A 20 mL vial was charged with 4-chloro-7-(1-(tetrahydro-2H-pyran-2-yl)-1H-pyrazol-5-yl)quinolin-2-amine (50 mg, 0.152 mmol)(Compound 14D) and rac-(1R,2R,4S)-7-oxabicyclo[2.2.1]heptan-2-amine, HCl (59.2 mg, 0.395 mmol) (Compound 29B) in NMP (1 mL) to give a orange solution. Hunig's base (0.159 mL, 0.912 mmol) was added and the reaction heated to 130° C. After heating overnight, the cooled reaction was diluted with methanol and purified by RP-HPLC using the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-minute hold at 0% B, 0-40% B over 20 minutes, then a 0-minute hold at 100% B; Flow Rate: 20 mL/min; Column Temperature: 25° C. Fraction collection was triggered by MS and UV signals. Fractions containing the desired product were combined and dried via centrifugal evaporation to give rac-N4-((1R,2R,4S)-7-oxabicyclo[2.2.1]heptan-2-yl)-7-(1H-pyrazol-5-yl)quinoline-2,4-diamine (38.9 mg).

Examples 31A and 31B. rac-(1R,2S,4R,5S)-5-((2-amino-7-(1H-pyrazol-5-yl)quinazolin-4-yl)amino)-7-oxabicyclo[2.2.1]heptan-2-ol and rac-(1R,2S,4S, 6R)-6-((2-amino-7-(1H-pyrazol-5-yl)quinazolin-4-yl)amino)-7-oxabicyclo[2.2.1]heptan-2-ol

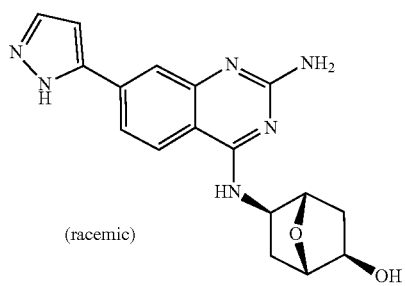

(racemic)

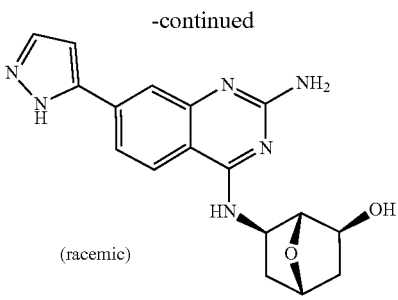

(racemic)

Step 1. rac-tert-butyl ((1R,2S,4R,5S)-5-hydroxy-7-oxabicyclo[2.2.1]heptan-2-yl)carbamate and rac-tert-butyl ((1R,2R,4S,6S)-6-hydroxy-7-oxabicyclo[2.2.1]heptan-2-yl)carbamate A 20 mL round-bottomed flask was charged with rac-tert-butyl ((1R,2S,4R)-7-oxabicyclo[2.2.1]hept-5-en-2-yl)carbamate (191 mg, 0.904 mmol)(exo-isomer from 1C) in THF (1 mL) to give a colorless solution. The reaction was cooled in an ice bath and borane-tetrahydrofuran complex (1M in THF, 2.260 mL, 2.260 mmol) was added dropwise. After ca. 15 minutes, the reaction was vented with needle and quenched very slowly with pH 7.2 buffer (1.4 mL). After this addition, hydrogen peroxide (30% aqueous 0.646 mL, 6.33 mmol) was added and stirring continued for ca. 20 minutes. The reaction was then diluted with saturated NaCl solution and extracted twice with EtOAc. The combined organic layers were cooled in an ice/water bath and saturated sodium thiosulfate solution was added. The mixture was stirred rapidly in the ice/water bath for ca. 45 minutes. The layers were then separated and the organic phase was dried over magnesium sulfate, filtered and evaporated to give rac-tert-butyl ((1R,2S,4R,5S)-5-hydroxy-7-oxabicyclo[2.2.1]heptan-2-yl)carbamate and rac-tert-butyl ((1R,2R,4S,6S)-6-hydroxy-7-oxabicyclo[2.2.1]heptan-2-yl)carbamate (191 mg total). This material was used in the next step without purification.

Step 2. rac-(1R,2S,4R,5S)-5-amino-7-oxabicyclo[2.2.1]heptan-2-ol, HCl and rac-(1R,2S,4S,6R)-6-amino-7-oxabicyclo[2.2.1]heptan-2-ol, HCl A 20 mL vial was charged with rac-tert-butyl ((1R,2S,4R,5S)-5-hydroxy-7-oxabicyclo[2.2.1]heptan-2-yl)carbamate and rac-tert-butyl ((1R,2R,4S,6S)-6-hydroxy-7-oxabicyclo[2.2.1]heptan-2-yl)carbamate (190 mg, 0.829 mmol) in THF (2 mL) to give a colorless solution. A solution of HCl in dioxane (4 M, 0.829 mL, 3.31 mmol) was added. After ca. 2 hours, an additional portion of HCl in dioxane was added and stirring continued for 3 days. The reaction was then concentrated and dried under vacuum to give rac-(1R,2S,4R,5S)-5-amino-7-oxabicyclo[2.2.1]heptan-2-ol and rac-(1R,2S,4S,6R)-6-amino-7-oxabicyclo[2.2.1]heptan-2-ol as HCl salts. This material was used in the next step without purification.

Examples 31A and 31B

A 8 mL vial was charged with 2-amino-7-(1-(tetrahydro-2H-pyran-2-yl)-1H-pyrazol-5-yl)quinazolin-4(3H)-one (50 mg, 0.161 mmol) and BOP (85 mg, 0.193 mmol) in DMF (0.6 mL). DBU (0.097 mL, 0.642 mmol) was added to give a dark red/orange solution. rac-(1R,2S,4R,5S)-5-amino-7-oxabicyclo[2.2.1]heptan-2-ol, HCl and rac-(1R,2S,4S,6R)-6-amino-7-oxabicyclo[2.2.1]heptan-2-ol, HCl (39.9 mg, 0.241 mmol) were added and stirring continued overnight. The reaction was then diluted with 10% aqueous LiCl solution and extracted three times with EtOAc. The combined organic layers were then evaporated. The residue was dissolved in EtOH (1 mL), and a solution of HCl in dioxane (4 M, 0.201 mL, 0.803 mmol) was added. After LCMS showed completion, the reaction was concentrated and redissolved in methanol for purification. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 25 minutes, then a 0-minute hold at 100% B; Flow Rate: 20 mL/min; Column Temperature: 25° C. Fraction collection was triggered by MS signals. Fractions containing the desired product were combined and dried via centrifugal evaporation. This purification was partially successful and generated two samples 31A (18.9 mg) and 31B (8.5 mg). The 31B sample appears to be one component by LCMS and 1H-NMR, while 31A is still impure with significant contamination from 31B.

Examples 32A and 32B. (1S,2R,4R,6S)-6-(2-amino-7-(1H-pyrazol-5-yl)quinolin-4-ylamino)-7-oxabicyclo[2.2.1]heptan-2-ol, (1R,2S,4R,5S)-5-(2-amino-7-(1H-pyrazol-5-yl)quinolin-4-ylamino)-7-oxabicyclo[2.2.1]heptan-2-ol, (1R,2S,4S,6R)-6-(2-amino-7-(1H-pyrazol-5-yl)quinolin-4-ylamino)-7-oxabicyclo[2.2.1]heptan-2-ol and (1S,2R,4S,5R)-5-(2-amino-7-(1H-pyrazol-5-yl)quinolin-4-ylamino)-7-oxabicyclo[2.2.1]heptan-2-ol

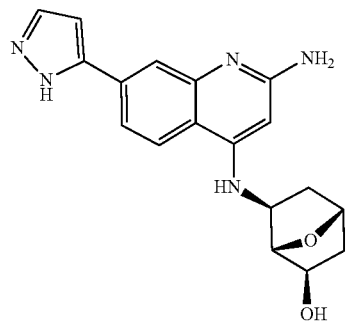

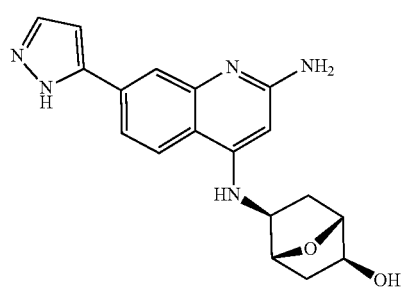

-continued

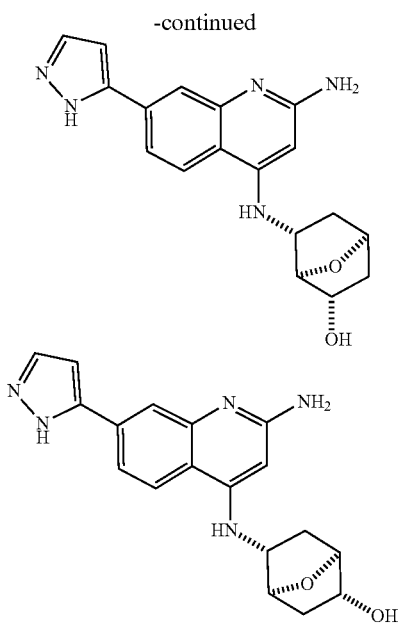

4-Chloro-7-(1-(tetrahydro-2H-pyran-2-yl)-1H-pyrazol-5-yl)quinolin-2-amine (60 mg, 0.182 mmol) and 2 rac-(1R,2S,4R,5S)-5-amino-7-oxabicyclo[2.2.1]heptan-2-ol, HCl and rac-(1R,2S,4S,6R)-6-amino-7-oxabicyclo[2.2.1]heptan-2-ol, HCl (60.4 mg, 0.365 mmol) were combined in NMP (2 mL) to give a orange solution. Hunig's base (0.191 mL, 1.095 mmol) was added and the reaction heated to 130° C. in a heating block for ca. 23 hours. The cooled reaction was diluted with 10% aqueous LiCl solution and extracted with EtOAc. The resulting emulsion was filtered and the filtrate rinsed with water and EtOAc. The aqueous layer was extracted with another portion of EtOAc. The aqueous layer was concentrated and purified by RP-HPLC using the following conditions: C18 Luna 30×100 mm eluting with a 12 min gradient from 10% B to 100% B (CH₃CN/H₂O/TFA) with 3 min hold time in 5 injections. Partial purification of the product containing peaks was achieved. One of the product containing peaks was dissolved in methanol and subjected to further purification under the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 30 minutes, then a 0-minute hold at 100% B; Flow Rate: 20 mL/min; Column Temperature: 25° C. Fraction collection was triggered by MS and UV signals. Fractions containing the desired products were combined and dried via centrifugal evaporation. As this treatment also did not result in material of sufficient purity, the material was further purified by chiral SFC using the following conditions: Column: Chiral AD, 30×250 mm, 5 micron, 100 mL/min, Oven Temperature: 40° C., 120 bar Mobile Phase: 70% CO2/30% MeOH w/0.1% DEA (isocratic), Injection: 750 uL of 20.6 mg/3 mL MeOH. This purification was partially successful and generated two samples 32A (3.9 mg)(first eluting) and 32B (2.1 mg)(second eluting). The 32B sample appears to be one component by LCMS and ¹H-NMR and is thought to be a single enantiomer of one of the regioisomeric products. The other isolate 32A is still impure and is thought to contain the racemate of the other regioisomeric product and the antipode of 32B.

Example 33. 7-(1H-pyrazol-3-yl)-N4-(1,4,8-trioxaspiro[4.5]decan-6-yl)quinoline-2,4-diamine To a solution of 4-chloro-7-(1-(tetrahydro-2H-pyran-2-yl)-1H-pyrazol-5-yl)quinolin-2-amine (50 mg, 0.152 mmol) in NMP (1 mL) was added 1,4,8-trioxaspiro[4.5]decan-6-amine (72.6 mg, 0.456 mmol) and DIEA (0.266 mL, 1.521 mmol). The reaction mixture was heated to 130° C. for 3 h. The compound was partially purified by RP-HPLC (Phen Luna 5 u 30×100 mm column, methanol-water gradient +0.1% TFA). The compound was further purified under the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 5% B, 5-45% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to give 7-(1H-pyrazol-3-yl)-N4-(1,4,8-trioxaspiro[4.5]decan-6-yl)quinoline-2,4-diamine (12.3 mg).

Example 34. (3-(((2-amino-7-(1H-pyrazol-5-yl)quinazolin-4-yl)amino)methyl) bicyclo[1.1.1]pentan-1-yl)methanol, TFA A 25 mL screw top vial was charged with (3-(aminomethyl)bicyclo[1.1.1]pentan-1-yl)methanol, HCl (24.55 mg, 0.150 mmol), 2-amino-7-(1-(tetrahydro-2H-pyran-2-yl)-1H-pyrazol-5-yl)quinazolin-4-ol (30 mg, 0.096 mmol), DBU (29.0 µl, 0.193 mmol), and BOP (85 mg, 0.193 mmol) in NMP (0.5 mL). The reaction was stirred for 16 hours, when TFA (500 µl, 6.49 mmol) was added. After 3 hours, the reaction was concentrated and dried under high vacuum. The reaction mixture was diluted with DMF:acetic acid 1:1 (1 mL). The crude material was purified via preparative LC/MS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-minute hold at 0% B, 0-40% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give (3-(((2-amino-7-(1H-pyrazol-5-yl)quinazolin-4-yl)amino)methyl)bicyclo[1.1.1]pentan-1-yl)methanol, TFA (10.4 mg, 24%).

Example 35, 37, 38, and 39 were prepared in a similar fashion to Example 9.

Examples 36A and 36B. (S)-7-(1H-pyrazol-3-yl)-N4-(spiro[2.2]pentan-1-yl)quinazoline-2,4-diamine and (R)-7-(1H-pyrazol-3-yl)-N4-(spiro[2.2]pentan-1-yl)quinazoline-2,4-diamine

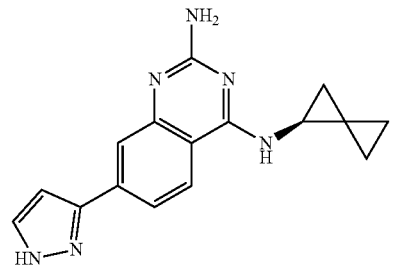

-continued

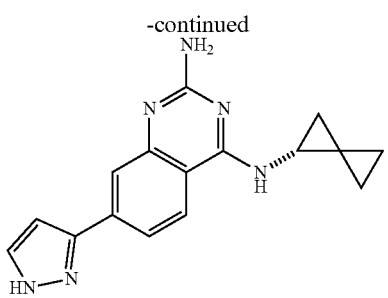

A chiral SFC separation method was developed to resolve Example 35 (ca. 7 mg). The sample was resolved into two peaks and collected in MeOH w/0.1% DEA using the following conditions: Chiral IC column (21×250 mm, 5 micron), 70% $CO_2$ 30% MeOH w/0.1% DEA mobile phase, 60 mL/min flow rate. Evaporation of the product containing fractions gave first eluting (36A) (2.3 mg) and a second eluting (36B) (2.2 mg) peaks.

Example 40. rac-(2S,6S)-6-((2-amino-7-(1H-pyrazol-5-yl)quinazolin-4-yl)amino)bicyclo[2.2.1]heptan-2-ol 40A. 8-iodohexahydro-4,6-methanocyclopenta[d][1,3]oxazin-2(1H)-one The known 8-iodohexahydro-4,6-methanocyclopenta[d][1,3]oxazin-2(1H)-one (220 mg, 0.902 mmol) (*J. Org. Chem.* 53 2665-2668 (1988), *BOMC* 12 (18) 4877-4884 (2004)) was dissolved in methylene chloride (2.6 mL). Iodine (275 mg, 1.08 mmol) was added and the reaction stirred for 3 hours. The reaction was quenched with saturated sodium thiosulfate solution and extracted three times with methylene chloride. The combined organic extracts were washed with water and dried over sodium sulfate. Filtration and evaporation provided 8-iodohexahydro-4,6-methanocyclopenta[d][1,3]oxazin-2(1H)-one (223 mg, 0.799 mmol, 88% yield). $^1$H NMR (400 MHz, CHLOROFORM-d) δ 5.23-5.16 (m, 1H), 3.86 (t, J=2.7 Hz, 1H), 3.84-3.77 (m, 1H), 2.63 (br d, J=3.7 Hz, 1H), 2.45-2.40 (m, 1H), 2.22-2.16 (m, 1H), 2.16-2.08 (m, 1H), 1.69 (dt, J=11.3, 1.5 Hz, 1H), 1.46 (dt, J=13.5, 2.7 Hz, 1H).

40B. hexahydro-4,6-methanocyclopenta[d][1,3]oxazin-2(1H)-one

8-Iodohexahydro-4,6-methanocyclopenta[d][1,3]oxazin-2(1H)-one (223 mg, 0.799 mmol) was dissolved in methanol (6659 µl). Triethylamine (200 µl, 1.438 mmol) was added, then the reaction was placed under vacuum and backfilled with nitrogen three times. After ca 3 hours, Pd—C (25 mg, 0.012 mmol) was added, then a hydrogen balloon was placed on the reaction. The reaction was placed under vacuum and backfilled with hydrogen three times. After stirring overnight, the atmosphere was exchanged for nitrogen. The reaction was filtered, rinsed with methanol, and the filtrate was concentrated. The residue was partitioned between methylene chloride and saturated sodium bicarbonate solution. The aqueous phase was extracted three times with methylene chloride. Evaporation provided hexahydro-4,6-methanocyclopenta[d][1,3]oxazin-2(1H)-one (100 mg, 0.65 mmol, 82%). $^1$H NMR (400 MHz, CHLOROFORM-d) δ 6.93 (br s, 1H), 4.83-4.66 (m, 1H), 3.75 (dt, J=4.9, 2.4 Hz, 1H), 2.40-2.31 (m, 1H), 2.26 (br s, 1H), 2.23-2.10 (m, 1H), 2.07-1.91 (m, 1H), 1.45 (s, 2H), 1.36-1.25 (m, 2H).

40C. (1S,2S,4R,6R)-6-aminobicyclo[2.2.1]heptan-2-ol

A solution of hexahydro-4,6-methanocyclopenta[d][1,3]oxazin-2(1H)-one (100 mg, 0.653 mmol) in ethanol (2332 µl) was treated with sodium hydroxide (4M aqueous) (1306 µl, 5.22 mmol). The reaction was warmed to 80° C. and stirred overnight. The reaction was partially concentrated, diluted with water, and extracted three times with methylene chloride. The organic layers were dried with sodium sulfate, filtered and concentrated to give (1S,2S,4R,6R)-6-aminobicyclo[2.2.1]heptan-2-ol (83 mg).

Example 40

To a suspension of 2-amino-7-(1-(tetrahydro-2H-pyran-2-yl)-1H-pyrazol-5-yl)quinazolin-4-ol (30 mg, 0.096 mmol) and (2S,6S)-6-aminobicyclo[2.2.1]heptan-2-ol (24.51 mg, 0.193 mmol) in DMF (0.5 mL) was added DBU (0.044 mL, 0.289 mmol) and BOP (85 mg, 0.193 mmol). After stirring overnight, the reaction was diluted with water and extracted three times with ethyl acetate. The organic layers were concentrated and the residue was dissolved in methanol (1 mL) and concentrated HCl (0.05 mL). After ca. 45 minutes, the reaction was concentrated, azeotroped with methylene chloride, dissolved in DMF, filtered through a syringe filter, and purified. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 3-minute hold at 0% B, 0-40% B over 23 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give rac-(2S,6S)-6-((2-amino-7-(1H-pyrazol-5-yl)quinazolin-4-yl)amino)bicyclo[2.2.1]heptan-2-ol (13.1 mg).

Examples 41A and 41B. (1R,2R,4S,6S)-6-((2-amino-7-(1H-pyrazol-5-yl)quinazolin-4-yl)amino)bicyclo[2.2.1]heptan-2-ol and (1S,2S,4R,6R)-6-((2-amino-7-(1H-pyrazol-5-yl)quinazolin-4-yl)amino)bicyclo[2.2.1]heptan-2-ol

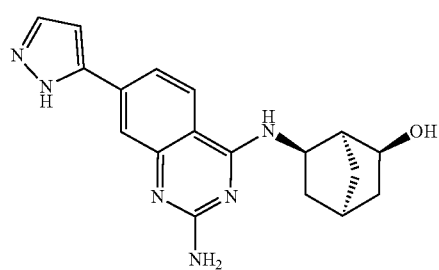

-continued

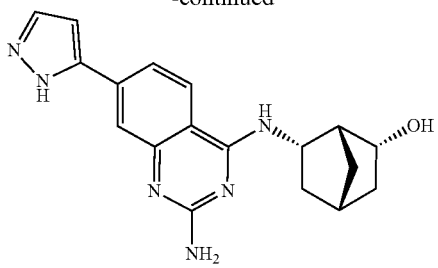

A chiral SFC separation method was developed to resolve Example 40 (11.4 mg). The sample was resolved into two peaks and collected in ethanol w/0.1% DEA using the following conditions: Chiral A5-5 column (21×250 mm, 10 micron), 75% $CO_2$ 25% EtOH w/0.1% DEA mobile phase, 45 mL/min flow rate. Evaporation of the product containing fractions gave first eluting (41A) (3.3 mg) and a second eluting (41B)(3.8 mg) peak.

Example 42. rac-(1R,2R,4S,5S)-5-((2-amino-7-(1H-pyrazol-5-yl)quinazolin-4-yl)amino)bicyclo[2.2.1] heptan-2-ol 42A. rac-methyl (1R,2R,4R,5S)-5-hydroxybicyclo [2.2.1]heptane-2-carboxylate and rac-methyl (1S, 2R,4R,6R)-6-hydroxybicyclo[2.2.1]heptane-2-carboxylate A 200 mL round-bottomed flask was charged with rac-methyl (1R,2R,4R)-bicyclo[2.2.1]hept-5-ene-2-carboxylate (2.81 g, 18.46 mmol) in THF (40 mL) to give a solution. The reaction was cooled to 0° C. A solution of BH3.THF (1M THF) (46.2 mL, 46.2 mmol) was added. After 6 hours, 1 ml of water is added slowly and hydrogen peroxide 30% (13.20 mL, 129 mmol) was then added dropwise. The reaction was partitioned between ethyl acetate (100 mL) and brine (25 mL). The organic layer was dried with sodium sulfate, filtered and concentrated. The crude product was dissolved in a small amount of methylene chloride and charged on to a 220 g silica gel cartridge and eluted with 0% to 100% ethyl acetate in hexanes. Evaporation provided rac-methyl (1R, 2R,4R,5S)-5-hydroxybicyclo[2.2.1]heptane-2-carboxylate and rac-methyl (1S,2R,4R,6R)-6-hydroxybicyclo[2.2.1] heptane-2-carboxylate (2.23 g).

42B. rac-methyl (1R,2R,4R,5S)-5-((tert-butyldiphenylsilyl)oxy)bicyclo[2.2.1]heptane-2-carboxylate and rac-methyl (1S,2R,4R,6R)-6-((tert-butyldiphenylsilyl)oxy) bicyclo[2.2.1]heptane-2-carboxylate A 100 mL round-bottomed flask was charged with a mixture of rac-methyl (1R,2R,4R,5S)-5-hydroxybicyclo [2.2.1]heptane-2-carboxylate and rac-methyl (1S,2R,4R, 6R)-6-hydroxybicyclo[2.2.1]heptane-2-carboxylate (2.23 g, 13.10 mmol) in acetonitrile (60 mL). TBDPS-Cl (5.4 mL, 21.02 mmol) was added followed by DBU (5.92 mL, 39.3 mmol). The completed reaction was partitioned between ethyl acetate (50 mL) and 1N HCl (25 mL). The organic layer was dried with sodium sulfate, filtered and concentrated. The crude product was dissolved in a small amount of methylene chloride and charged on to a 40 g silica gel cartridge and eluted with a gradient from 0% to 70% ethyl acetate in hexanes. Evaporation provided rac-methyl (1R, 2R,4R,5S)-5-((tert-butyldiphenylsilyl)oxy)bicyclo[2.2.1] heptane-2-carboxylate and rac-methyl (1S,2R,4R,6R)-6-((tert-butyldiphenylsilyl)oxy)bicyclo[2.2.1]heptane-2-carboxylate (4.19 g).

42C. rac-(1R,2R,4R,5S)-5-((tert-butyldiphenylsilyl) oxy)bicyclo[2.2.1]heptane-2-carboxylic acid and rac-(1S,2R,4R,6R)-6-((tert-butyldiphenylsilyl)oxy) bicyclo[2.2.1]heptane-2-carboxylic acid A reaction vial was charged with rac-methyl (1R,2R,4R, 5S)-5-((tert-butyldiphenylsilyl)oxy)bicyclo[2.2.1]heptane-2-carboxylate and rac-methyl (1S,2R,4R,6R)-6-((tert-butyldiphenylsilyl)oxy)bicyclo[2.2.1]heptane-2-carboxylate (500 mg, 1.224 mmol) in THF (5 mL) and methanol (5 mL). A solution of sodium hydroxide (1.63 mL, 4.89 mmol, 3 N) was added. The reaction was stirred at room temperature and eventually warmed to 50 and 60° C. When the reaction was complete, it was partitioned between methylene chloride (100 mL) and 1N HCl (50 mL). The organic layer was dried with sodium sulfate, filtered and concentrated. The crude product was dissolved in a small amount of methylene chloride and charged on to an 80 g silica gel cartridge and eluted with a gradient from 0% to 50% ethyl acetate in hexanes. Evaporation provided rac-(1S,2R,4R,6R)-6-((tert-butyldiphenylsilyl)oxy)bicyclo[2.2.1]heptane-2-carboxylic acid (149 mg) and rac-(1R,2R,4R,5S)-5-((tert-butyldiphenylsilyl)oxy)bicyclo[2.2.1]heptane-2-carboxylic acid (153 mg).

42D. rac-benzyl ((1R,2R,4R,5S)-5-((tert-butyldiphenylsilyl)oxy)bicyclo[2.2.1]heptan-2-yl)carbamate A 100 mL round-bottomed flask was charged with rac-(1R,2R,4R,5S)-5-((tert-butyldiphenylsilyl)oxy)bicyclo [2.2.1]heptane-2-carboxylic acid (640 mg, 1.622 mmol), triethylamine (0.452 mL, 3.24 mmol), and diphenylphosphoryl azide (0.438 mL, 2.027 mmol) in toluene (30 mL). After 1 hour of stirring at room temperature, benzyl alcohol (1.687 mL, 16.22 mmol) was added. The reaction was then heated at 100° C. for 16 hours. The completed reaction was then concentrated and dried under high vacuum. The crude product was dissolved in a small amount of methylene chloride and charged on to an 80 g silica gel cartridge and eluted with a 0% to 70% ethyl acetate in hexanes gradient. Evaporation provided rac-benzyl ((1R,2R,4R,5S)-5-((tert-butyldiphenylsilyl)oxy) bicyclo[2.2.1]heptan-2-yl)carbamate (811 mg, 84%).

42E. rac-benzyl ((1R,2R,4R,5S)-5-hydroxybicyclo [2.2.1]heptan-2-yl)carbamate

A reaction vial was charged with rac-benzyl ((1R,2R,4R, 5S)-5-((tert-butyldiphenylsilyl)oxy)bicyclo[2.2.1]heptan-2-yl)carbamate (683 mg, 1.367 mmol) and TBAF (1M THF) (5.47 mL, 5.47 mmol) in THF (20 mL). After 16 hours, the crude product was dissolved in methylene chloride, evaporated onto silica gel and charged to a solid sample cartridge (25 g) and dried under vacuum. The sample was then eluted onto a 40 g silica gel cartridge which was then eluted with 0% to 100% ethyl acetate in hexanes gradient. Evaporation provided rac-benzyl ((1R,2R,4R,5S)-5-hydroxybicyclo [2.2.1]heptan-2-yl)carbamate (350 mg).

42F. rac-(1R,2S,4R,5R)-5-aminobicyclo[2.2.1]heptan-2-ol

A 100 mL round-bottomed flask was charged with rac-benzyl ((1R,2R,4R,5S)-5-hydroxybicyclo[2.2.1]heptan-2- yl)carbamate (175 mg, 0.670 mmol) in methanol (20 mL). Pd—C (71.3 mg, 0.067 mmol) was added and a hydrogen atmosphere was introduced. After 16 hours, the completed reaction was purged 3 times with vacuum and nitrogen and filtered on celite. Evaporation provided rac-(1R,2S,4R,5R)-5-aminobicyclo[2.2.1]heptan-2-ol (66 mg) which was used without purification.

Example 42

A 25 mL round-bottomed flask was charged with rac-(1R, 2S,4R,5R)-5-aminobicyclo[2.2.1]heptan-2-ol (61.3 mg, 0.482 mmol) and 2-amino-7-(1-(tetrahydro-2H-pyran-2-yl)-1H-pyrazol-5-yl)quinazolin-4-ol (50 mg, 0.161 mmol) in NMP (1 mL). DBU (72.6 µl, 0.482 mmol) and BOP (142 mg, 0.321 mmol) were added and the reaction was stirred for 16 hours. TFA (500 µl, 6.49 mmol) was then added and the reaction stirred for an additional 4 hours. The reaction was diluted with methanol and neutralized with sodium carbonate. The sample was filtered and evaporated. The crude material was purified via preparative LC/MS with the following conditions: Column: XBridge C18, 200 mm×19 mm, 5-µm particles; Mobile Phase A: 5:95 acetonitrile:water with 0.05% trifluoroacetic acid; Mobile Phase B: 95:5 acetonitrile:water with 0.05% trifluoroacetic acid; Gradient: a 5-minute hold at 0% B, 0-30% B over 25 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give rac-(1R, 2R,4S,5S)-5-((2-amino-7-(1H-pyrazol-5-yl)quinazolin-4-yl)amino)bicyclo[2.2.1]heptan-2-ol (22 mg).

Examples 43A and 43B. (1S,2R,4S,5S)-5-((2-amino-7-(1H-pyrazol-5-yl)quinazolin-4-yl)amino) bicyclo[2.2.1]heptan-2-ol and (1R,2S,4R,5R)-5-((2-amino-7-(1H-pyrazol-5-yl)quinazolin-4-yl)amino) bicyclo[2.2.1]heptan-2-ol

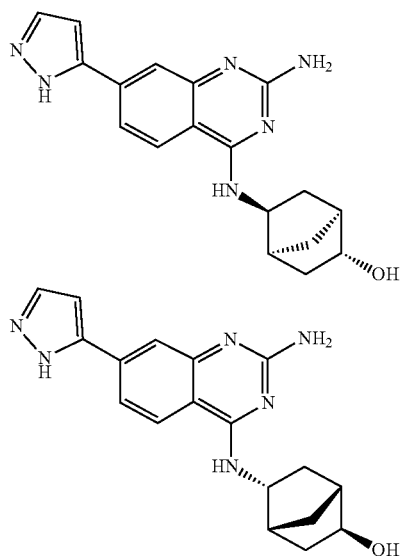

A chiral SFC separation method was developed to resolve Example 42 (18.8 mg). The sample was resolved into two peaks and collected in MeOH w/0.1% DEA using the following conditions: Chiral OJ column (30×250 mm, 5 micron), 60% CO$_2$ 40% MeOH w/0.1% DEA mobile phase, 45 mL/min flow rate. Evaporation of the product containing fractions gave first eluting (43A) (7.6 mg) and a second eluting (43B)(5.0 mg) peak.

Example 44. rac-(1R,2S,4S,6S)-6-((2-amino-7-(1H-pyrazol-5-yl)quinazolin-4-yl)amino)bicyclo[2.2.1] heptan-2-ol The second acid from 42C, rac-(1S,2R,4R,6R)-6-((tert-butyldiphenylsilyl)oxy) bicyclo[2.2.1]heptane-2-carboxylic acid, was processed as described in Example 42 to give the title compound.

Example 45A and 45B. (1R,2S,4S,6S)-6-((2-amino-7-(1H-pyrazol-5-yl)quinazolin-4-yl)amino)bicyclo [2.2.1]heptan-2-ol and (1S,2R,4R,6R)-6-((2-amino-7-(1H-pyrazol-5-yl)quinazolin-4-yl)amino)bicyclo [2.2.1]heptan-2-ol

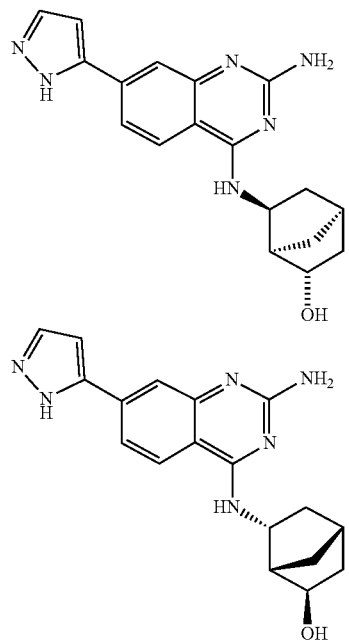

A chiral SFC separation method was developed to resolve Example 44 (13.4 mg). The sample was resolved into two peaks and collected in MeOH w/0.1% DEA using the following conditions: Chiral IC column (21×250 mm, 5 micron), 65% CO$_2$ 35% MeOH w/0.1% DEA mobile phase, 60 mL/min flow rate. Evaporation of the product containing fractions gave first eluting (45A) (3.6 mg) and a second eluting (45B)(3.9 mg) peak.

Example 46. rac-(1S,2S,4R,6R)-6-((2-amino-7-(1H-pyrazol-5-yl)quinolin-4-yl)amino)bicyclo[2.2.1]heptan-2-ol To a solution of 4-chloro-7-(1-(tetrahydro-2H-pyran-2-yl)-1H-pyrazol-5-yl)quinolin-2-amine, HCl (30 mg, 0.082 mmol) and Hunig's Base (0.057 mL, 0.329 mmol) in DMSO (0.5 mL) was added rac-(1S,2S,4R,6R)-6-aminobicyclo [2.2.1]heptan-2-ol (25 mg, 0.197 mmol). The reaction was heated initially to 110° C. and then to 120° C. The reaction was partially concentrated and cooled. The residue was dissolved in 1 mL methanol and 0.05 mL conc. HCl was added. After ca. 4 hours, the reaction was concentrated and azeotroped with methanol. The reaction was dissolved in DMF and passed through a syringe filter. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 5% B, 5-45% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give rac-(1S, 2S,4R,6R)-6-((2-amino-7-(1H-pyrazol-5-yl)quinolin-4-yl) amino)bicyclo[2.2.1]heptan-2-ol (4.1 mg).

Example 47. 4-((2-oxabicyclo[2.2.2]octan-4-yl) methoxy)-7-(1H-pyrazol-3-yl)quinolin-2-amine A reaction vial was charged with 7-bromo-4-chloroquinolin-2-amine (40 mg, 0.155 mmol), (2-oxabicyclo[2.2.2] octan-4-yl)methanol (66.3 mg, 0.466 mmol), and potassium t-butoxide (1 M in THF, 0.39 mL, 0.39 mmol) in DMSO (0.78 mL). The vial was sealed and heated to 120° C. for 2 hours. The cooled reaction was then purified by RP-HPLC (methanol-water gradient +0.1% TFA). Evaporation of the product containing fractions gave 4-((2-oxabicyclo[2.2.2] octan-4-yl)methoxy)-7-bromoquinolin-2-amine as an off-white solid. HPLC RT: 0.71 min. LCMS (M+H)$^+$: 365.1 (Method C). This material (15 mg, 0.041 mmol) was combined with 5-(4,4,5,5-tetramethyl-1,3,2-dioxaborolan-2-yl)-1H-pyrazole (20.03 mg, 0.103 mmol) in degassed dioxane (0.41 mL). Cesium carbonate (53.8 mg, 0.165 mmol) and PdCl$_2$(dppf)-CH$_2$Cl$_2$ adduct (6.74 mg, 8.26 µmol) were added and the reaction placed under nitrogen. The reaction was then heated at 95° C. for one hour. The cooled reaction was quenched with a few drops of 1:1 acetic acid-water and diluted with DMF (2 mL). The sample was then purified via preparative LC/MS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-minute hold at 11% B, 11-51% B over 25 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give 4-((2-oxabicyclo[2.2.2]octan-4-yl) methoxy)-7-(1H-pyrazol-3-yl)quinolin-2-amine (3.9 mg, 25%).

Example 48. N4-((2-oxabicyclo[2.2.2]octan-4-yl) methyl)-7-(1H-pyrazol-3-yl)quinoline-2,4-diamine 48A. (4-hydroxycyclohexane-1,1-diyl)bis(methylene)bis(4-methylbenzenesulfonate)

A solution of the known (4-oxocyclohexane-1,1-diyl)bis (methylene)bis(4-methylbenzenesulfonate) (1.35 g, 2.89 mmol) (*ACS Med. Chem. Lett.* 5(5) 609-614 (2014)) in methylene chloride (6 mL) was cooled to −40° C. and treated with a solution of DIBAL-H (3.47 mL, 3.47 mmol, 1 M) in hexanes. After stirring for 30 minutes, the reaction was warmed to ~−20° C. More DIBAL-H (0.5 mL) was added and stirring continued for 30 minutes. More DIBAL-H (0.5 mL) was added and stirring continued for 15 minutes. The reaction was then quenched with Rochelle salt solution and extracted with methylene chloride. Drying, filtration and evaporation provided the crude product (4-hydroxycyclohexane-1,1-diyl)bis(methylene)bis(4-methylbenzenesulfonate) (1.25 g). $^1$H NMR (400 MHz, DMSO-d$_6$) δ 7.74 (dd, J=8.3, 6.8 Hz, 4H), 7.54-7.43 (m, 4H), 4.49 (d, J=4.1 Hz, 1H), 3.84 (s, 2H), 3.75 (s, 2H), 3.43-3.35 (m, 1H), 2.44 (d, J=1.8 Hz, 6H), 1.44 (br dd, J=9.4, 5.9 Hz, 4H), 1.16-1.02 (m, 4H).

48B. (2-oxabicyclo[2.2.2]octan-4-yl)methyl 4-methylbenzenesulfonate

A solution of (4-hydroxycyclohexane-1,1-diyl)bis(methylene)bis(4-methylbenzenesulfonate) (1.1 g, 2.348 mmol) in DME (47.0 ml) was treated with sodium hydride (0.282 g, 7.04 mmol, 60% oil dispersion) and heated to reflux. After 1 hour, TLC indicated that the reaction was done. The reaction was cooled to ~10° C. and quenched with aqueous ammonium chloride solution. The resulting mixture was extracted with 1:1 ethyl acetate-hexane and then dichloromethane. The combined organic extracts were washed with brine, dried, and stripped to afford a pale yellow oil. This was purified by flash silica gel chromatography (10-40% ethyl acetate-hexane). Concentration of the appropriate fractions afforded (2-oxabicyclo[2.2.2]octan-4-yl)methyl 4-methylbenzenesulfonate (600 mg, 2.024 mmol, 86% yield) as a colorless oil. $^1$H NMR (400 MHz, DMSO-d$_6$) δ 7.78 (d, J=8.3 Hz, 2H), 7.54-7.45 (m, 2H), 3.70 (s, 2H), 3.66 (tt, J=3.8, 1.7 Hz, 1H), 3.46 (t, J=1.3 Hz, 2H), 2.43 (s, 3H), 1.88-1.76 (m, 2H), 1.62-1.32 (m, 6H).

48C. 4-(azidomethyl)-2-oxabicyclo[2.2.2]octane

A solution of (2-oxabicyclo[2.2.2]octan-4-yl)methyl 4-methylbenzenesulfonate (590 mg, 1.991 mmol) in DMSO (4977 µl) was treated with sodium azide (233 mg, 3.58 mmol) and sodium iodide (59.7 mg, 0.398 mmol). The resulting suspension was placed under nitrogen and heated at 90° C. overnight. The reaction was cooled to RT and poured into ether. This mixture was washed twice with water and once with brine, dried, and stripped to afford 4-(azidomethyl)-2-oxabicyclo[2.2.2]octane (295 mg, 1.764 mmol, 89% yield) as a colorless oil. $^1$H NMR (400 MHz, CHLOROFORM-d) δ 3.82 (t, J=4.0 Hz, 1H), 3.70 (t, J=1.5 Hz, 2H), 3.07 (s, 2H), 2.13-2.01 (m, 2H), 1.72-1.69 (m, 1H), 1.72-1.55 (m, 6H).

48D. (2-oxabicyclo[2.2.2]octan-4-yl)methanamine, HCl

A solution of 4-(azidomethyl)-2-oxabicyclo[2.2.2]octane (300 mg, 1.794 mmol) in ethanol (5980 µl) was placed under nitrogen and treated with Pd—C(191 mg, 0.179 mmol, 10%). This mixture was then placed under vacuum and then an atmosphere of hydrogen was introduced. HCl (493 µl, 1.974 mmol, 4 M) in dioxane was added, and the reaction was stirred at RT overnight. The reaction was diluted with methylene chloride and treated with a little magnesium sulfate. The reaction was stirred briefly and then filtered. The filtrate was diluted with chloroform and washed with water. The aqueous phase (pH~2) was stripped to afford a glass. This was dissolved in 1:1 EtOH-DCM and stripped to afford a tan solid (300 mg). $^1$H NMR (400 MHz, DMSO-d$_6$) δ 7.92

(br s, 3H), 3.69 (t, J=3.9 Hz, 1H), 3.58 (s, 2H), 3.33 (s, 2H), 1.95-1.79 (m, 2H), 1.65-1.48 (m, 6H).

48E. N4-((2-oxabicyclo[2.2.2]octan-4-yl)methyl)-7-bromoquinoline-2,4-diamine, TFA A solution of 7-bromo-4-chloroquinolin-2-amine (150 mg, 0.582 mmol) and (2-oxabicyclo[2.2.2]octan-4-yl)methanamine, HCl (155 mg, 0.874 mmol) in NMP (1456 µl) was treated with DIPEA (407 µl, 2.330 mmol). The reaction was placed under nitrogen, and heated at 135° C. After 5 hours, the temperature was reduced to 125° C. and stirring continued overnight. The reaction was cooled to RT and treated with DMF and a little acetic acid to give a solution. Purification by preparative HPLC (methanol-water gradient +0.1% TFA) afforded, after concentration, N4-((2-oxabicyclo[2.2.2]octan-4-yl)methyl)-7-bromoquinoline-2,4-diamine, TFA (89 mg, 0.187 mmol, 32.1% yield) as an off-white solid. $^1$H NMR (400 MHz, DMSO-d$_6$) δ 12.70 (br s, 1H), 8.24 (d, J=8.9 Hz, 1H), 7.95 (br t, J=6.0 Hz, 1H), 7.83 (br s, 2H), 7.71 (d, J=1.7 Hz, 1H), 7.61 (dd, J=8.8, 1.6 Hz, 1H), 5.94 (s, 1H), 3.74-3.61 (m, 3H), 3.08 (br d, J=6.0 Hz, 2H), 1.96-1.79 (m, 2H), 1.70-1.51 (m, 6H).

Example 48

A suspension of 5-(4,4,5,5-tetramethyl-1,3,2-dioxaborolan-2-yl)-1H-pyrazole (18.33 mg, 0.094 mmol), N4-((2-oxabicyclo[2.2.2]octan-4-yl)methyl)-7-bromoquinoline-2,4-diamine, TFA (18 mg, 0.038 mmol), cesium carbonate (43.1 mg, 0.132 mmol), and PdCl$_2$(dppf)-CH$_2$Cl$_2$ adduct (4.63 mg, 5.67 µmol) in degassed dioxane (378 µl) was placed under nitrogen and heated at 95° C. for 5 hours. The reaction was cooled to RT, quenched with aqueous acetic acid and diluted to 2 mL with DMF. The crude material was purified via preparative LC/MS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-minute hold at 3% B, 3-43% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give N4-((2-oxabicyclo[2.2.2]octan-4-yl)methyl)-7-(1H-pyrazol-3-yl)quinoline-2,4-diamine (9.5 mg, 72%).

Example 49. N4-((2-oxabicyclo[2.2.2]octan-4-yl)methyl)-7-(thiophen-3-yl)quinoline-2,4-diamine A suspension of thiophen-3-ylboronic acid (7.25 mg, 0.057 mmol), N4-((2-oxabicyclo[2.2.2]octan-4-yl)methyl)-7-bromoquinoline-2,4-diamine, TFA (18 mg, 0.038 mmol, from 48E), cesium carbonate (43.1 mg, 0.132 mmol), and PdCl$_2$(dppf)-CH$_2$Cl$_2$ adduct (4.63 mg, 5.67 µmol) in degassed dioxane (378 µl) was placed under nitrogen and heated at 95° C. for 2 hours. The reaction was cooled to RT, quenched with aqueous acetic acid and diluted to 2 mL with DMF. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 13% B, 13-53% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give N4-((2-oxabicyclo[2.2.2]octan-4-yl)methyl)-7-(thiophen-3-yl)quinoline-2,4-diamine (9.7 mg, 69%).

Example 50. methyl 4-(((2-amino-7-(1H-pyrazol-3-yl)quinolin-4-yl)amino)methyl)bicyclo[2.2.2]octane-1-carboxylate

50A. methyl 4-((tosyloxy)methyl)bicyclo[2.2.2]octane-1-carboxylate

A solution of methyl 4-(hydroxymethyl)bicyclo[2.2.2]octane-1-carboxylate (0.25 g, 1.261 mmol) in pyridine (1.261 ml) was treated with Ts-Cl (0.245 g, 1.286 mmol) and stirred for one day. More TsCl (0.2 g) was added, and stirring was continued for another day. The reaction was transferred into 70 mL of 10% aq. HOAc with stirring. The resulting precipitate was filtered, rinsed with water then 10% EtOAc-hexane, and air-dried to afford methyl 4-((tosyloxy)methyl)bicyclo[2.2.2]octane-1-carboxylate (320 mg, 0.908 mmol, 72.0% yield) as a white powder. $^1$H NMR (400 MHz, CHLOROFORM-d) δ 7.79 (d, J=8.3 Hz, 2H), 7.37 (d, J=8.0 Hz, 2H), 3.67 (s, 2H), 3.65 (s, 3H), 2.48 (s, 3H), 1.82-1.74 (m, 6H), 1.49-1.40 (m, 6H).

50B. methyl 4-(azidomethyl)bicyclo[2.2.2]octane-1-carboxylate

A mixture of methyl 4-((tosyloxy)methyl)bicyclo[2.2.2]octane-1-carboxylate (310 mg, 0.880 mmol), sodium azide (172 mg, 2.64 mmol), and sodium iodide (39.6 mg, 0.264 mmol) in DMSO (1759 µl) was placed under nitrogen and heated at 100° C. The reaction was heated for 4 hours at 100° C., then the temperature was lowered to 90° C. The next day, the reaction was cooled to RT and diluted with ether. The resulting mixture was washed three times with water and once with brine, dried, and stripped to afford methyl 4-(azidomethyl)bicyclo[2.2.2]octane-1-carboxylate (190 mg, 0.851 mmol, 97% yield) as a colorless oil. $^1$H NMR (400 MHz, CHLOROFORM-d) δ 3.67 (s, 3H), 3.06 (s, 2H), 1.88-1.77 (m, 6H), 1.52-1.43 (m, 6H).

50C. methyl 4-(aminomethyl)bicyclo[2.2.2]octane-1-carboxylate, HCl, 0.5 ethanol A solution of methyl 4-(azidomethyl)bicyclo[2.2.2]octane-1-carboxylate (0.19 g, 0.851 mmol) in ethanol (5 mL) was placed under nitrogen then charged with palladium on carbon (0.181 g, 0.170 mmol). This mixture was then treated with HCl (0.213 mL, 0.851 mmol, 4 M) in dioxane. The reaction was treated with hydrogen at an atmosphere for 3 hours. The reaction was diluted with methylene chloride, stirred briefly with a little magnesium sulfate, and then the catalyst was removed by filtration. The resulting solution was concentrated under reduced pressure to afford methyl 4-(aminomethyl)bicyclo[2.2.2]octane-1-carboxylate, HCl, 0.5 ethanol (215 mg, 0.837 mmol, 98% yield) as a waxy white solid.

50D. methyl 4-(((2-amino-7-bromoquinolin-4-yl)amino)methyl)bicyclo[2.2.2]octane-1-carboxylate, TFA, ethanol A mixture of 7-bromo-4-chloroquinolin-2-amine (132 mg, 0.511 mmol), methyl 4-(aminomethyl)bicyclo[2.2.2]

octane-1-carboxylate, HCl, 0.5 ethanol (210 mg, 0.818 mmol), and DIEA (357 µl, 2.045 mmol) in N-Methyl-2-pyrrolidinone (2045 µl) was heated to 100° C. for 1 hour, 120° C. for 2.5 hours, and finally 135° C. for 6 days. The reaction was then cooled and poured into aqueous acetic acid. The resulting mixture was brought to pH~7 with aqueous sodium bicarbonate. This mixture was extracted twice with 5% EtOH-CHCl$_3$, and the combined organic extracts dried, stripped, and purified by RP-HPLC (methanol-water gradient +0.1% TFA). Concentration of the appropriate fractions afforded methyl 4-(((2-amino-7-bromoquinolin-4-yl)amino)methyl) bicyclo[2.2.2]octane-1-carboxylate, TFA, ethanol (137 mg, 0.237 mmol, 46.3% yield) as a tan powder. $^1$H NMR (400 MHz, DMSO-d$_6$) δ 12.29 (s, 1H), 8.26 (d, J=9.0 Hz, 1H), 7.93 (br t, J=6.1 Hz, 1H), 7.73 (d, J=2.0 Hz, 1H), 7.65 (br s, 1H), 7.62 (dd, J=8.9, 2.0 Hz, 1H), 5.95 (s, 1H), 3.57 (s, 2H), 3.08 (br d, J=6.2 Hz, 1H), 1.78-1.66 (m, 4H), 1.57-1.46 (m, 4H).

Example 50

A mixture of 3-(4,4,5,5-tetramethyl-1,3,2-dioxaborolan-2-yl)-1H-pyrazole (15.10 mg, 0.078 mmol), methyl 4-(((2-amino-7-bromoquinolin-4-yl)amino)methyl) bicyclo[2.2.2] octane-1-carboxylate, TFA, ethanol (18 mg, 0.031 mmol), PdCl$_2$(dppf)-CH$_2$Cl$_2$ adduct (5.08 mg, 6.22 µmol), and cesium carbonate (30.4 mg, 0.093 mmol) in degassed dioxane (311 µl) was treated with 10 µL of water and placed under nitrogen. The resulting mixture was heated at 95° C. The reaction was then cooled to RT, brought to pH~5 with aqueous acetic acid, and filtered. The crude material was purified via preparative LC/MS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-minute hold at 14% B, 14-54% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give methyl 4-(((2-amino-7-(1H-pyrazol-3-yl)quinolin-4-yl)amino)methyl) bicyclo[2.2.2]octane-1-carboxylate (11.9 mg, 93%).

Example 51. (4-(((2-amino-7-(thiophen-3-yl)quinolin-4-yl)amino)methyl)-2-oxabicyclo[2.2.2]octan-1-yl)methanol 51A. (4-hydroxy-4-vinylcyclohexane-1,1-diyl)bis(methylene)bis(4-methylbenzenesulfonate)

A solution of vinylmagnesium bromide (16.85 ml, 16.85 mmol, 1 M) in THF was cooled to −78° C. This was treated over 20 minutes with a solution of (4-oxocyclohexane-1,1-diyl)bis(methylene)bis(4-methylbenzenesulfonate) (3.93 g, 8.42 mmol) in THF (24.07 ml). The reaction was stirred for 2 hours and then warmed to 0° C. The reaction was quenched with aqueous acetic acid. The resulting mixture was stirred briefly then extracted with 1:1 ethyl acetate-hexane. The organic extract was washed with brine, dried, and concentrated under reduced pressure to afford an oil. This material was purified on silica gel (50-90% ether-hexane). Concentration of the appropriate fractions afforded (4-hydroxy-4-vinylcyclohexane-1,1-diyl)bis(methylene)bis(4-methylbenzenesulfonate) (3.21 g, 6.49 mmol, 77% yield) as a colorless glass which solidified upon standing. $^1$H NMR (400 MHz, DMSO-d$_6$) δ 7.76 (dd, J=10.9, 8.3 Hz, 4H), 7.52-7.45 (m, 4H), 5.79 (dd, J=17.3, 10.7 Hz, 1H), 5.05 (dd, J=17.4, 1.9 Hz, 1H), 4.90 (dd, J=10.7, 1.9 Hz, 1H), 4.34 (s, 1H), 3.91 (s, 2H), 3.71 (s, 2H), 3.32 (s, 2H), 2.44 (s, 3H), 2.43 (s, 3H), 1.54-1.38 (m, 2H), 1.26-1.09 (m, 6H).

51B. (1-vinyl-2-oxabicyclo[2.2.2]octan-4-yl)methyl 4-methylbenzenesulfonate

A solution of (4-hydroxy-4-vinylcyclohexane-1,1-diyl) bis(methylene)bis(4-methylbenzenesulfonate) (3.2 g, 6.47 mmol) in DME (216 ml) was treated with sodium hydride (0.518 g, 12.94 mmol) and heated to reflux for 2 hours. The reaction was cooled to RT and quenched with aqueous ammonium chloride solution. The resulting mixture was extracted with 1:1 ethyl acetate-hexane, and the organic extract was washed with brine, dried, stripped, and chromatographed on silica gel (10-30% ethyl acetate-hexane). Concentration of the appropriate fractions afforded (1-vinyl-2-oxabicyclo[2.2.2]octan-4-yl)methyl 4-methylbenzenesulfonate (1.83 g, 5.68 mmol, 88% yield) as a colorless solid. $^1$H NMR (400 MHz, CHLOROFORM-d) δ 7.76 (d, J=8.4 Hz, 2H), 7.35 (d, J=7.9 Hz, 2H), 5.78 (dd, J=17.6, 10.9 Hz, 1H), 5.12 (dd, J=17.6, 1.4 Hz, 1H), 5.01 (dd, J=10.9, 1.4 Hz, 1H), 3.70 (s, 2H), 3.68 (t, J=1.4 Hz, 2H), 2.45 (s, 3H), 1.91-1.80 (m, 2H), 1.75-1.60 (m, 4H), 1.53-1.45 (m, 2H).

51C. 4-(azidomethyl)-1-vinyl-2-oxabicyclo[2.2.2]octane

A solution of (1-vinyl-2-oxabicyclo[2.2.2]octan-4-yl) methyl 4-methylbenzenesulfonate (1.5 g, 4.65 mmol), sodium azide (0.423 g, 6.51 mmol), and sodium iodide (0.139 g, 0.930 mmol) in DMSO (2.326 ml) was placed under nitrogen and heated at 100° C. for 2.5 hours. The temperature was lowered to 90° C. and stirring continued overnight. The reaction was cooled and diluted with ether. The extract was washed three times with water and once with brine. Drying and evaporation afforded a yellow oil. This material was purified by flash silica gel chromatography (10-30% ethyl acetate-hexane). Concentration of the appropriate fractions afforded 4-(azidomethyl)-1-vinyl-2-oxabicyclo[2.2.2]octane (560 mg, 2.90 mmol, 62.3% yield) as a colorless oil. $^1$H NMR (400 MHz, CHLOROFORM-d) δ 5.81 (dd, J=17.6, 10.9 Hz, 1H), 5.15 (dd, J=17.5, 1.4 Hz, 1H), 5.03 (dd, J=10.9, 1.4 Hz, 1H), 3.76 (t, J=1.5 Hz, 2H), 3.09 (s, 2H), 1.98-1.85 (m, 2H), 1.78-1.65 (m, 4H), 1.64-1.55 (m, 2H).

51D. (1-vinyl-2-oxabicyclo[2.2.2]octan-4-yl)methanamine, HCl

A solution of 4-(azidomethyl)-1-vinyl-2-oxabicyclo [2.2.2]octane (510 mg, 2.64 mmol) in THF (17 mL)-water (0.57 mL) was treated with triphenylphosphine (692 mg, 2.64 mmol) and stirred. The reaction was already bubbling slightly at RT. The reaction was then warmed to 50° C. and stirred for ~2 hours. The cooled reaction was poured into 1:1 ethyl acetate-hexane. This mixture was washed three times with 0.1 M aqueous HCl, and the combined washings stripped on the rotoevaporator. Evaporation from ethanol and then methylene chloride afforded a white solid (630 mg). $^1$H NMR (400 MHz, DMSO-d$_6$) δ 8.01 (br s, 3H), 5.79 (dd, J=17.5, 11.0 Hz, 1H), 5.10 (dd, J=17.5, 1.8 Hz, 1H), 4.96 (dd, J=10.9, 1.8 Hz, 1H), 3.67 (s, 2H), 2.60 (q, J=5.9 Hz, 2H), 1.76-1.66 (m, 4H), 1.65-1.53 (m, 4H).

51E. 7-bromo-N4-((1-vinyl-2-oxabicyclo[2.2.2]octan-4-yl)methyl)quinoline-2,4-diamine, TFA A solution of 7-bromo-4-chloroquinolin-2-amine (506 mg, 1.964 mmol), (1-vinyl-2-oxabicyclo[2.2.2]octan-4-yl) methanamine, HCl (600 mg, 2.95 mmol), and Hunig's base (1029 µl, 5.89 mmol) in N-Methyl-2-pyrrolidinone (1964 µl) was degassed and placed under nitrogen. The reaction was heated at 120° C. for 3 hours. Subsequently, the reaction was heated to 135° C. until LCMS showed completion. The crude material was purified by RP-HPLC (methanol-water gradient +0.1% TFA) to afford 7-bromo-N4-((1-vinyl-2-oxabicyclo[2.2.2]octan-4-yl)methyl)quinoline-2,4-diamine, TFA (700 mg, 1.394 mmol, 71.0% yield) as an off-white solid. $^1$H NMR (400 MHz, DMSO-$d_6$) δ 12.33 (s, 1H), 8.24 (d, J=9.0 Hz, 1H), 7.97 (br t, J=6.4 Hz, 1H), 7.74 (d, J=2.0 Hz, 1H), 7.69 (br s, 1H), 7.63 (dd, J=8.9, 2.0 Hz, 1H), 5.94 (s, 1H), 5.79 (dd, J=17.5, 10.9 Hz, 1H), 5.09 (dd, J=17.5, 1.8 Hz, 1H), 4.96 (dd, J=11.0, 1.8 Hz, 1H), 3.75 (s, 2H), 3.12 (d, J=6.2 Hz, 2H), 1.78-1.59 (m, 8H).

51F. 1-(4-(((2-amino-7-bromoquinolin-4-yl)amino) methyl)-2-oxabicyclo[2.2.2]octan-1-yl)ethane-1,2-diol A solution of 7-bromo-N4-((1-vinyl-2-oxabicyclo[2.2.2] octan-4-yl)methyl)quinoline-2,4-diamine, TFA (350 mg, 0.697 mmol) in acetone (2903 µl)-water (581 µl) was treated with an aqueous solution of 4-methylmorpholine N-oxide (490 mg, 2.090 mmol) then 0.4 mL of a 2.5% solution of OsO4 in t-BuOH. The reaction was stirred overnight. The reaction was diluted with water (~25 mL) and extracted with 10% ethanol-chloroform and then ethyl acetate. The second extract contains as much UV activity as the first, so the aqueous phase was diluted with an equal volume of brine. It was then extracted twice with ethyl acetate. The combined organic extracts were dried and stripped to afford an oily solid. This was triturated with 1:1 ether-methylene chloride. The resulting solid was filtered, rinsed with the same, and air-dried to afford 1-(4-(((2-amino-7-bromoquinolin-4-yl) amino)methyl)-2-oxabicyclo[2.2.2]octan-1-yl)ethane-1,2-diol (195 mg, 0.462 mmol, 66.3% yield) as a grainy off-white solid. $^1$H NMR (400 MHz, DMSO-$d_6$) δ 8.18 (d, J=8.9 Hz, 1H), 7.65 (d, J=2.0 Hz, 1H), 7.60-7.47 (m, 1H), 7.45 (br d, J=8.7 Hz, 1H), 7.35-6.93 (m, 2H), 5.91 (s, 1H), 4.49 (d, J=4.4 Hz, 1H), 4.36 (t, J=5.1 Hz, 1H), 4.25 (br d, J=5.4 Hz, 1H), 3.67 (s, 2H), 3.04 (br d, J=6.1 Hz, 2H), 1.70-1.49 (m, 8H).

51G. 4-(((2-amino-7-bromoquinolin-4-yl)amino) methyl)-2-oxabicyclo[2.2.2]octane-1-carbaldehyde A solution of 1-(4-(((2-amino-7-bromoquinolin-4-yl) amino)methyl)-2-oxabicyclo[2.2.2]octan-1-yl)ethane-1,2-diol (145 mg, 0.343 mmol) in THF (2 mL) was treated with a solution of sodium periodate (147 mg, 0.687 mmol) in water (1.0 mL). The resulting mixture was sonicated briefly then stirred at RT for 2 hours. The reaction was then diluted with water (~20 mL) to precipitate product. The product was filtered, rinsed with water, and air-dried to afford 4-(((2-amino-7-bromoquinolin-4-yl)amino)methyl)-2-oxabicyclo [2.2.2]octane-1-carbaldehyde (66 mg, 0.169 mmol, 49.3% yield) as an off-white solid.

51H. (4-(((2-amino-7-bromoquinolin-4-yl)amino) methyl)-2-oxabicyclo[2.2.2]octan-1-yl)methanol A solution of 4-(((2-amino-7-bromoquinolin-4-yl)amino) methyl)-2-oxabicyclo[2.2.2]octane-1-carbaldehyde (78 mg, 0.200 mmol) in THF (1332 µl)-water (666 µl) was treated with sodium borohydride (15.12 mg, 0.400 mmol) and stirred 20 minutes at RT. The reaction was diluted with water, and most of the THF was removed under a stream of nitrogen. Excess sodium borohydride was quenched by the addition of a few drops of acetic acid. The reaction was stirred briefly and then made basic with aqueous sodium carbonate. The resulting mixture was extracted twice with chloroform, and the combined organic extracts dried and stripped to afford (4-(((2-amino-7-bromoquinolin-4-yl) amino)methyl)-2-oxabicyclo[2.2.2]octan-1-yl)methanol (50 mg, 0.127 mmol, 63.8% yield) as a glass. $^1$H NMR (400 MHz, DMSO-$d_6$) δ 7.95 (d, J=8.9 Hz, 1H), 7.43 (d, J=2.0 Hz, 1H), 7.15 (dd, J=8.8, 2.0 Hz, 1H), 6.47 (br t, J=5.7 Hz, 1H), 6.05 (s, 2H), 5.79 (s, 1H), 4.48 (t, J=6.0 Hz, 1H), 3.69 (s, 2H), 3.16 (d, J=5.9 Hz, 2H), 2.97 (d, J=6.0 Hz, 2H), 1.69-1.56 (m, 8H).

Example 51

A mixture of thiophen-3-ylboronic acid (9.78 mg, 0.076 mmol), (4-(((2-amino-7-bromoquinolin-4-yl)amino) methyl)-2-oxabicyclo[2.2.2]octan-1-yl)methanol (20 mg, 0.051 mmol), PdCl$_2$(dppf)-CH$_2$Cl$_2$ adduct (4.16 mg, 5.10 µmol), and cesium carbonate (49.8 mg, 0.153 mmol) in degassed dioxane (510 µl) was placed under nitrogen and heated at 95° C. for 4 hours. The reaction was cooled, quenched with aqueous acetic acid, filtered, diluted to 2 mL with DMF. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 6% B, 6-46% B over 23 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give (4-(((2-amino-7-(thiophen-3-yl)quinolin-4-yl)amino)methyl)-2-oxabicyclo[2.2.2]octan-1-yl) methanol (12.8 mg, 64%).

Example 52. (3-(((2-amino-7-(1H-pyrazol-5-yl)quinolin-4-yl)amino)methyl)bicyclo[1.1.1]pentan-1-yl) methanol

52A. 3-(methoxycarbonyl)bicyclo[1.1.1]pentane-1-carboxylic acid

A 200 mL round-bottomed flask was charged with bicyclo [1.1.1]pentane-1,3-dicarboxylic acid (2 g, 12.81 mmol) in methanol (100 mL). Thionyl chloride (9.35 mL, 128 mmol) was added slowly. After 16 hours, the reaction was concentrated and dried under high vacuum. The material was diluted with THF (30 mL) and a solution of sodium hydroxide (12.81 mL, 12.81 mmol, 1 M) was added. After 16 hours, the pH was adjusted to pH 2 with 1N HCl. The reaction mixture was then diluted with water (50 mL). The aqueous phase was extracted with ethyl acetate (2×100 mL). The combined organic layers were dried with sodium sulfate, filtered and concentrated to give 3-(methoxycarbonyl) bicyclo[1.1.1]pentane-1-carboxylic acid (2.0 g).

52B. methyl 3-(chlorocarbonyl)bicyclo[1.1.1]pentane-1-carboxylate

A 25 mL round-bottomed flask was charged with 3-(methoxycarbonyl) bicyclo[1.1.1]pentane-1-carboxylic acid (250 mg, 1.469 mmol) in ether (10 mL). Oxalyl chloride (0.257 mL, 2.94 mmol) was added slowly. Finally, DMF (0.02 mL) was added. The completed reaction was concentrated and dried under high vacuum to give methyl 3-(chlorocarbonyl)bicyclo[1.1.1]pentane-1-carboxylate (277 mg, 100%). $^1$H NMR (400 MHz, CHLOROFORM-d) δ 3.74 (s, 3H), 2.47 (s, 6H).

52C. methyl 3-carbamoylbicyclo[1.1.1]pentane-1-carboxylate

A 50 mL round-bottomed flask was charged with methyl 3-(chlorocarbonyl) bicyclo[1.1.1]pentane-1-carboxylate (275 mg, 1.46 mmol) in methylene chloride (20 mL). Ammonia was bubbled through the solution for 30 minutes. After stirring for 2 hours the reaction was filtered and evaporated to give methyl 3-carbamoylbicyclo[1.1.1]pentane-1-carboxylate (113 mg, 46%). $^1$H NMR (400 MHz, CHLOROFORM-d) δ 5.90-5.33 (m, 2H), 3.80-3.60 (m, 3H), 2.33 (s, 5H).

52D. tert-butyl ((3-(hydroxymethyl)bicyclo[1.1.1]pentan-1-yl)methyl)carbamate A 100 mL round-bottomed flask was charged with methyl 3-carbamoylbicyclo [1.1.1]pentane-1-carboxylate (133 mg, 0.786 mmol) in THF (20 mL) and methylene chloride (20 mL). Borane-dimethyl sulfide complex (5 M in ether) (0.943 mL, 4.72 mmol) was added. After stirring for 16 hours, Boc-anhydride (0.365 mL, 1.572 mmol) and potassium carbonate (435 mg, 3.14 mmol) were added. After 70 hours, the reaction was quenched with methanol. Volatiles were removed and the residue dried under high vacuum. The crude product was dissolved in a small amount of methylene chloride and charged onto a 12 g silica gel cartridge which was then eluted with 0% to 100% ethyl acetate in hexanes. Evaporation provided tert-butyl ((3-(hydroxymethyl)bicyclo [1.1.1]pentan-1-yl)methyl)carbamate (75 mg, 42%). $^1$H NMR (400 MHz, CHLOROFORM-d) δ 4.49 (br s, 1H), 3.63 (d, J=5.9 Hz, 2H), 3.23 (br d, J=5.5 Hz, 2H), 1.64 (s, 6H), 1.47 (s, 9H), 1.19 (t, J=6.0 Hz, 1H).

52E. (3-(aminomethyl)bicyclo[1.1.1]pentan-1-yl)methanol, HCl

A 50 mL round-bottomed flask was charged with tert-butyl ((3-(hydroxymethyl) bicyclo[1.1.1]pentan-1-yl)methyl)carbamate (75 mg, 0.330 mmol) and HCl (4N dioxane) (0.412 mL, 1.650 mmol) in methylene chloride (10 mL). The reaction was stirred for 2 hours, when the volatiles were removed and the sample dried under high vacuum to give (3-(aminomethyl)bicyclo[1.1.1]pentan-1-yl)methanol, HCl (54 mg, 100%).

Example 52

A 5 mL screw top vial was charged with 4-chloro-7-(1-(tetrahydro-2H-pyran-2-yl)-1H-pyrazol-5-yl)quinolin-2-amine (25 mg, 0.076 mmol), (3-(aminomethyl) bicyclo [1.1.1]pentan-1-yl)methanol, HCl (24.89 mg, 0.152 mmol), and Hunig's base (80 µl, 0.456 mmol) in NMP (1 mL). The reaction was heated to 120° C. for 16 hours. The cooled reaction was concentrated and dried under high vacuum. TFA (500 µl, 6.49 mmol) was added and stirring continued for an hour. The reaction was then concentrated and dried under high vacuum. The reaction mixture was diluted with DMF:acetic acid 1:1 (1 mL). The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation. The material was further purified via preparative LC/MS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-minute hold at 0% B, 0-30% B over 25 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give (3-(((2-amino-7-(1H-pyrazol-5-yl)quinolin-4-yl)amino)methyl)bicyclo[1.1.1]pentan-1-yl)methanol (3.8 mg, 14%).

Biological data of compounds that were assayed using one or more of the above procedures. Unless otherwise indicated, the TLR7 agonist $EC_{50}$ and TLR8 agonist $EC_{50}$ of the below compounds were measured at values>100 µM.

| Ex No. | Structure | LC/MS [M + H]⁺/ RT (LC condition)/ NLRP3 hIL1B $EC_{50}$ | $^1$H NMR (500 MHz, DMSO-d$_6$, unless otherwise indicated) |
|---|---|---|---|
| 1 | 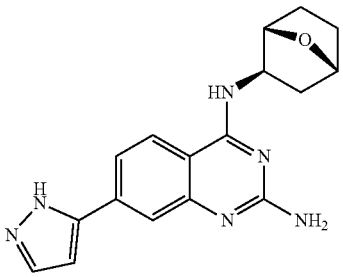 (rac) | 323.3/ 0.98 min (C)/ 0.12 µM | $^1$H-NMR (400 MHz, DMSO) δ 9.00 (br d, J = 5.7 Hz, 1H), 8.48 (br d, J = 8.5 Hz, 1H), 8.38-7.96 (m, 2H), 7.88 (br s, 2H), 7.85 (br d, J = 7.8 Hz, 1H), 6.90 (d, J = 2.0 Hz, 1H), 4.68 (br t, J = 4.6 Hz, 1H), 4.54 (d, J = 5.1 Hz, 1H), 4.36-4.25 (m, 1H), 2.07-1.98 (m, 1H), 1.98-1.89 (m, 1H), 1.71-1.53 (m, 3H), 1.52-1.45 (m, 1H) location of an exchangeable proton is not evident. |

| Ex No. | Structure | LC/MS [M + H]⁺/ RT (LC condition)/ NLRP3 hIL1B EC$_{50}$ | ¹H NMR (500 MHz, DMSO-d$_6$, unless otherwise indicated) |
|---|---|---|---|
| 2 | 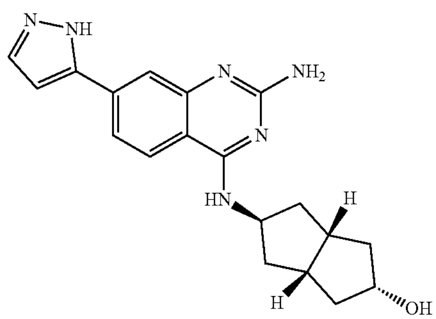 [SMILES: Nc1nc(N[C@@H]2C[C@H]3C[C@@H](O)C[C@H]3C2)c2ccc(-c3ccn[nH]3)cc2n1] | 351.3/ 1.14 min (C)/ 0.60 μM | δ 9.00 (br d, J = 5.7 Hz, 1H), 8.48 (br d, J = 8.5 Hz, 1H), 8.38-7.96 (m, 2H), 7.88 (br s, 2H), 7.85 (br d, J = 7.8 Hz, 1H), 6.90 (d, J = 2.0 Hz, 1H), 4.68 (br t, J = 4.6 Hz, 1H), 4.54 (d, J = 5.1 Hz, 1H), 4.36-4.25 (m, 1H), 2.07-1.98 (m, 1H), 1.98-1.89 (m, 1H), 1.71-1.53 (m, 3H), 1.52-1.45 (m, 1H) all exchangeable protons are not observed. |
| 3 | 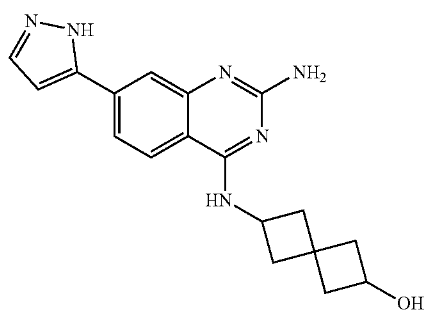 [SMILES: Nc1nc(NC2CC3(CC(O)C3)C2)c2ccc(-c3ccn[nH]3)cc2n1] | 337.0/ 0.79 min (C)/ 1.0 μM | δ 8.16-8.03 (m, 2H), 7.79-7.67 (m, 1H), 7.63 (br s, 1H), 7.54 (br d, J = 6.7 Hz, 1H), 7.25-7.14 (m, 1H), 6.80 (s, 1H), 6.42 (br d, J = 2.1 Hz, 1H), 4.67-4.52 (m, 1H), 4.06-3.93 (m, 1H), 2.42-2.34 (m, 2H), 2.33-2.24 (m, 1H), 2.23-2.17 (m, 1H), 2.16-2.07 (m, 2H), 1.89-1.79 (m, 2H) |
| 4 | 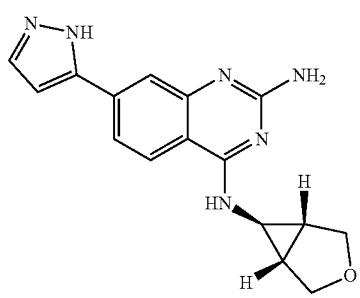 [SMILES: Nc1nc(N[C@H]2[C@@H]3COC[C@@H]32)c2ccc(-c3ccn[nH]3)cc2n1] | 309.3/ 1.04 min (C)/ 0.31 μM | δ 9.24 (br d, J = 3.4 Hz, 1H), 8.23 (br d, J = 8.2 Hz, 1H), 7.91-7.80 (m, 3H), 6.88 (s, 1H), 3.96 (d, J = 8.3 Hz, 2H), 3.69 (br d, J = 8.2 Hz, 2H), 2.09 (br s, 2H). Two protons from sidechain are not visible, likely to due overlap with suppressed water peak. |
| 5 | 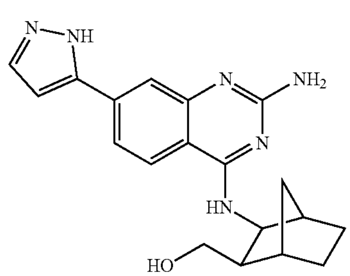 [SMILES: Nc1nc(NC2C3CCC(C3)C2CO)c2ccc(-c3ccn[nH]3)cc2n1] | 351.0/ 1.21 min (C)/ 0.81 μM | δ 8.60 (br d, J = 7.0 Hz, 1H), 8.33 (br d, J = 8.4 Hz, 1H), 7.93-7.78 (m, 3H), 6.88 (d, J = 1.9 Hz, 1H), 4.39 (br t, J = 7.8 Hz, 1H), 3.51-3.42 (m, 1H), 3.34-3.25 (m, 1H), 2.31 (br d, J = 11.5 Hz, 2H), 2.02-1.88 (m, 2H), 1.66-1.51 (m, 2H), 1.29-1.09 (m, 3H) |

| Ex No. | Structure | LC/MS [M + H]⁺/ RT (LC condition)/ NLRP3 hIL1B EC$_{50}$ | ¹H NMR (500 MHz, DMSO-d$_6$, unless otherwise indicated) |
|---|---|---|---|
| 6 | (pyrazole-quinazoline-2-amine with HN-linked bicyclic oxa-cyclopentane, •TFA) | 309.3/ 1.01 min (C)/ 0.31 μM | δ 8.76 (br s, 1H), 8.24 (br d, J = 8.5 Hz, 1H), 7.90-7.79 (m, 3H), 6.88 (s, 1H), 3.94 (br d, J = 8.9 Hz, 2H), 3.83 (br d, J = 8.2 Hz, 2H), 3.13-3.05 (m, 1H), 2.14 (br d, J = 6.7 Hz, 2H) |
| 7 | (pyrazole-quinazoline-2-amine with HN-bicyclopentane-CH$_2$OH) | 323.2/ 0.77 min (C)/ 0.20 μM) | δ 8.25 (s, 1H), 7.99 (br d, J = 8.5 Hz, 1H), 7.77-7.69 (m, 1H), 7.59 (s, 1H), 7.47 (br d, J = 8.2 Hz, 1H), 6.78 (d, J = 1.5 Hz, 1H), 6.02 (br s, 2H), 3.44 (bs, 2H), 2.06 (s, 6H). Product contains ca. 0.4 equivalents of acetic acid. |
| 8 | (pyrazole-quinazoline-2-amine with HN-linked hydroxymethyl-oxabicycle) (rac) | 353.1/ 0.75 min (C)/ 3.7 μm) | δ 8.16 (d, J = 8.5 Hz, 1H), 7.77 (br s, 1H), 7.65 (s, 1H), 7.54 (br d, J = 7.6 Hz, 1H), 6.81 (d, J = 2.1 Hz, 1H), 6.55-6.26 (m, 2H), 4.59-4.45 (m, 3H), 3.23-3.17 (m, 1H), 2.23-2.11 (m, 1H), 1.66 (br d, J = 4.6 Hz, 2H), 1.59-1.45 (m, 2H). Some protons are not visible, likely to due overlap with suppressed water peak. |
| 9 | (pyrazole-quinazoline-2-amine with N-linked oxa-azabicyclic) (rac) | 309.3/ 0.96 min (C)/ 0.68 μM | δ 8.14 (d, J = 8.9 Hz, 1H), 7.87 (br s, 2H), 7.79 (br d, J = 7.3 Hz, 1H), 6.88 (d, J = 2.1 Hz, 1H), 5.46 (s, 1H), 4.80 (s, 1H), 4.22 (br dd, J = 11.6, 4.0 Hz, 1H), 4.02-3.80 (m, 2H), 2.09-2.01 (m, 1H), 2.00-1.94 (m, 1H). Two protons are not visible, likely to due overlap with suppressed water peak. |

-continued

| Ex No. | Structure | LC/MS [M + H]+/ RT (LC condition)/ NLRP3 hIL1B EC50 | 1H NMR (500 MHz, DMSO-d6, unless otherwise indicated) |
|---|---|---|---|
| 10 | (first eluting enantiomer) | 309.2/ 0.97 min (C)/ 1.6 μM | δ 7.91 (d, J = 8.7 Hz, 1H), 7.76 (br s, 1H), 7.66 (d, J = 1.7 Hz, 1H), 7.49 (br d, J = 8.6 Hz, 1H), 6.81 (d, J = 2.2 Hz, 1H), 6.20 (br s, 2H), 5.20 (s, 1H), 4.70 (s, 1H), 4.11 (br d, J = 9.8 Hz, 1H), 3.97-3.89 (m, 1H), 3.87-3.79 (m, 1H), 3.68 (br d, J = 9.7 Hz, 1H), 2.02-1.93 (m, 1H), 1.90-1.84 (m, 1H) |
| 11 | 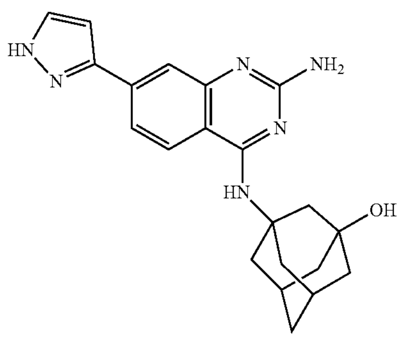 [SMILES: Nc1nc(NC23CC4CC(CC(O)(C4)C2)C3)c2ccc(-c3cc[nH]n3)cc2n1] | 377/ 1.0 min (C)/ 2.11 μM | δ 8.11 (d, J = 8.5 Hz, 1H), 7.73 (br s, 1H), 7.59 (d, J = 1.5 Hz, 1H), 7.50 (br d, J = 7.9 Hz, 1H), 6.94 (s, 1H), 6.79 (d, J = 2.1 Hz, 1H), 6.31 (br s, 2H), 3.61 (br s, 1H), 2.22-2.15 (m, 4H), 2.13-2.06 (m, 4H), 1.69-1.63 (m, 2H), 1.62-1.53 (m, 3H), 1.48-1.42 (m, 1H). Integration of OH proton appears to be reduced due to suppression of water peak. |
| 12 | 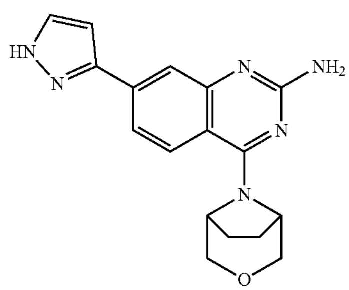 [SMILES: Nc1nc(N2C3CCC2COC3)c2ccc(-c3cc[nH]n3)cc2n1] | 323.0/ 1.07 min (C)/ 0.64 μM | δ 7.96-7.76 (m, 2H), 7.70 (s, 1H), 7.66-7.46 (m, 1H), 7.37 (s, 1H), 6.82 (d, J = 1.8 Hz, 1H), 6.36 (br s, 2H), 4.59 (br s, 2H), 3.88 (br d, J = 10.8 Hz, 2H), 3.68 (br d, J = 10.7 Hz, 1H), 3.58-3.47 (m, 1H), 2.02-1.77 (m, 4H) |
| 13 | 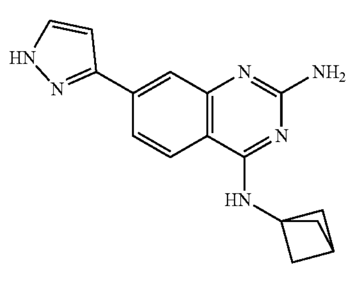 [SMILES: Nc1nc(NC23CC(C2)C3)c2ccc(-c3cc[nH]n3)cc2n1] | 293.2/ 1.16 min (C)/ 0.20 μM | δ 8.01 (d, J = 8.5 Hz, 1H), 7.75 (br s, 1H), 7.63 (d, J = 1.2 Hz, 1H), 7.52 (br d, J = 8.2 Hz, 1H), 6.81 (d, J = 2.1 Hz, 1H), 6.28 (br s, 2H), 2.55 (s, 6H), 2.22 (s, 6H). Product contains small amount of acetic acid. One proton not visible, presumably obscured by solvent. |

| Ex No. | Structure | LC/MS [M + H]+/ RT (LC condition)/ NLRP3 hIL1B EC50 | 1H NMR (500 MHz, DMSO-d6, unless otherwise indicated) |
|---|---|---|---|
| 14 | (pyrazole-quinolin-2-amine with bicyclic aminocyclopentane-OH substituent) | 350.3/ 1.21 min (C)/ 0.64 μM | δ 8.24 (br d, J = 8.3 Hz, 1H), 7.90-7.84 (m, 1H), 7.83-7.77 (m, 1H), 7.76-7.68 (m, 1H), 6.82 (d, J = 1.9 Hz, 1H), 5.89 (s, 1H), 4.12-4.00 (m, 1H), 3.92 (br t, J = 9.5 Hz, 1H), 2.10-2.00 (m, 2H), 1.95-1.85 (m, 2H), 1.82-1.71 (m, 2H), 1.30-1.15 (m, 2H). Two protons from sidechain are not visible, likely due to overlap with DMSO peak. |
| 15 | (pyrazole-quinolin-2-amine with epoxy-cyclohexylamine substituent, rac) | 322.3/ 1.01 min (C)/ 0.25 μM | δ 8.14 (d, J = 8.5 Hz, 1H), 7.78 (s, 1H), 7.74 (br s, 1H), 7.56 (br d, J = 7.6 Hz, 1H), 6.79 (d, J = 2.1 Hz, 1H), 6.70-6.53 (m, 2H), 5.68 (s, 1H), 4.63 (t, J = 4.6 Hz, 1H), 4.51 (d, J = 4.9 Hz, 1H), 3.64-3.52 (m, 1H), 2.03 (dd, J = 12.5, 7.6 Hz, 1H), 1.86 (m, 1H), 1.69-1.53 (m, 3H), 1.53-1.40 (m, 1H) |
| 16 | (pyrazole-quinolin-2-amine with bicyclopentyl-CH2OH substituent) | 322.2/ 0.83 min (C)/ 0.13 μM/ TLR7 EC50 <50 μM | δ 8.06 (br d, J = 8.9 Hz, 1H), 7.89-7.81 (m, 1H), 7.79 (br s, 1H), 7.76-7.71 (m, 1H), 7.68-7.60 (m, 1H), 6.81 (s, 1H), 6.12 (s, 1H), 3.54 (s, 2H), 2.05 (s, 6H) |
| 17 | (pyrazole-quinolin-2-amine with norbornyl-CH2OH substituent, rac, TFA) | 350.0/ 1.31 min (C)/ 1.67 μM | δ 8.15-8.07 (m, 1H), 7.98-7.91 (m, 1H), 7.89-7.85 (m, 1H), 7.85-7.80 (m, 1H), 7.77 (br d, J = 6.7 Hz, 1H), 7.71-7.58 (m, 2H), 6.84 (d, J = 1.8 Hz, 1H), 5.88 (s, 1H), 3.58 (br t, J = 7.3 Hz, 1H), 3.51-3.42 (m, 1H), 2.40-2.28 (m, 2H), 2.03-1.94 (m, 1H), 1.89 (br d, J = 10.1 Hz, 1H), 1.65-1.50 (m, 2H), 1.36-1.17 (m, 2H), 1.14 (s, 1H). One proton is not visible, likely due to overlap with suppressed water peak. |

-continued

| Ex No. | Structure | LC/MS [M + H]+/ RT (LC condition)/ NLRP3 hIL1B EC$_{50}$ | $^1$H NMR (500 MHz, DMSO-d$_6$, unless otherwise indicated) |
|---|---|---|---|
| 18 | (first eluting enantiomer) | 350.3/ 1.13 min (C)/ 3.0 μM | δ 7.82 (d, J = 8.6 Hz, 1H), 7.73 (br s, 1H), 7.55-7.47 (m, 1H), 6.75 (d, J = 1.9 Hz, 1H), 6.69-6.61 (m, 1H), 6.26-6.15 (m, 1H), 5.76 (s, 1H), 3.53-3.47 (m, 1H), 2.33-2.24 (m, 2H), 1.96-1.90 (m, 1H), 1.88-1.81 (m, 1H), 1.59-1.51 (m, 2H), 1.33-1.17 (m, 2H), 1.09 (br d, J = 9.9 Hz, 1H). Two protons are not visible, likely due to overlap with suppressed water peak. |
| 18B | (second eluting enantiomer) | 350.3/ 1.13 min (C)/ 0.98 μM | δ 7.81 (d, J = 8.6 Hz, 1H), 7.72 (br s, 1H), 7.53-7.44 (m, 1H), 6.75 (d, J = 1.9 Hz, 1H), 6.60 (br s, 1H), 6.21-6.07 (m, 1H), 5.76 (s, 1H), 3.57-3.46 (m, 1H), 2.29 (br d, J = 16.0 Hz, 2H), 1.98-1.91 (m, 1H), 1.88-1.82 (m, 1H), 1.61-1.51 (m, 2H), 1.33-1.16 (m, 2H), 1.09 (br d, J = 9.8 Hz, 1H). Two protons are not visible, likely due to overlap with suppressed water peak. |
| 19 | 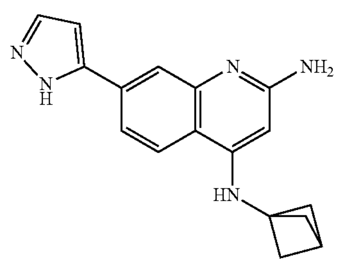 [SMILES: Nc1cc(NC23CC(C2)C3)c2ccc(-c3ccn[nH]3)cc2n1] | 292.2/ 1.27 min (C)/ 0.32 μM | δ 8.01 (d, J = 8.5 Hz, 1H), 7.77 (s, 1H), 7.74 (br s, 1H), 7.55 (br d, J = 8.2 Hz, 1H), 7.46 (br d, J = 0.6 Hz, 1H), 6.78 (d, J = 1.8 Hz, 1H), 6.71-6.49 (m, 1H), 6.14 (s, 1H), 2.57 (s, 1H), 2.21 (s, 6H) |
| 20 | 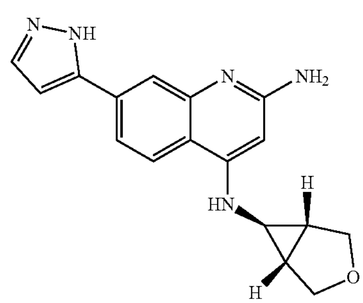 [SMILES: Nc1cc(N[C@H]2[C@@H]3COC[C@@H]32)c2ccc(-c3ccn[nH]3)cc2n1] | 308.3/ 1.11 min (C)/ 0.11 μM | δ 8.00-7.91 (m, 1H), 7.79 (s, 1H), 7.73 (br s, 1H), 7.58 (br d, J = 8.3 Hz, 1H), 7.42 (br d, J = 1.4 Hz, 1H), 6.80 (d, J = 1.9 Hz, 1H), 5.98 (s, 1H), 4.00 (d, J = 8.4 Hz, 2H), 3.74-3.66 (m, 2H), 2.23 (br s, 1H), 1.94 (s, 2H) |
| 21 | 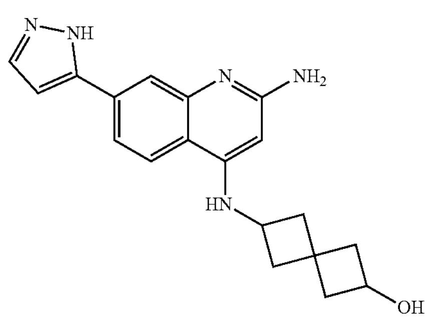 [SMILES: Nc1cc(NC2CC3(CC(O)C3)C2)c2ccc(-c3ccn[nH]3)cc2n1] | 335.9/ 1.1 min (C)/ 0.88 μM | δ 8.08 (d, J = 8.5 Hz, 1H), 7.80 (s, 1H), 7.75 (br s, 1H), 7.61 (br d, J = 8.9 Hz, 1H), 7.20 (br s, 1H), 7.07-6.89 (m, 1H), 5.61 (s, 1H), 4.02 (quin, J = 7.2 Hz, 1H), 3.91-3.78 (m, 1H), 2.50-2.46 (m, 1H), 2.46-2.37 (m, 2H), 2.22 (dt, J = 11.4, 5.9 Hz, 1H), 2.15-2.05 (m, 2H), 1.93-1.83 (m, 2H) |

| Ex No. | Structure | LC/MS [M + H]+/ RT (LC condition)/ NLRP3 hIL1B EC$_{50}$ | $^1$H NMR (500 MHz, DMSO-d$_6$, unless otherwise indicated) |
|---|---|---|---|
| 22 | 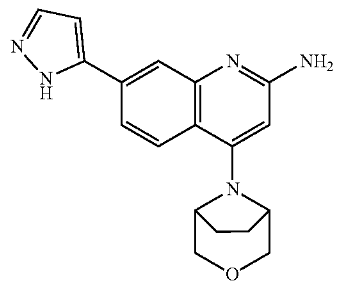 [SMILES: Nc1cc(N2C3CCC2COC3)c2ccc(-c3ccn[nH]3)cc2n1] | 322.3/ 1.16 min (C)/ 2.0 μM | δ 7.84 (d, J = 8.5 Hz, 1H), 7.78 (d, J = 1.8 Hz, 1H), 7.71 (s, 1H), 7.58-7.54 (m, 1H), 6.75 (d, J = 2.1 Hz, 1H), 6.25-6.14 (m, 3H), 3.96-3.85 (m, 5H), 3.66 (br d, J = 9.5 Hz, 1H), 1.92-1.89 (m, 4H). Four protons appear to be obscured by residual acetic acid. |
| 23 | 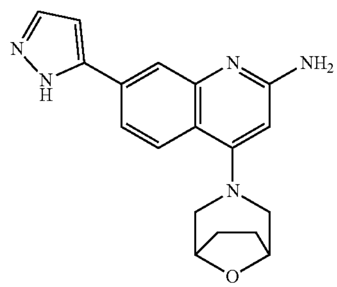 [SMILES: Nc1cc(N2CC3CCC(C2)O3)c2ccc(-c3ccn[nH]3)cc2n1] | 322.3/ 1.16 min (C)/ 0.74 μM | δ 7.81 (d, J = 1.8 Hz, 1H), 7.80-7.76 (m, 1H), 7.71 (br s, 1H), 7.59 (d, J = 8.9 Hz, 1H), 6.75 (d, J = 2.1 Hz, 1H), 6.30-6.21 (m, 3H), 4.44-4.40 (m, 2H), 3.19 (br d, J = 11.6 Hz, 2H), 2.91 (br d, J = 10.4 Hz, 2H), 2.20-2.15 (m, 2H), 1.96-1.92 (m, 2H) |
| 24 | 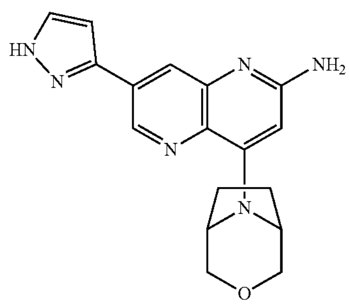 [SMILES: Nc1cc(N2C3CCC2COC3)c2ncc(-c3cc[nH]n3)cc2n1] | 323.0/ 1.01 min (C)/ 0.89 μM | δ 9.04 (s, 1H), 8.25 (br s, 1H), 7.87 (br s, 1H), 7.74 (br s, 1H), 6.94 (d, J = 2.4 Hz, 1H), 6.13 (s, 1H), 3.62 (br d, J = 11.0 Hz, 1H), 2.46 (br d, J = 3.1 Hz, 4H), 2.08-1.95 (m, 5H) |
| 25 | 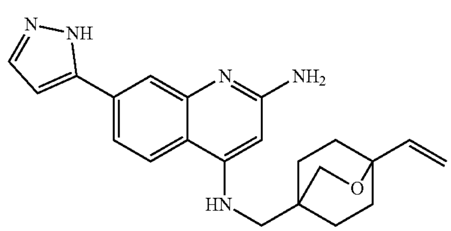 [SMILES: C=CC12CCC(CNc3cc(N)nc4cc(-c5ccn[nH]5)ccc34)(CC1)CO2] | 376/ 0.68 min (D)/ 2.0 μM/ TLR7 EC$_{50}$ <50 μM | $^1$H NMR (400 MHz, DMSO) δ 12.26 (br. s, 1H), 8.31 (d, J = 8.7 Hz, 1H), 7.83-7.98 (m, 6H), 7.50 (br. s, 2H), 6.87 (d, J = 2.2 Hz, 1H), 5.91 (s, 1H), 5.80 (dd, J = 17.6, 10.9 Hz, 1H), 5.10 (dd, J = 17.5, 1.9 Hz, 1H), 4.96 (dd, J = 10.9, 1.9 Hz, 1H), 3.77 (s, 2H), 3.14 (d, J = 6.1 Hz, 2H), 1.62-1.79 (m, 8H). |
| 26A | (First eluting enantiomer) | 336.0/ 1.02 min (C)/ 0.03 μM | δ 8.01 (d, J = 8.5 Hz, 1H), 7.76-7.68 (m, 2H), 7.51 (br d, J = 8.5 Hz, 1H), 6.90-6.82 (m, 1H), 6.75 (d, J = 2.1 Hz, 1H), 5.60 (s, 1H), 4.06-3.97 (m, 1H), 3.86-3.77 (m, 1H), 2.49-2.44 (m, 1H), 2.44-2.36 (m, 2H), 2.25-2.17 (m, 1H), 2.12-2.03 (m, 2H), 1.92-1.80 (m, 2H) |

-continued

| Ex No. | Structure | LC/MS [M + H]+/ RT (LC condition)/ NLRP3 hIL1B EC50 | 1H NMR (500 MHz, DMSO-d6, unless otherwise indicated) |
|---|---|---|---|
| 26B | 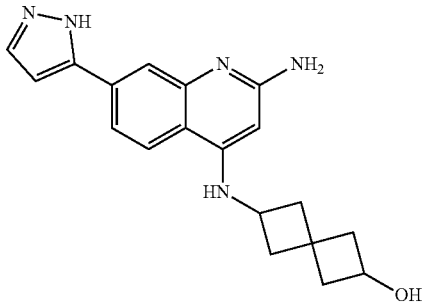<br>(Second eluting enantiomer) | 336.2/ 1.02 min (C)/ 0.25 μM | δ 7.99 (d, J = 8.5 Hz, 1H), 7.75-7.66 (m, 2H), 7.55-7.46 (m, 1H), 6.85-6.78 (m, 1H), 6.75 (d, J = 2.1 Hz, 1H), 6.29-6.16 (m, 1H), 5.59 (s, 1H), 4.06-3.95 (m, 1H), 3.86-3.76 (m, 1H), 2.49-2.44 (m, 1H), 2.43-2.35 (m, 2H), 2.26-2.16 (m, 1H), 2.12-2.02 (m, 2H), 1.93-1.83 (m, 2H) |
| 27 | 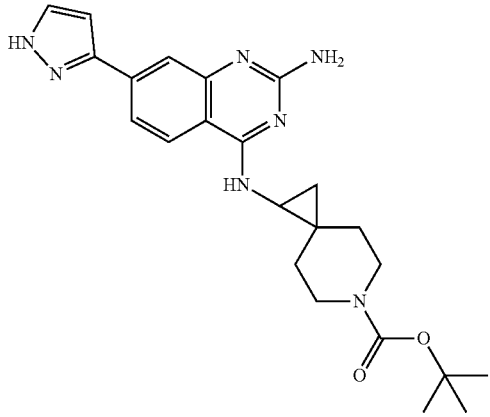 [SMILES: CC(C)(C)OC(=O)N1CCC2(CC1)CC2Nc1nc(N)nc2cc(-c3cc[nH]n3)ccc12] | 436.1/ 1.43 min (C)/ 0.39 μM | δ 8.06 (d, J = 8.5 Hz, 1H), 7.88 (br s, 1H), 7.76 (br d, J = 2.1 Hz, 1H), 7.65 (s, 1H), 7.52 (br d, J = 7.9 Hz, 1H), 6.81 (d, J = 2.1 Hz, 1H), 6.35-6.13 (m, 2H), 2.85 (dt, J = 7.3, 3.7 Hz, 1H), 1.63-1.43 (m, 2H), 1.38 (br s, 8H), 1.32-1.14 (m, 2H), 0.94-0.75 (m, 2H). Some protons are not visible, likely to due overlap with suppressed water peak. |
| 28A | 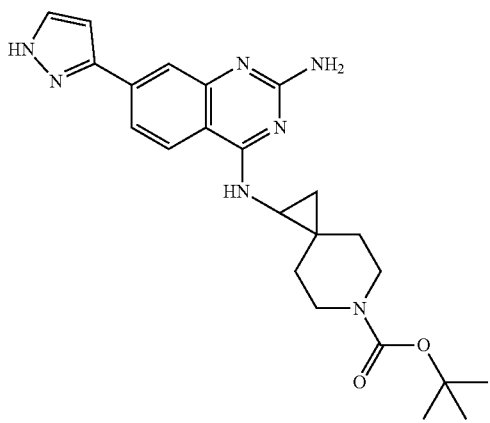<br>(First eluting enantiomer) | 436.2/ 1.38 min (C)/ 1.94 μM | δ 8.05 (d, J = 8.6 Hz, 1H), 7.82 (br s, 1H), 7.75 (br s, 1H), 7.63 (s, 1H), 7.50 (br d, J = 8.7 Hz, 1H), 6.81 (d, J = 2.0 Hz, 1H), 6.18 (br s, 2H), 2.87-2.78 (m, 1H), 1.58-1.42 (m, 2H), 1.38 (br s, 9H), 1.32-1.20 (m, 2H), 0.86-0.77 (m, 2H). Some protons are not visible, likely to due to overlap with suppressed water peak. |

| Ex No. | Structure | LC/MS [M + H]+/ RT (LC condition)/ NLRP3 hIL1B EC50 | 1H NMR (500 MHz, DMSO-d6, unless otherwise indicated) |
|---|---|---|---|
| 28B | (Second eluting enantiomer) | 436.0/ 1.38 min (C)/ 0.78 μM | δ 8.05 (d, J = 8.6 Hz, 1H), 7.84 (br s, 1H), 7.75 (br s, 1H), 7.63 (s, 1H), 7.51 (br d, J = 8.0 Hz, 1H), 6.81 (d, J = 1.9 Hz, 1H), 6.19 (br s, 2H), 2.88-2.79 (m, 1H), 1.57-1.41 (m, 2H), 1.38 (br s, 9H), 1.32-1.20 (m, 2H), 0.89-0.74 (m, 2H) Some protons are not visible, likely to due to overlap with suppressed water peak. |
| 29 | (racemic) | 323.3/ 1.13 min (C)/ 0.50 μM | δ 8.18 (d, J = 8.5 Hz, 1H), 7.82 (br d, J = 4.6 Hz, 1H), 7.76 (br s, 1H), 7.63 (s, 1H), 7.55 (br d, J = 8.5 Hz, 1H), 6.82 (d, J = 2.1 Hz, 1H), 6.32 (br s, 2H), 4.93 (t, J = 5.0 Hz, 1H), 4.53 (t, J = 5.0 Hz, 1H), 4.30-4.16 (m, 1H), 2.18-2.05 (m, 1H), 1.83-1.73 (m, 1H), 1.72-1.57 (m, 3H), 1.47-1.35 (m, 1H). One exchangeable proton not observed. |
| 30 | (racemic) | 322.3/ 1.06 min (C)/ 0.65 μM | δ 8.17 (d, J = 8.5 Hz, 1H), 7.80 (s, 1H), 7.75 (br s, 1H), 7.60 (br d, J = 8.5 Hz, 1H), 6.96 (br d, J = 3.1 Hz, 1H), 6.79 (d, J = 2.1 Hz, 1H), 6.78-6.66 (m, 1H), 5.88 (s, 1H), 4.83 (t, J = 4.7 Hz, 1H), 4.56 (t, J = 5.3 Hz, 1H), 3.82-3.72 (m, 1H), 2.25-2.13 (m, 1H), 1.88-1.80 (m, 1H), 1.75-1.66 (m, 2H), 1.65-1.55 (m, 1H), 1.46 (ddd, J = 15.9, 11.4, 4.1 Hz, 1H). Some exchangeable protons not observed. |
| 31A | (first eluting mixture) | 339.1 and 339.2/0.49 min and 0.51 min (E)/ 1.21 μM | |
| 31B | (racemic, second eluting) | 339.2/ 0.51 minn (E)/ 1.85 μM | δ 4.67 (br t, J = 4.8 Hz, 1H), 4.27 (s, 1H), 4.27-4.18 (m, 1H), 3.98 (br d, J = 3.2 Hz, 1H), 3.56 (br d, J = 3.7 Hz, 1H), 1.90 (ddd, J = 15.8, 12.6, 7.5 Hz, 2H), 1.83-1.71 (m, 1H), 1.48-1.33 (m, 1H). Some exchangeable protons not observed. |

-continued

| Ex No. | Structure | LC/MS [M + H]+/ RT (LC condition)/ NLRP3 hIL1B EC$_{50}$ | $^1$H NMR (500 MHz, DMSO-d$_6$, unless otherwise indicated) |
|---|---|---|---|
| 32A | (first eluting mixture) | 338.0/ 0.91 min (C)/ 0.38 μM | Approximate ratio is 1.5:1 syn/anti by $^1$H-NMR |
| 32B | (or enantiomer, second eluting peak) | 338.3/ 0.91 min (C)/ 0.25 μM | δ 8.13 (d, J = 8.5 Hz, 1H), 7.76 (s, 1H), 7.72 (br s, 1H), 7.55 (br d, J = 7.9 Hz, 1H), 6.77 (d, J = 1.8 Hz, 1H), 6.67 (br s, 1H), 6.51 (br s, 1H), 5.69 (s, 1H), 4.61 (br t, J = 5.3 Hz, 1H), 4.27 (s, 1H), 3.99 (br d, J = 4.9 Hz, 1H), 1.97-1.82 (m, 2H), 1.77-1.66 (m, 1H), 1.41 (m, 1H). All exchangeable protons are not observed and one proton is affected by the water suppression routine. |
| 33 | 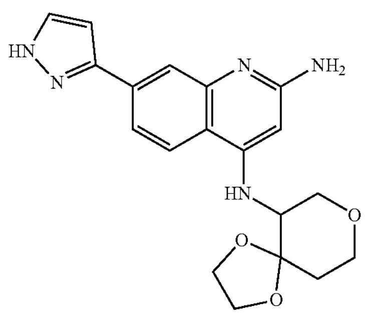 [SMILES: Nc1cc(NC2COCCC23OCCO3)c2ccc(-c3cc[nH]n3)cc2n1] | 368.1/ 1.12 min (C)/ 17.4 μM | δ 8.50-8.38 (m, 1H), 8.00-7.90 (m, 1H), 7.89-7.80 (m, 2H), 7.32-7.22 (m, 1H), 6.92-6.81 (m, 1H), 6.20-6.07 (m, 1H), 4.06-3.99 (m, 1H), 3.99-3.91 (m, 1H), 3.91-3.81 (m, 2H), 3.68-3.62 (m, 1H), 3.19-3.15 (m, 1H), 2.90-2.87 (m, 1H), 2.57-2.54 (m, 1H), 1.95-1.86 (m, 1H), 1.84-1.73 (m, 1H) |
| 34 | 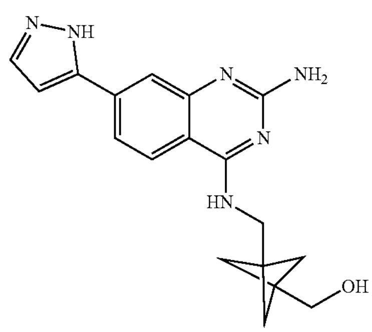 [SMILES: Nc1nc(NCC23CC(CO)(C2)C3)c2ccc(-c3ccn[nH]3)cc2n1] | 337.2/ 1.02 min (C)/ 3.96 μM | δ 8.40-8.24 (m, 1H), 8.10 (br d, J = 8.5 Hz, 1H), 7.77 (br s, 1H), 7.68 (br s, 1H), 7.61 (br d, J = 7.6 Hz, 1H), 6.83 (d, J = 1.8 Hz, 1H), 6.73-6.50 (m, 1H), 3.34 (s, 2H), 1.55 (s, 6H). One methylene likely obscured by suppressed water peak. |
| 35 | (racemate) | 293.2/ 1.21 min (C)/ 0.19 μM | δ 8.38-8.20 (m, 1H), 8.10 (d, J = 8.5 Hz, 1H), 7.86-7.73 (m, 1H), 7.68 (s, 1H), 7.58 (br d, J = 6.7 Hz, 1H), 6.83 (d, J = 2.2 Hz, 1H), 6.72-6.39 (m, 2H), 3.33-3.21 (m, 1H), 1.32 (br t, J = 5.8 Hz, 1H), 1.20 (br t, J = 4.0 Hz, 1H), 1.16-1.10 (m, 1H), 0.92-0.82 (m, 2H), 0.80-0.69 (m, 1H) |

-continued

| Ex No. | Structure | LC/MS [M + H]+/ RT (LC condition)/ NLRP3 hIL1B EC$_{50}$ | $^1$H NMR (500 MHz, DMSO-d$_6$, unless otherwise indicated) |
|---|---|---|---|
| 36A | (first eluting enantiomer) | 293.0/ 1.03 min (C)/ 0.085 μM | δ 8.04 (d, J = 8.5 Hz, 1H), 7.95 (br s, 1H), 7.84-7.69 (m, 1H), 7.62 (s, 1H), 7.50 (br d, J = 7.0 Hz, 1H), 6.81 (d, J = 2.1 Hz, 1H), 6.09 (br s, 1H), 3.29-3.20 (m, 1H), 1.30 (br t, J = 6.0 Hz, 1H), 1.16 (br t, J = 4.0 Hz, 1H), 1.15-1.08 (m, 1H), 0.93-0.80 (m, 2H), 0.74 (br d, J = 4.3 Hz, 1H) |
| 36B | (second eluting enantiomer) | 292.9/ 1.03 min (C)/ 0.13 μM | δ 8.04 (br d, J = 8.5 Hz, 1H), 7.92 (br d, J = 1.5 Hz, 1H), 7.86-7.67 (m, 1H), 7.62 (s, 1H), 7.50 (br d, J = 7.3 Hz, 1H), 6.81 (d, J = 1.8 Hz, 1H), 6.07 (br s, 2H), 3.30-3.20 (m, 1H), 1.30 (dd, J = 6.4, 5.2 Hz, 1H), 1.16 (br t, J = 4.4 Hz, 1H), 1.15-1.10 (m, 1H), 0.95-0.80 (m, 2H), 0.78-0.69 (m, 1H) |
| 37 | 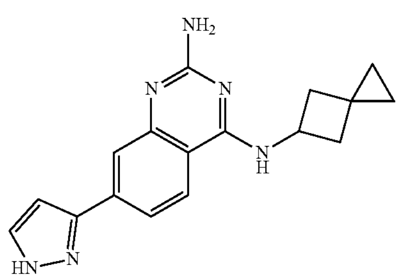 [SMILES: Nc1nc(NC2CC3(CC3)C2)c2ccc(-c3cc[nH]n3)cc2n1] | 307.2/ 1.34 min (C)/ 0.30 μM | δ 8.23-8.08 (m, 2H), 7.87-7.71 (m, 1H), 7.63 (s, 1H), 7.59-7.48 (m, 1H), 6.82 (d, J = 2.1 Hz, 1H), 6.30 (br s, 2H), 4.98-4.83 (m, 1H), 2.49-2.41 (m, 2H), 2.34-2.23 (m, 2H), 0.60-0.48 (m, 2H), 0.47-0.38 (m, 2H) |
| 38 | 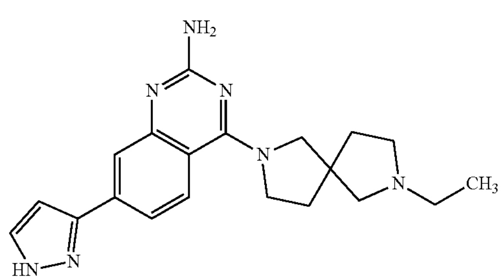 [SMILES: CCN1CCC2(CCN(c3nc(N)nc4cc(-c5cc[nH]n5)ccc34)C2)C1] | 363.9/ 0.60 min (C)/ 2.58 μM | δ 8.04 (d, J = 8.8 Hz, 1H), 7.85-7.70 (m, 1H), 7.64 (s, 1H), 7.48 (br dd, J = 3.2, 1.3 Hz, 1H), 6.80 (s, 1H), 6.02 (br s, 2H), 3.85 (br s, 1H), 3.80 (br d, J = 10.9 Hz, 1H), 3.75-3.66 (m, 1H), 2.67-2.59 (m, 1H), 2.48-2.38 (m, 3H), 2.02-1.88 (m, 2H), 1.84-1.72 (m, 2H), 1.02 (t, J = 7.0 Hz, 3H). Some protons are not visible, likely to due overlap with suppressed water peak. |
| 39 | 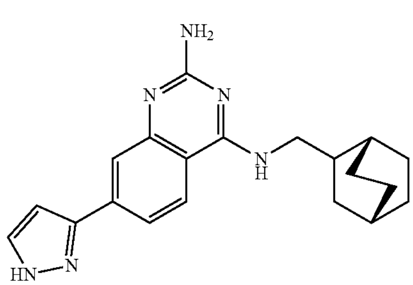 [SMILES: Nc1nc(NCC2C[C@H]3CC[C@@H]2CC3)c2ccc(-c3cc[nH]n3)cc2n1] | 349.0/ 1.61 min (C)/ 0.86 μM | δ 9.24 (br t, J = 5.2 Hz, 1H), 8.29 (br d, J = 8.5 Hz, 1H), 7.87 (br t, J = 9.9 Hz, 3H), 6.89 (d, J = 1.8 Hz, 1H), 3.64-3.50 (m, 1H, integral appears low from water suppression), 2.21-2.08 (m, 1H), 1.85-1.68 (m, 2H), 1.62-1.42 (m, 8H), 1.38 (br s, 1H), 1.10 (br dd, J = 13.1, 6.1 Hz, 1H). |

| Ex No. | Structure | LC/MS [M + H]+/ RT (LC condition)/ NLRP3 hIL1B EC$_{50}$ | $^1$H NMR (500 MHz, DMSO-d$_6$, unless otherwise indicated) |
| --- | --- | --- | --- |
| 40 | (rac) | 337.1/ 1.05 min (C)/ 0.22 μM | δ 10.05-9.95 (m, 1H), 7.87 (br s, 3H), 7.73-7.66 (m, 1H), 6.87 (br s, 1H), 4.75-4.65 (m, 1H), 4.53-4.43 (m, 1H), 2.46-2.37 (m, 1H), 2.33-2.24 (m, 1H), 2.13 (br d, J = 7.6 Hz, 1H), 1.69-1.26 (m, 4H), 1.20 (br d, J = 12.8 Hz, 1H) |
| 41A | (First eluting) | 337.0/ 1.17 min (C)/ 0.16 μM | δ 9.03 (br d, J = 1.8 Hz, 1H), 7.86-7.71 (m, 1H), 7.69-7.61 (m, 1H), 7.60-7.50 (m, 1H), 7.47 (br d, J = 8.2 Hz, 1H), 6.80 (d, J = 1.8 Hz, 1H), 6.56-6.30 (m, 2H), 4.72-4.60 (m, 1H), 4.52-4.42 (m, 1H), 4.13-3.98 (m, 1H), 2.43-2.38 (m, 1H), 2.32-2.22 (m, 2H), 2.16-2.03 (m, 1H), 1.45-1.33 (m, 2H), 1.20-1.08 (m, 2H) |
| 41B | (Second eluting) | 337.3/ 1.26 min (C)/ 0.96 μM | δ 7.83-7.74 (m, 1H), 7.72-7.67 (m, 1H), 7.64-7.56 (m, 1H), 7.54-7.45 (m, 1H), 6.87-6.79 (m, 1H), 6.76-6.58 (m, 1H), 4.71-4.62 (m, 1H), 4.54-4.42 (m, 1H), 4.13-3.98 (m, 1H), 2.44-2.38 (m, 1H), 2.33-2.22 (m, 2H), 2.17-2.02 (m, 2H), 1.43-1.33 (m, 2H), 1.21-1.11 (m, 4H) |
| 42 | (rac) | 336.8/ 1.07 min (C)/ 0.74 μM | δ 8.71 (br d, J = 6.1 Hz, 1H), 8.48 (d, J = 8.9 Hz, 1H), 8.40-8.01 (m, 2H), 7.89-7.84 (m, 2H), 6.89 (d, J = 2.2 Hz, 1H), 4.32 (br dd, J = 9.5, 4.0 Hz, 1H), 3.80 (br d, J = 6.1 Hz, 1H), 2.62 (br s, 1H), 2.09 (br d, J = 4.7 Hz, 1H), 2.02-1.88 (m, 2H), 1.70 (br d, J = 9.8 Hz, 1H), 1.36-1.20 (m, 2H), 1.13 (br d, J = 11.9 Hz, 1H) |

-continued

| Ex No. | Structure | LC/MS [M + H]+/ RT (LC condition)/ NLRP3 hIL1B EC$_{50}$ | $^1$H NMR (500 MHz, DMSO-d$_6$, unless otherwise indicated) |
|---|---|---|---|
| 43A | (first eluting) | 337.1/ 1.07 min (C)/ 1.64 μM | δ 8.22 (br d, J = 8.5 Hz, 1H), 7.78 (br s, 1H), 7.64 (s, 1H), 7.57 (br d, J = 8.5 Hz, 1H), 7.52 (br s, 1H), 6.83 (d, J = 1.8 Hz, 1H), 6.30 (br s, 1H), 4.25 (br d, J = 4.3 Hz, 1H), 3.79 (br d, J = 6.4 Hz, 1H), 2.61 (br s, 1H), 2.07 (br d, J = 4.3 Hz, 1H), 1.97 (br dd, J = 12.8, 5.2 Hz, 2H), 1.68 (br d, J = 8.9 Hz, 1H), 1.29 (br d, J = 9.5 Hz, 1H), 1.19-1.05 (m, 2H) |
| 43B | (second eluting) | 337.2/ 1.02 min (C)/ 1.11 μM | δ 8.16 (d, J = 8.7 Hz, 1H), 7.81-7.71 (m, 1H), 7.59 (s, 1H), 7.54-7.46 (m, 1H), 7.36 (br d, J = 5.5 Hz, 1H), 6.80 (d, J = 2.2 Hz, 1H), 6.02 (s, 1H), 4.30-4.16 (m, 1H), 3.77 (br d, J = 6.8 Hz, 1H), 2.58 (br s, 1H), 2.04 (br d, J = 4.5 Hz, 1H), 1.99-1.88 (m, 2H), 1.64 (br d, J = 9.4 Hz, 1H), 1.26 (br d, J = 9.4 Hz, 1H), 1.13-1.01 (m, 2H) |
| 44 | (rac) | 337.1/ 1.08 min (C)/ 2.37 μM | δ 8.23 (br d, J = 8.5 Hz, 1H), 7.88-7.72 (m, 1H), 7.66 (br s, 1H), 7.63-7.62 (m, 1H), 6.55-6.27 (m, 1H), 4.36 (br dd, J = 10.8, 4.7 Hz, 1H), 3.96 (dd, J = 3.5, 1.8 Hz, 1H), 2.59 (br d, J = 2.4 Hz, 1H), 2.23 (br s, 1H), 2.01-1.85 (m, 2H), 1.62 (br d, J = 8.9 Hz, 1H), 1.33-1.21 (m, 2H) |
| 45A | (first eluting) | 337.3/ 1.09 min (C)/ 2.12 μM | $^1$H NMR (500 MHz, DMSO-d$_6$) δ 8.19 (br d, J = 8.5 Hz, 1H), 7.86-7.73 (m, 1H), 7.62 (s, 1H), 7.57-7.46 (m, 1H), 7.37 (br d, J = 6.6 Hz, 1H), 6.81 (d, J = 1.9 Hz, 1H), 6.14 (br s, 2H), 4.43-4.30 (m, 1H), 4.03-3.93 (m, 1H), 2.59 (br d, J = 4.0 Hz, 1H), 2.22 (br s, 1H), 1.98-1.85 (m, 2H), 1.61 (br d, J = 9.1 Hz, 1H), 1.25 (br d, J = 10.2 Hz, 3H) |

| Ex No. | Structure | LC/MS [M + H]+/ RT (LC condition)/ NLRP3 hIL1B EC$_{50}$ | $^1$H NMR (500 MHz, DMSO-d$_6$, unless otherwise indicated) |
|---|---|---|---|
| 45B | 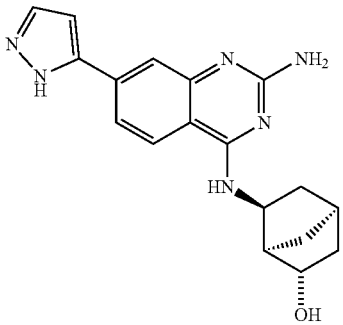 [SMILES: Nc1nc(N[C@H]2C[C@@H]3C[C@H]2[C@@H](O)C3)c2ccc(-c3ccn[nH]3)cc2n1]<br>(second eluting) | 337.0/<br>1.09 min (C)/<br>3.0 μM | δ 8.18 (br d, J = 8.8 Hz, 1H), 7.86-7.68 (m, 1H), 7.61 (s, 1H), 7.51 (dd, J = 2.9, 1.1 Hz, 1H), 7.33 (br d, J = 6.2 Hz, 1H), 6.81 (d, J = 1.9 Hz, 1H), 6.08 (br s, 2H), 4.42-4.28 (m, 1H), 4.03-3.91 (m, 1H), 2.59 (br d, J = 2.9 Hz, 1H), 2.22 (br s, 1H), 1.99-1.86 (m, 2H), 1.61 (br d, J = 9.2 Hz, 1H), 1.34-1.18 (m, 3H) |
| 46 | 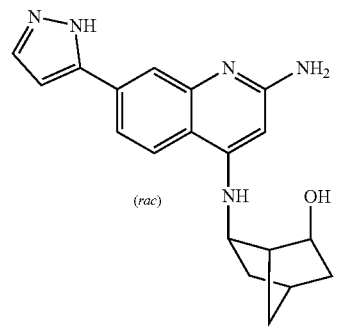 [SMILES: Nc1cc(NC2CC3CC(O)C2C3)c2ccc(-c3ccn[nH]3)cc2n1]<br>(rac) | 336.2/<br>1.23 min (C)/<br>1.33 μM | δ 8.48-8.34 (m, 1H), 7.85-7.78 (m, 1H), 7.77-7.68 (m, 1H), 7.65-7.54 (m, 1H), 7.45 (br d, J = 8.6 Hz, 1H), 6.78 (s, 1H), 5.61 (s, 1H), 4.53-4.39 (m, 1H), 4.05-3.94 (m, 1H), 2.29 (br s, 2H), 2.16-2.06 (m, 1H), 1.43-1.30 (m, 2H), 1.14-1.01 (m, 2H). One aliphatic peak is not visible, likely due to overlap with suppressed water peak or DMSO peak. |
| 47 | 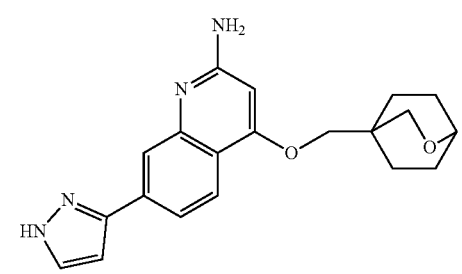 [SMILES: Nc1cc(OCC23CCC(CC2)OC3)c2ccc(-c3cc[nH]n3)cc2n1] | 351.0/<br>1.31 min (C)/<br>0.32 μM | δ 7.86 (d, J = 8.5 Hz, 1H), 7.79 (s, 1H), 7.77-7.69 (m, 1H), 7.65-7.56 (m, 1H), 6.78 (d, J = 1.9 Hz, 1H), 6.26 (br s, 1H), 6.15 (s, 1H), 3.79 (br d, J = 16.0 Hz, 4H), 2.03-1.93 (m, 2H), 1.82-1.75 (m, 2H), 1.72-1.57 (m, 4H). One methine likely obscured by suppressed water peak. |
| 48 | 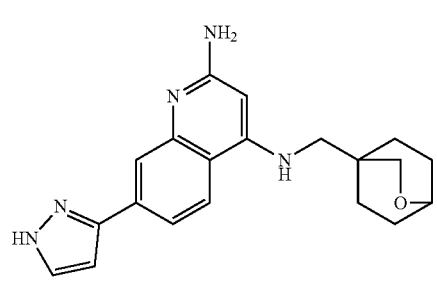 [SMILES: Nc1cc(NCC23CCC(CC2)OC3)c2ccc(-c3cc[nH]n3)cc2n1] | 350.0/<br>1.31 min (C)/<br>0.57 μM | δ 8.09 (d, J = 8.5 Hz, 1H), 7.80 (s, 1H), 7.75 (br s, 1H), 7.60 (br d, J = 8.5 Hz, 1H), 6.87 (br s, 1H), 6.80 (d, J = 1.8 Hz, 1H), 5.79 (s, 1H), 3.68 (s, 2H), 3.01 (br d, J = 6.1 Hz, 2H), 1.93-1.83 (m, obscured, ~2H), 1.67-1.57 (m, ~6H). One methine likely obscured by suppressed water peak. |
| 49 | 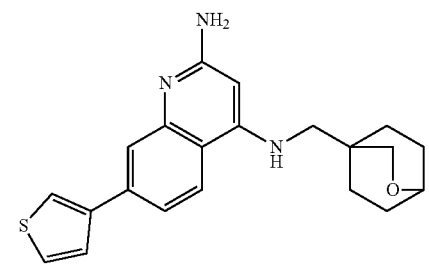 [SMILES: Nc1cc(NCC23CCC(CC2)OC3)c2ccc(-c3ccsc3)cc2n1] | 366.2/<br>1.45 min (C)/<br>0.54 μM | δ 8.09 (d, J = 8.5 Hz, 1H), 7.98 (d, J = 1.2 Hz, 1H), 7.72-7.65 (m, 2H), 7.62 (d, J = 5.2 Hz, 1H), 7.51 (br d, J = 8.2 Hz, 1H), 6.85-6.79 (m, 1H), 6.73 (br d, J = 1.8 Hz, 1H), 5.79 (s, 1H), 3.69 (s, 2H), 3.01 (br d, J = 6.1 Hz, 2H), 1.89 (m, obscured, ~2H), 1.71-1.55 (m, 6H). One methine likely obscured by suppressed water peak. |

| Ex No. | Structure | LC/MS [M + H]+/ RT (LC condition)/ NLRP3 hIL1B EC$_{50}$ | $^1$H NMR (500 MHz, DMSO-d$_6$, unless otherwise indicated) |
|---|---|---|---|
| 50 | 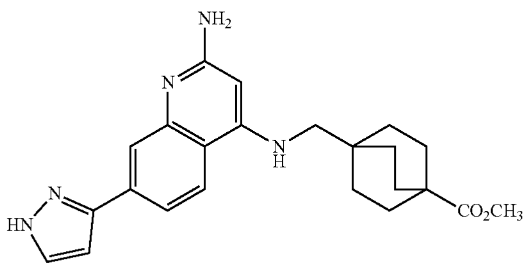 [SMILES: COC(=O)C12CCC(CNc3cc(N)nc4cc(-c5cc[nH]n5)ccc34)(CC1)CC2] | 406.1/ 1.43 min (C)/ 1.73 μM | δ 8.10 (br d, J = 8.5 Hz, 1H), 7.79 (s, 1H), 7.76 (br s, 1H), 7.58 (br d, J = 8.2 Hz, 1H), 6.80 (br d, J = 1.8 Hz, 1H), 6.72 (br d, J = 6.1 Hz, 2H), 5.82 (s, 1H), 3.59 (s, intensity diminished by water suppression), 3.06-2.95 (m, 2H), 1.79-1.66 (m, 5H), 1.59-1.48 (m, 6H) |
| 51 | 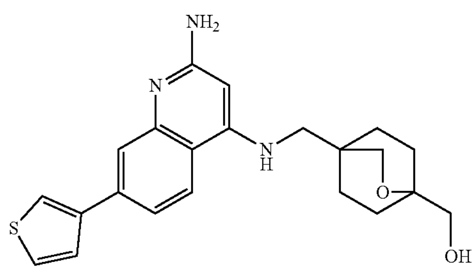 [SMILES: Nc1cc(NCC23CCC(CO)(CC2)OC3)c2ccc(-c3ccsc3)cc2n1] | 396.1/ 1.36 min (C)/ 1.86 μM | δ 8.08 (d, J = 8.5 Hz, 1H), 7.99 (br s, 1H), 7.73-7.65 (m, 2H), 7.63 (br d, J = 4.6 Hz, 1H), 7.52 (br d, J = 7.9 Hz, 1H), 6.86 (br t, J = 5.2 Hz, 1H), 6.80 (br s, 1H), 5.80 (s, 1H), 3.70 (s, 1H, integral low from solvent suppression), 3.17 (s, 2H), 3.04 (br d, J = 6.1 Hz, 2H), 1.75-1.51 (m, 8H) |
| 52 | 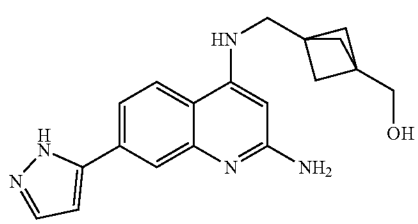 [SMILES: Nc1cc(NCC23CC(CO)(C2)C3)c2ccc(-c3ccn[nH]3)cc2n1] | 336.0/ 1.05 min (C)/ 0.98 μM | δ 8.03 (br d, J = 8.5 Hz, 1H), 7.80 (s, 1H), 7.75 (br s, 1H), 7.59 (br d, J = 7.9 Hz, 1H), 7.17 (br s, 1H), 7.10-6.92 (m, 1H), 6.80 (d, J = 1.8 Hz, 1H), 5.76 (s, 1H), 3.35 (s, 2H), 1.60 (s, 6H). One methylene likely obscured by suppressed water peak. |

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula (I):

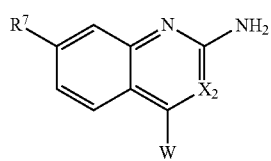

(I)

or a stereoisomer, a tautomer, or a pharmaceutically acceptable salt thereof, wherein:

W is independently selected from: —NH—R$^6$, —NH—CH$_2$—R$^6$,

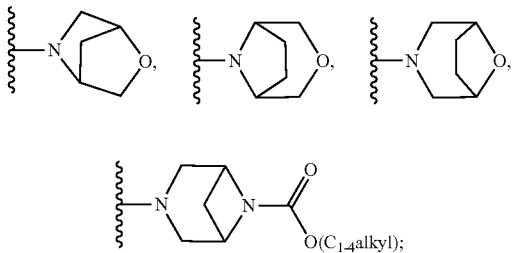

and

R⁶ is independently selected from

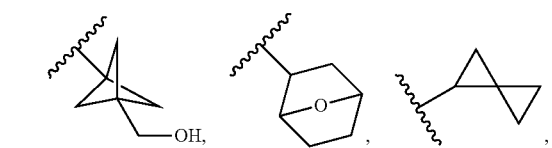

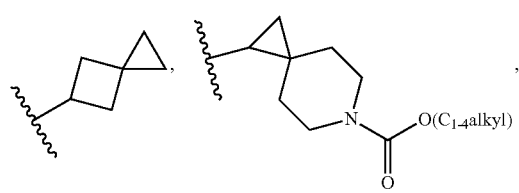

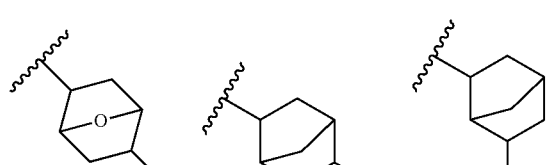

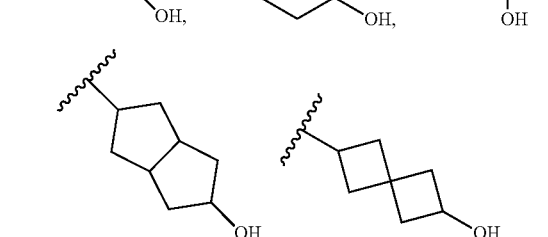

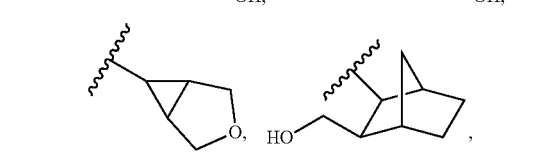

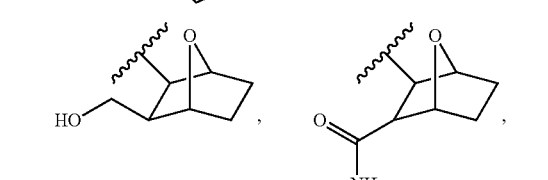

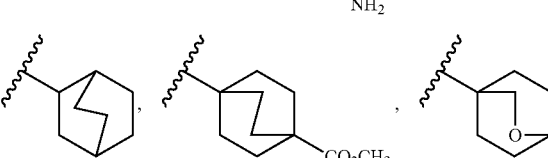

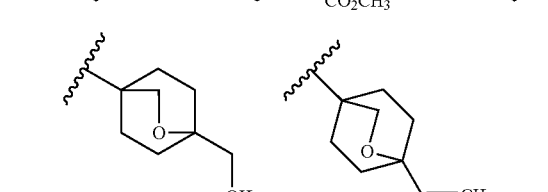

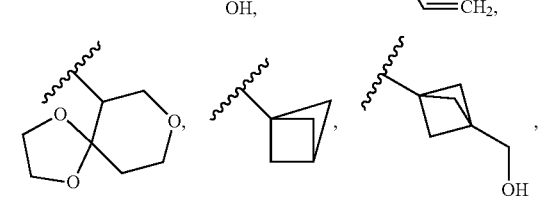

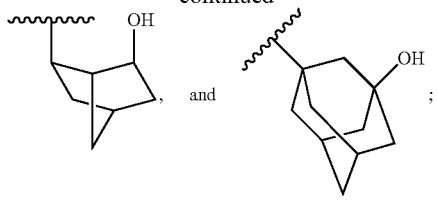

X₂ is independently N or CH; and
R⁷ is independently a heteroaryl including 5 ring atoms, wherein from 1 to 4 ring atoms are each independently selected from N, NH, N(C₁₋₄ alkyl), O, and S.

2. The compound of claim 1, wherein the compound is of Formula (II):

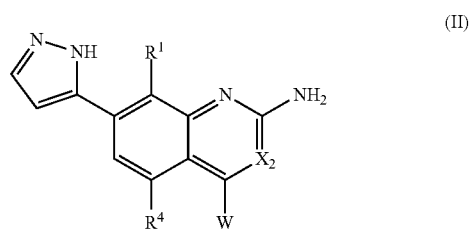

(II)

or a stereoisomer, a tautomer, or a pharmaceutically acceptable salt thereof.

3. The compound of claim 2, wherein:

W is independently selected from: —NH—R⁶,

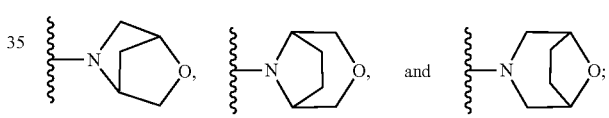

and

R⁶ is independently selected from:

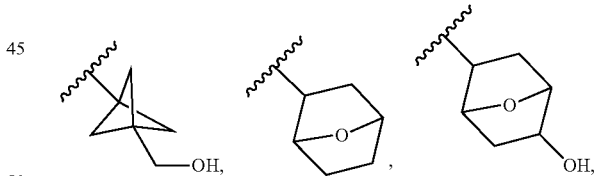

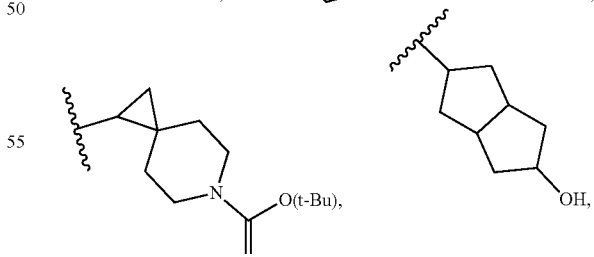

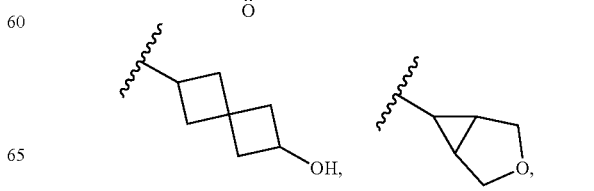

117
-continued
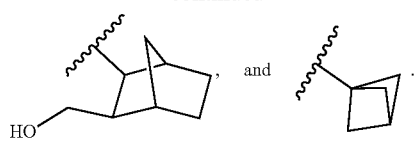
and
4. A compound selected from:
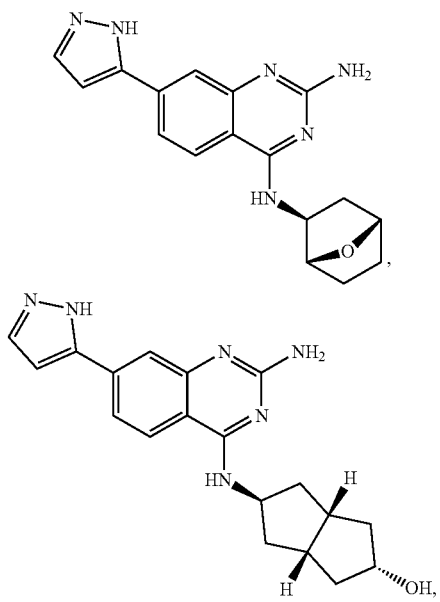
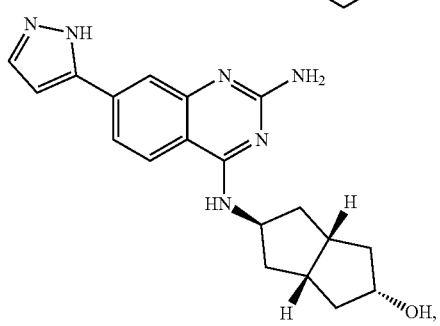
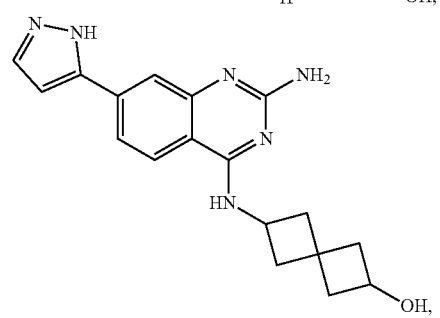
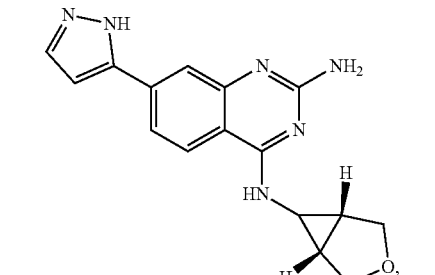
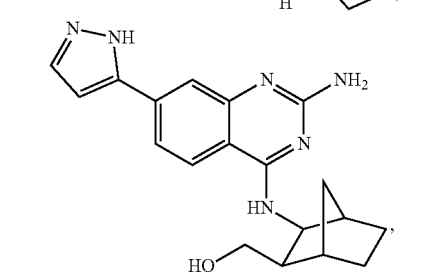
118
-continued
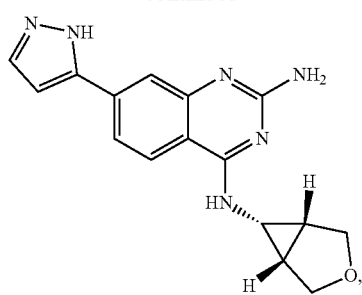
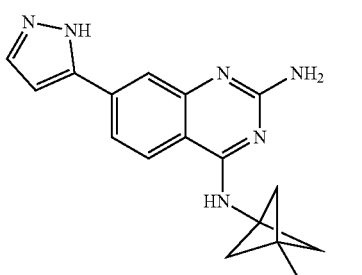
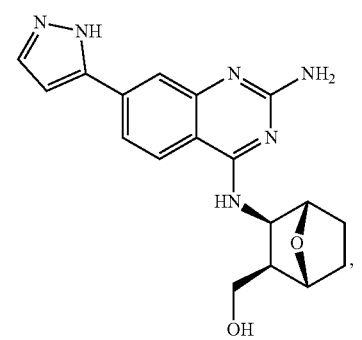
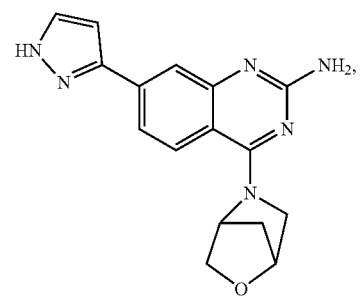
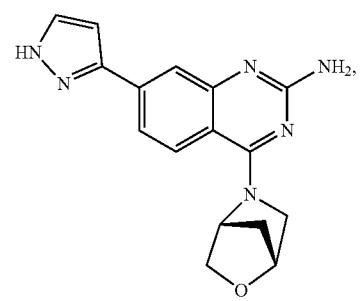

-continued
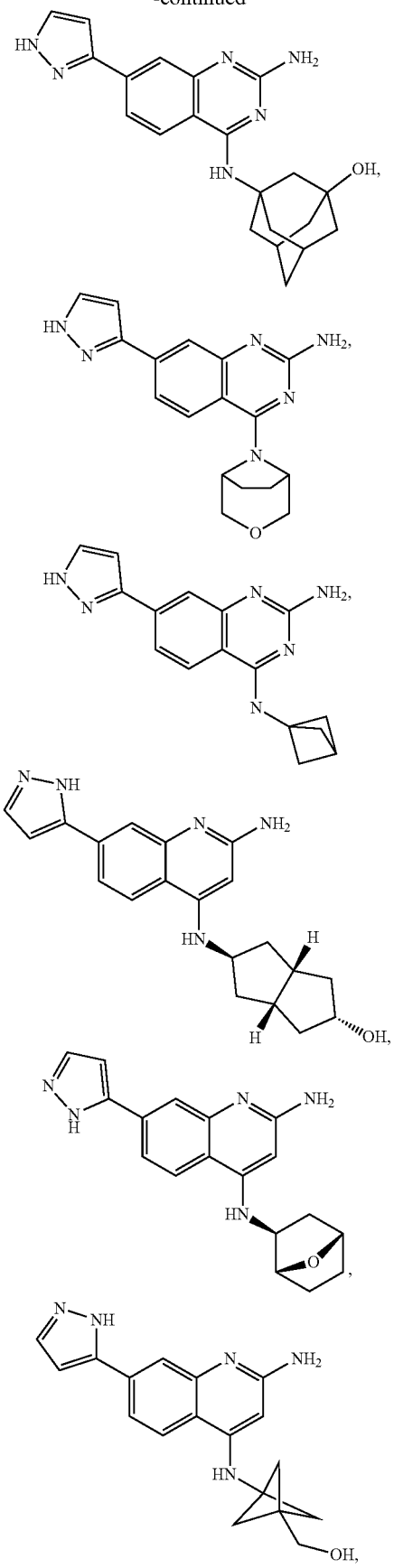
-continued
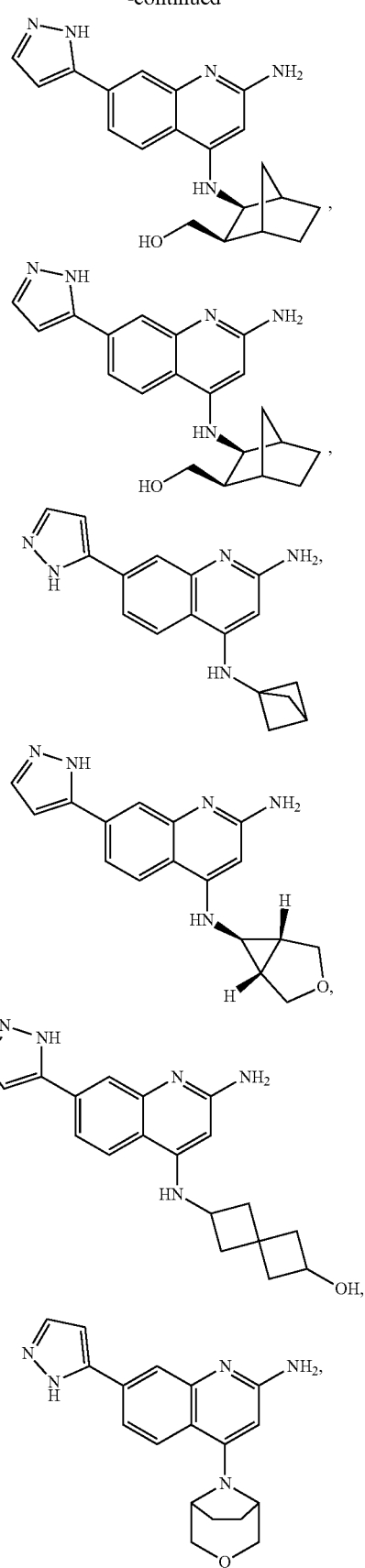

121
-continued
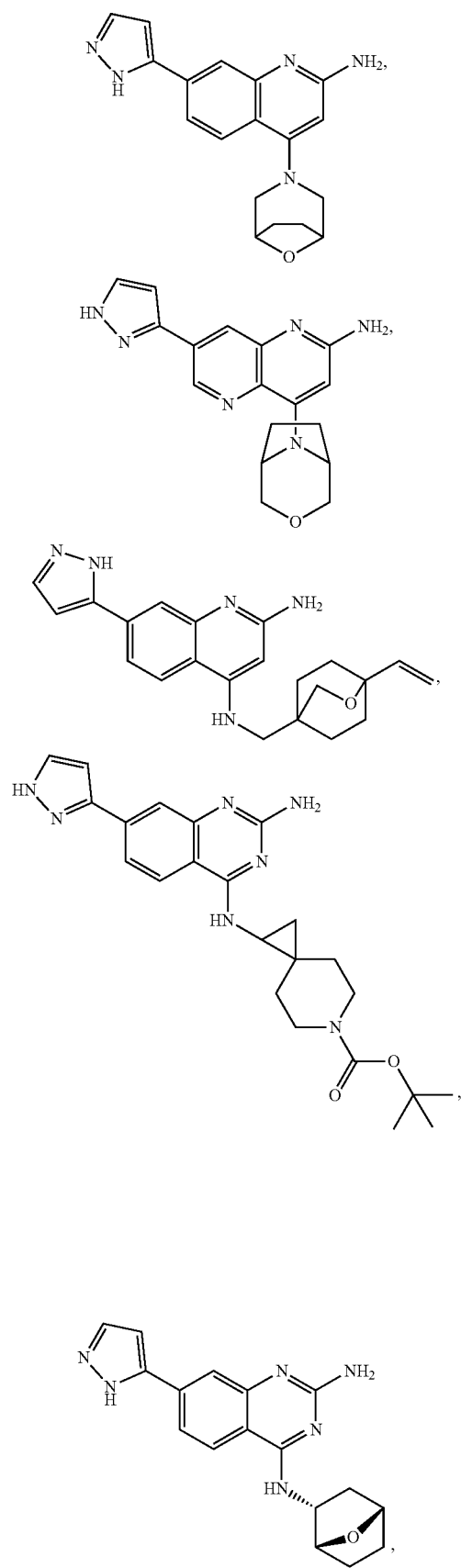
122
-continued
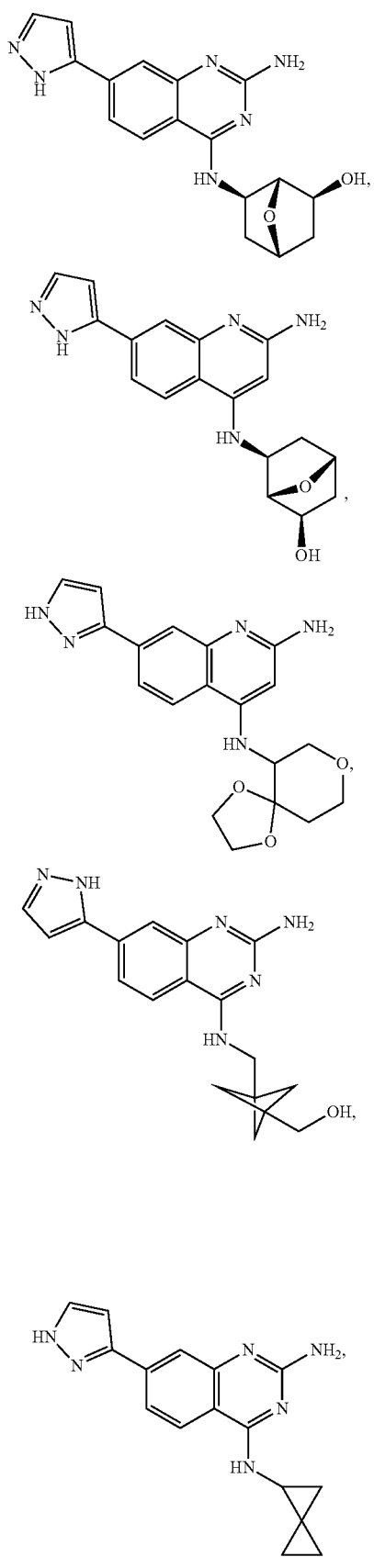

123
-continued
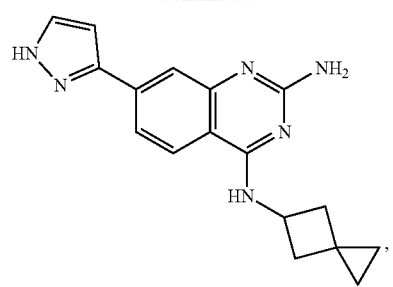
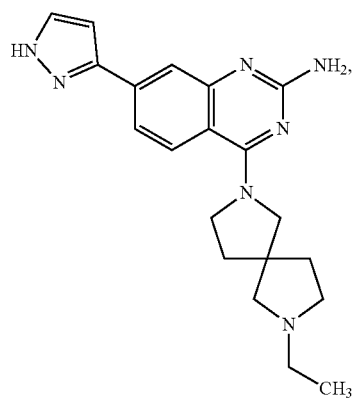
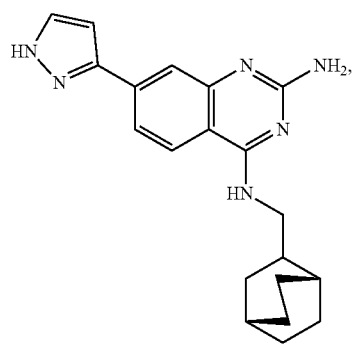
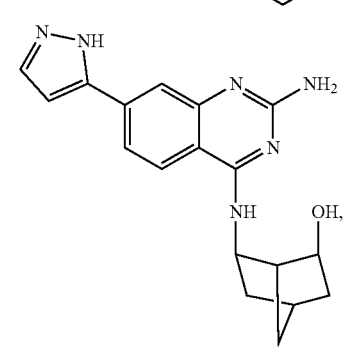
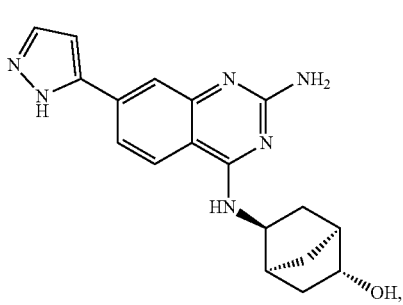
124
-continued
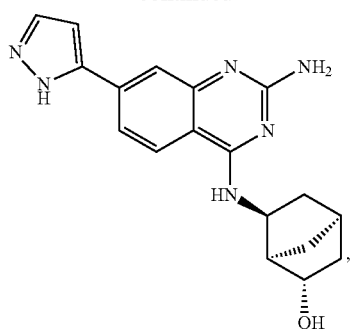
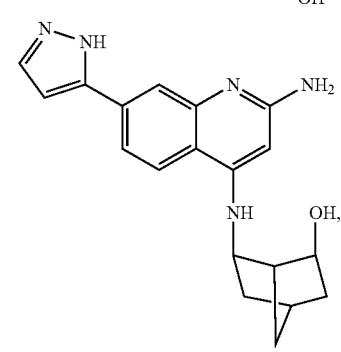
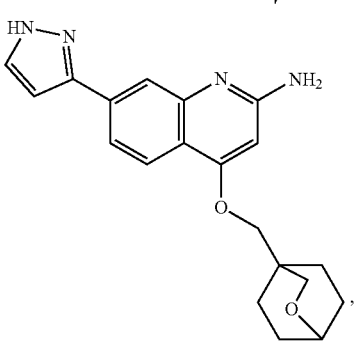
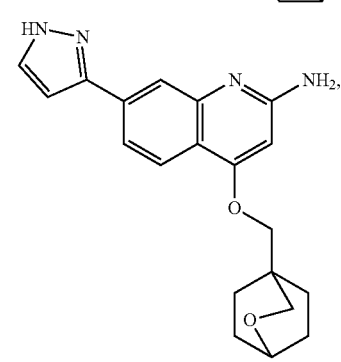
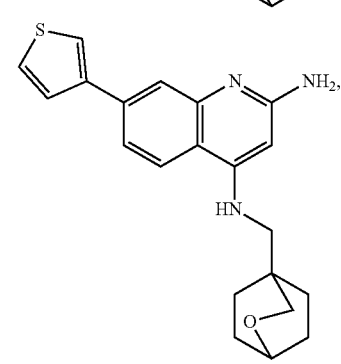

-continued

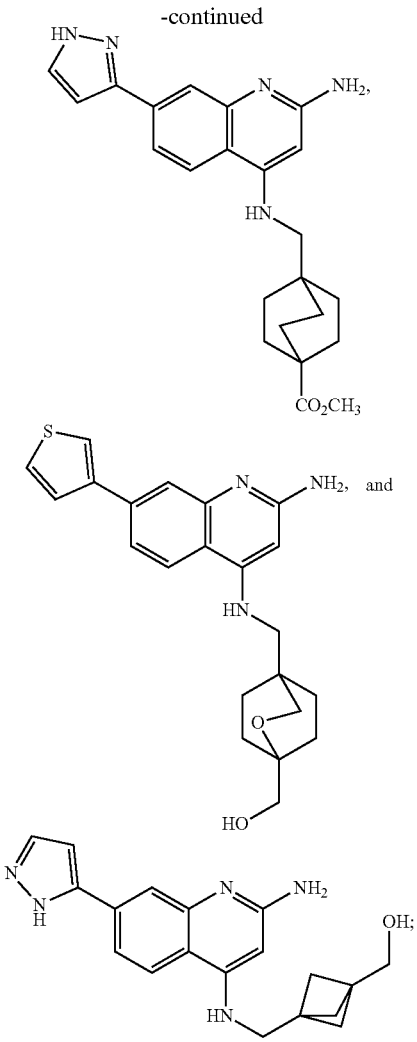

or a pharmaceutically acceptable salt thereof.

5. A pharmaceutical composition comprising a compound or a pharmaceutically acceptable salt thereof as claimed in claim 4 and one or more pharmaceutically acceptable excipients.

6. A method of treating cancer, comprising administering to a subject in need of such treatment an effective amount of a compound or a pharmaceutically acceptable salt thereof as claimed in claim 1.

7. The method of claim 6, wherein the cancer is selected from acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

8. The method of claim 6, wherein the cancer is selected from breast cancer, colon cancer, rectal cancer, colorectal cancer, pancreatic cancer, and prostate cancer.

9. The method of claim 6, wherein the cancer is selected from hormone receptor positive breast cancer, microsatellite stable colon or rectal cancer, pancreatic cancer and prostate cancer.

10. The method of claim 6, wherein the compound is administered in combination with one or more additional cancer therapies.

11. The method of claim 10, wherein the one or more additional cancer therapies comprise surgery, radiotherapy, chemotherapy, toxin therapy, immunotherapy, cryotherapy or gene therapy, or a combination thereof.

12. The method of claim 10, wherein the additional cancer therapy comprises one or more agents selected from nivolumab, pembrolizumab, PDR001, MEDI-0680, cemiplimab, JS001, BGB-A317, INCSHR1210, TSR-042, GLS-010, AM-0001, STI-1110, AGEN2034, MGD013, IBI308, BMS-936559, atezolizumab, durvalumab, avelumab, STI-1014, CX-072, LY3300054, CK-301, urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab, MK-1308, AGEN-1884, and tremelimumab.

13. The method of claim 10, wherein the additional cancer therapy comprises one or more agents selected from nivolumab, ipilimumab, pembrolizumab, atezolizumab, durvalumab and avelumab.

* * * * *